(12) United States Patent
Zeichner et al.

(10) Patent No.: US 12,734,234 B2
(45) Date of Patent: Sep. 15, 2026

(54) COMPOSITIONS AND METHODS FOR PREVENTING AND TREATING VIRUS INFECTION

(71) Applicant: University of Virginia Patent Foundation, Charlottesville, VA (US)

(72) Inventors: Steven L. Zeichner, Bethesda, MD (US); Barbie Ganser-Pornillos, Charlottesville, VA (US); Owen Pornillos, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 761 days.

(21) Appl. No.: 17/272,199

(22) PCT Filed: Aug. 27, 2019

(86) PCT No.: PCT/US2019/048396

§ 371 (c)(1),
(2) Date: Feb. 26, 2021

(87) PCT Pub. No.: WO2020/046982

PCT Pub. Date: Mar. 5, 2020

(65) Prior Publication Data

US 2021/0393768 A1 Dec. 23, 2021

Related U.S. Application Data

(60) Provisional application No. 62/723,131, filed on Aug. 27, 2018.

(51) Int. Cl.

| | |
|---|---|
| ***A61K 39/125*** | (2006.01) |
| ***A61P 31/14*** | (2006.01) |

(Continued)

(52) U.S. Cl.
CPC ............ *A61K 39/125* (2013.01); *A61P 31/14* (2018.01); *C12N 15/74* (2013.01);
(Continued)

(58) Field of Classification Search
None
See application file for complete search history.

(56) References Cited

U.S. PATENT DOCUMENTS

| | | | |
|---|---|---|---|
| 4,554,101 | A | 11/1985 | Hopp |
| 5,616,686 | A | 4/1997 | Fischetti et al. |

(Continued)

FOREIGN PATENT DOCUMENTS

| | | | |
|---|---|---|---|
| EP | 3833387 | A1 | 6/2021 |
| EP | 4045672 | A1 | 8/2022 |

(Continued)

OTHER PUBLICATIONS

Ramachandran et al. (PLOS. Neglected Tropical Diseases. 2015; 9 (1): e3394).*

(Continued)

*Primary Examiner* — Shanon A. Foley
(74) *Attorney, Agent, or Firm* — JENKINS, TAYLOR & HUNT, P.A.

(57) ABSTRACT

Disclosed herein are bacteria-based HIV MPER vaccine candidates, as well as bacteria-based candidates for other viruses and for bacteria. The HIV vaccine candidates express MPER-derived antigens on their surfaces using Gram autotransporters. The surface-expressed MPER antigens bind several different MPER-directed anti-HIV Broadly Neutralizing Monoclonal Antibodies. When the bacteria expressing the MPER-derived antigens on their surfaces are used to immunize mice they elicit the production of sera and vaginal wash material that bind the bacteria expressing the MPER antigens. At least one of the bacteria (Continued)

expressing MPER-derived antigens on their surfaces elicits the production of sera with anti-HIV neutralizing activity. Killed whole cell and live *Salmonella* expressing the MPER derived antigens on their surfaces constitute new approaches to HIV vaccine develop that is plausible and that could ultimately yield an inexpensive, globally appropriate candidate vaccine that could be rapidly produced and deployed largely using currently available technology.

27 Claims, 4 Drawing Sheets

Specification includes a Sequence Listing.

(51) Int. Cl.
*C12N 15/74* (2006.01)
*A61K 39/00* (2006.01)

(52) U.S. Cl.
CPC .. *A61K 2039/523* (2013.01); *A61K 2039/542* (2013.01); *A61K 2039/543* (2013.01); *A61K 2039/55544* (2013.01); *A61K 2039/575* (2013.01); *A61K 2039/6006* (2013.01)

(56) References Cited

U.S. PATENT DOCUMENTS 5,821,088 A 10/1998 Darzins et al.
5,958,736 A 9/1999 St.ang.hl et al.
7,094,598 B2 8/2006 Nabel et al.
7,314,974 B2 1/2008 Cao et al.
8,012,932 B2 9/2011 Klinefelter
8,592,205 B2 11/2013 Pinschewer et al.
8,628,782 B2 1/2014 Berkower
8,637,036 B2 1/2014 Mascola et al.
8,637,234 B2 1/2014 Shaw et al.
8,647,818 B2 2/2014 Shaw et al.
9,175,070 B2 11/2015 Mascola et al.
9,340,791 B2 5/2016 Blattner et al.
9,493,549 B2 11/2016 Diskin et al.
9,580,718 B2 2/2017 Curtiss, III et al.
9,695,230 B2 7/2017 Kwong et al.
9,885,051 B2 2/2018 Curtiss, III et al.
9,988,424 B2 6/2018 Haynes et al.
10,035,844 B2 7/2018 Kwong et al.
10,188,722 B2 1/2019 Bermudes
10,363,301 B2 7/2019 Mascola et al.
2008/0193469 A1 8/2008 Klinefelter
2009/0270312 A1 10/2009 Shai et al.
2010/0112670 A1* 5/2010 Giacalone .............. A61K 38/00
435/253.4
2010/0152059 A1* 6/2010 Zeichner ................. C40B 30/04
435/320.1
2011/0045529 A1 2/2011 Hori
2012/0208866 A1 8/2012 Brahmbhatt et al.
2016/0067327 A1 3/2016 Grifantini et al.
2016/0108407 A1 4/2016 Jose et al.
2016/0264664 A1 9/2016 Laeremans et al.
2017/0198297 A1 7/2017 Arrieumerlou et al.
2018/0087081 A1 3/2018 Hishiya et al.
2018/0162917 A1 6/2018 Charlton et al.
2018/0207260 A1 7/2018 Hernandez et al.
2019/0071706 A1 3/2019 Hewlett et al.
2021/0393768 A1* 12/2021 Zeichner ................. A61P 31/18
2022/0362361 A1 11/2022 Zeichner
2024/0261394 A1 8/2024 Zeichner et al.
2024/0309390 A1 9/2024 Zeichner et al.
2025/0332246 A1 10/2025 Zeichner

FOREIGN PATENT DOCUMENTS

EP 4138901 A1 3/2023
WO WO 1993/18163 9/1993
WO WO 1996/40943 12/1996
WO WO 1997/009437 3/1997
WO WO 00/014240 A2 3/2000
WO WO 2008/039408 A2 4/2008
WO WO 2010030986 A3 3/2010
WO WO2016/193370 * 12/2016
WO WO 2018/115140 A2 6/2018
WO WO 2020/172495 A1 8/2020
WO WO 2021/076897 A1 4/2021
WO WO 2021/231441 A1 11/2021
WO WO 2022/256427 A1 12/2022
WO WO 2023/081861 A1 5/2023

OTHER PUBLICATIONS

Hinz et al. (Virology. 2009;390: 221-227).*
Miller et al. (Viruses. 2021; 13: 1774).*
Tang et al. (Pathogens. 2023; 12: 497).*
Newton et al. (Research in Microbiology. 1995; 146 (3): 203-216).*
Williams et al. (Science. 2015; 349 (6249): aab1253).*
Haynes et al. (Nature Reviews Immunology. Mar. 2023; 23 (3): 142-158).*
Wieczorek et al. (Journal of Virology. 2015; 89 (15): 7478-7493).*
Seq Id No: 7 alignment with Geneseq db access No. AZG77045 in WO2011038290 by Mascola et al. 2011.*
Seq Id No: 9 alignment with Geneseq db access No. BEG89323 in WO2017143062 by Kyratsous et al.*
Seq Id No: 10 alignment with Geneseq db access No. AXV62568 in WO2010019262 by Fischer et al. 2010.*
Krebs et al. (PLoS ONE. 2014: 16; 9 (12): e113463).*
Chin'ombe & Ruhanya (2013) Open Virol J. 7:121-6.
Chin'ombe (2013) Viruses. 5(9):2062-78.
Curtiss et al. (2010) Crit Rev Immunol. 30(3):255-70.
Galen et al. (2009) Immunol Cell Biol. 87(5):400-12.
Hashimoto et al. (2005) Mol Microbiol. 55(1):137-49.
Henderson et al. (2000) Trends Microbiol. 8(12):529-532.
Ho et al. (2008) Infect Immun. 76(1):111-119.
International Preliminary Report on Patentability corresponding to International Application No. PCT/US2019/048396 dated Mar. 2, 2021.
International Search Report corresponding to International Application No. PCT/US2019/048396 dated Nov. 14, 2019.
Jiang et al. (2015) Avian Diseases. 59(4):475-85.
Jose & Meyer (2007) Microbiol Mol Biol Rev. 71(4):600-619.
Karpenko et al. (2012) Microb Biotechnol. 5(2):241-50. 3815784.
Kato & Hashimoto (2007) Mol Syst Biol. 3:132. PMC1964801.
Kjaergaard et al. (2002) J Bacteriol. 184(15):4197-4204.
Kong et al. (2012b) Proc Natl Acad Sci U S A. 109(47):19414-19419.
Kong et al. (2013) Expert Rev Vaccines. 12(4):345-347.
Kramer et al. (2003) Infect Immun. 71(4):1944-1952.
Li et al. (2008) Infect Immun. 76(11):5238-46. 2573344.
Meng et al. (2006) EMBO J. 25(11):2297-2304.
Rizos et al. (2003) Infect Immun. 71(11):6320-6328.
Ruiz-Perez et al. (2002) Infect Immun. 70(7):3611-3620.
Written Opinion corresponding to International Application No. PCT/US2019/048396 dated Nov. 14, 2019.
Xin et al. (2012) Infect Immun. 80(10):3621-33. 3457550.
Alexander J, et al., Linear PADRE T helper epitope and carbohydrate B cell epitope conjugates induce specific high titer IgG antibody responses. The Journal of Immunology. 2000;164(3):1625-33.
Díaz-Dinamarca., DA, et al., "Protein-based adjuvants for vaccines as immunomodulators of the innate and adaptive immune response: Current knowledge, challenges, and future opportunities," Pharmaceutics, 2022;14(8):1671.
Ghaffari-Nazari, H., et al., "Improving Multi-Epitope Long Peptide Vaccine Potency by Using a Strategy that Enhances CD4+ T Help in BALB/c Mice," PLoS One, Nov. 10, 2015, 10(11): e0142563, pp. 1-12.
Lu Y, et al., Functional properties of flagellin as a stimulator of innate immunity. Scientific reports. 2016;6(1):18379.

(56) References Cited

OTHER PUBLICATIONS

Mclachlan, JB, et al., Mast cell activators: a new class of highly effective vaccine adjuvants. Nature medicine. 2008;14(5):536-41.
Murthy, KG, et al., "Identification of conserved domains in *Salmonella muenchen* flagellin that are essential for its ability to activate TLR5 and to induce an inflammatory response in vitro," Journal of Biological Chemistry, 2004;279(7):5667-75.
Ontiveros-Padilla L, et al., Development of a broadly active influenza intranasal vaccine adjuvanted with self-assembled particles composed of mastoparan-7 and CpG. Frontiers in Immunology, 2023;14:1103765.
Rosa, DS, et al., The pan HLA DR-binding epitope improves adjuvant-assisted immunization with a recombinant protein containing a malaria vaccine candidate. Immunology letters. 2004;92(3):259-68.
Sanchez, P.L., et al. "Mastoparan-7 adjuvanted COBRA H1 and H3 hemagglutinin influenza vaccines," Sci Rep 14, 13800, pp. 1-11 (2024).
Alam, S.M., et al. "Role of HIV membrane in neutralization by two broadly neutralizing antibodies," Proc Natl Acad Sci U S A. vol. 106, No. 48, pp. 20234-20239 (2009).
Grifoni, A., et al., "A Sequence Homology and Bioinformatic Approach Can Predict Candidate Targets for Immune Responses to SARS-CoV-2," Cell Host & Microbe 27: pp. 671-680. (2020).
Alsaadi, E. A. J., et al., "A Fusion Peptide in the Spike Protein of MERS Coronavirus", Viruses, vol. 11, No. 9, 825, 2019, pp. 1-9. PMC6784214.
Altieri D.C., "Targeting surviving in cancer." Cancer lett., vol. 332, No. 2, May 28, 2013, pp. 225-228.
Amanat, F., et al., "SARS-CoV-2 Vaccines: Status Report", Immunity, vol. 52, 2020, pp. 583-589.
Ameiss, K., et al. "Delivery of woodchuck hepatitis virus-like particle presented influenza M2e by recombinant attenuated *Salmonella* displaying a delayed lysis phenotype," Vaccine, vol. 28, No. 41, pp. 6704-6713 (Sep. 24, 2010).
Ashraf, S., et al., "Protective cellular responses elicited by vaccination with influenza nucleoprotein delivered by a live recombinant attenuated *Salmonella* vaccine," Vaccine, vol. 29, No. 23, pp. 3990-4002 (2011).
Berry J.D., et al., "Rapid Monoclonal Antibody Generation Via Dendritic Cell Targeting In Vivo." Hybrid. Hybridomics, vol. 22, No. 1, 2003, pp. 23-31.
Bi Q., et al., "Protection against cholera from killed whole-cell oral cholera vaccines: a systematic review and meta-analysis", Lancet Infect Dis vol. 17, 2017, pp. 1080-1088.
Burton, D. R., et al., "Broadly Neutralizing Antibodies to HIV and Their Role in Vaccine Design," Annu Rev Immunol., May 20, 2016; 34; pp. 635-659.
Caillat, C., et al., "Neutralizing Antibodies Targeting HIV-1 gp41," Viruses. Oct. 23, 2020;12(11), pp. 1-19.
Carleton H.A., et al., "Engineering the type III secretion system in non-replicating bacterial minicells for antigen delivery." Nat Commun. vol. 4, Article 1590, Mar. 12, 2013, pp. 1-8.
Chen D.J., et al., "Delivery of foreign antigens by engineered outer membrane vesicle vaccines." Proc. Natl. Acad. Sci. USA, vol. 107, No. 7, Feb. 16, 2010, pp. 3099-3104.
Chen et al: "Comparison of a fimbrial versus an autotransporter display system for viral epitopes on an attenuated *Salmonella* vaccine vector", Vaccine, Elsevier, Amsterdam, NL, vol. 25, No. 9, Jan. 19, 2007 (Jan. 19, 2007), pp. 1626-1633.
Chen H., et al., "Response of Memory CD8 T Cells to Severe Acute Respiratory Syndrome (SARS) Coronavirus in Recovered SARS Patients and Healthy Individuals1", J Immunol, vol. 175, No. 1, 2005, pp. 591-598.
Chen X., et al., "Survivin and Tumorigenesis: Molecular Mechanisms and Therapeutic Strategies." J. Cancer, vol. 7, No. 3, 2016, Jan. 10, 2016, pp. 314-323.
Chen Y., et al., "Emerging coronaviruses: Genome structure, replication, and pathogenesis", J Med Virol vol. 92, 2020, pp. 418-423.
Cohen, J., "Vaccine wagers on coronavirus surface protein pay off", Science, vol. 370, No. 6519, 2020, pp. 894-895.
Colman, P. M., "The structural biology of type I viral membrane fusion", Nature Reviews Molecular Cell Biology, vol. 4, No. 4, 2003, pp. 309-319.
Corey L., et al. "A strategic approach to COVID-19 vaccine R&D", Science, vol. 368, May 29, 2020, pp. 948-950.
Cotter, S.E., et al., "Trimeric autotransporters: a distinct subfamily of autotransporter proteins," Trends in Microbiology, vol. 13, No. 5, May 2005, pp. 199-205.
Cui, J., et al., "Origin and evolution of pathogenic coronaviruses", Nature Reviews, Microbiology, vol. 17, 2019, pp. 181-192.
Datsenko K.A., et al., "One-step inactivation of chromosomal genes in *Escherichia coli* K-12 using PCR products." Proc. Natl. Acad. Sci. USA, vol. 97, No. 12, Jun. 6, 2000, pp. 6640-6645.
Dautin N., et al., "Protein Secretion in Gram-Negative Bacteria via the Autotransporter Pathway," Annu. Rev. Microbiol. 2007. 61:89-112.
Davis, "Nasal vaccines." Adv. Drug Deliv. Rev., vol. 51, No. 1-3, 2001, pp. 21-42.
De Boer P.A.J., et al., "A division inhibitor and a topological specificity factor coded for by the minicell locus determine proper placement of the division septum in *E coli*." Cell, vol. 56, No. 4, 1989, pp. 641-649.
Delany I., et al., "Vaccines for the 21st century." EMBO Mol. Med., vol. 6, No. 6, 2014, pp. 708-720.
Dhanak D., et al., "Small-Molecule Targets in Immuno-Oncology." Cell. Chem. Bio., vol. 24, No. 9, 2017, pp. 1148-1160.
Dias, W., et al., "An improved whole cell pertussis vaccine with reduced content of endotoxin. Human Vaccines & Immunotherapeutics", vol. 9, No. 2, Feb. 2013, pp. 339-348.
Dorp, L.V., et al., "Emergence of genomic diversity and recurrent mutations in SARS-CoV-2," Infect Genet Evol, vol. 83:104351 (2020).
Dou, J-L., et al., "Surface display of domain III of Japanese encephalitis virus E protein on *Salmonella typhimurium* by using an ice nucleation protein", Virologica Sinica, vol. 26, No. 6, Dec. 10, 2011.
Elslande, J.V., et al., "Symptomatic Severe Acute Respiratory Syndrome Coronavirus 2 (SARS-CoV-2) Reinfection by a Phylogenetically Distinct Strain," Clin Infect Dis., vol. 73, No. 2, pp. 354-356 (2021).
Extended European Search Report corresponding to European Patent Application No. 20875848.2-1111 dated Oct. 24, 2023, 13 Pages.
Fangusaro J.R., et al., "Survivin: An inhibitor of apoptosis in pediatric cancer." Pediatr. Blood Cancer, vol. 47, No. 1, pp. 4-13, 2006.
Farley M.M., et al., "Minicells, Back in Fashion." J. Bacterial., vol. 198, No. 8, Apr. 2016, pp. 1186-1195.
Finkelstein S.E., et al., "Cellular immunotherapy for soft tissue sarcomas." Immunotherapy, vol. 4, No. 3, 2012, pp. 283-290.
Garg H., et al., "Survivin: a unique target for tumor therapy." Cancer Cell Int., vol. 23, No. 16, Article No. 49, 2016, 14 Pages.
Garmory, H.S., et al., "Oral immunisation with live aroA attenuated *Salmonella enterica* serovar Typhimurium expressing the Yersinia pestis V antigen protects mice against plague," Vaccine. vol. 21, No. 21-22, pp. 3051-3057, Jun. 20, 2003.
Gerdes J., et al., "Cell cycle analysis of a cell proliferation-associated human nuclear antigen defined by the monoclonal antibody Ki-67" J. Immunol., vol. 133, No. 4, Oct. 1, 1984, pp. 1710-1715.
Graham et al. "Novel vaccine technologies: essential components of an adequate response to emerging viral diseases", JAmMed Assoc, vol. 319, 2018, pp. 1431-1432.
Gretebeck, L. M., et al., "Animal models for SARS and MERS coronaviruses", Current Opinion in Virology, vol. 13, pp. 123-129, 2015.
Grin I., et al., "A Trimeric Lipoprotein Assists In Trimeric Autotransporter Biogenesis In Enterobacteria." J bio chem, vol. 289, No. 11, Mar. 14, 2014, pp. 7388-7398.

(56) References Cited

OTHER PUBLICATIONS

Gu J., et al. "COVID-19: gastrointestinal manifestations and potential fecal-oral transmission", Gastroenterology, vol. 158, 2020, pp. 1518-1519.
Hanafi R., et al., "COVID-19 Neurologic Complication with CNS Vasculitis-Like Pattern",Am J Neuroradiol, vol. 41, Aug. 2020, pp. 1384-1387.
Hangartner L., et al., "Antiviral antibody responses: the two extremes of a wide spectrum." Nat. Rev. Immunol., vol. 6, No. 3, Mar. 2006, pp. 231-243.
Harrison S., "Viral membrane fusion", Virology 479-480, May 1, 2015, pp. 498-507.
Hasbold J., et al., "Cell division number regulates IgG1 and IgE switching of B cells following stimulation by CD40 ligand and IL-4." Eur. J. Immunol., vol. 28, No. 3, 1998, pp. 1040-1051.
He, Y., et al., "Identification of Immunodominant Sites on the Spike Protein of Severe Acute Respiratory Syndrome (SARS) Coronavirus: Implication for Developing SARS Diagnostics and Vaccines" The Journal of Immunology, vol. 173, No. 6, 2004, pp. 4050-4057.
Hidalgo S., et al., "Paralytic poliomyelitis caused by a vaccine-derived polio virus in an antibody-deficient Argentinean child." Pediatr. Infect. Dis. J., vol. 22, No. 6, Jun. 2003, pp. 570-572.
Hone, D. M., et al., "Optimization of live oral *Salmonella*-HIV-1 vaccine vectors for the induction of HIV-specific mucosal and systemic immune responses", Journal of Biotechnology, vol. 44, No. 1, pp. 203-207, Jan. 26, 1996.
Hovingh, E.S., et al. (2018). "Bordetella pertussis pertactin knock-out strains reveal immunomodulatory properties of this virulence factor," Emerg. Infect. Dis. 7(1): 1-13. (Year: 2018).
Huang et al. "Priming with Sars Cov S Dna and boosting with Sars Cov S epitopes specific for CD4+ and CD8+ T cells promote cellular immune responses," (2007) Vaccine. 25(39-40):6981-91.
Huang, J., et al., "Broad and potent neutralization of HIV-1 by a gp41-specific human antibody." Nature, vol. 491, pp. 406-412, Nov. 15, 2012.
Huang, Y.-W., et al., (2013). Origin, Evolution, and Genotyping of Emergent Porcine Epidemic Diarrhea Virus Strains in the United States. mBio, vol. 4. No. 5, pp. e00737-00713. doi: 10.1128/mBio.00737-13.
International Preliminary Report on Patentability Corresponding to International Application No. PCT/US2020/055995 dated Apr. 19, 2022, 8 Pages.
International Preliminary Report on Patentability Corresponding to International Application No. PCT/US2021/031798 dated Nov. 15, 2022, p. 7.
International Preliminary Report on Patentability Corresponding to International Application No. PCT/US2022/031807 dated Nov. 21, 2023, p. 8.
International Preliminary Report on Patentability Corresponding to International Application No. PCT/US2022/079351 dated May 2, 2024, p. 15.
International Search Report and the Written Opinion of the International Searching Authority Corresponding to International Application No. PCT/US2020/055995 dated Jan. 15, 2021, 11 Pages.
International Search Report and Written Opinion of the International Searching Authority Corresponding to International Patent Application No. PCT/US2021/031798 dated Sep. 14, 2021, 12 Pages.
International Search Report and Written Opinion of the International Searching Authority Corresponding to International Patent Application No. PCT/US2022/031807 dated Oct. 26, 2022, 12 Pages.
International Search Report and Written Opinion of the International Searching Authority Corresponding to International Patent Application No. PCT/US2022/079351 dated Mar. 22, 2023, 15 Pages.
Irimia, A., et al., "Lipid interactions and angle of approach to the HIV-1 viral membrane of broadly neutralizing antibody 10E8: Insights for vaccine and therapeutic design," PLoS Pathog. vol. 13, No. 2, e1006212, pp. 1-20, Feb. 22, 2017.
Jabbal-Gill, "Nasal vaccine innovation." J. Drug. Target. vol. 18(10), pp. 771-786 (2010).
Jain S., et al., "Polar Localization of the Autotransporter Family of Large Bacterial Virulence Proteins." J. Bacterial., vol. 188, No. 13, Jul. 2006, pp. 4841-4850.
Jiang, L., et al.,"COVID-19 and multisystem inflammatory syndrome in children and adolescents", The Lancet Infectious Diseases, vol. 20, 11, 2020, pp. e276-e288.
Johansen, M. D., et al., "Animal and translational models of SARS-CoV-2 infection and COVID-19", Mucosal Immunology, vol. 13, No. 6, 2020, pp. 877-891.
Jong, W. S., et al., (2012). "A structurally informed autotransporter platform for efficient heterologous protein secretion and display", Microbial Cell Factories, vol. 11, No. 85, 2012, 12 Pages.
Jung, K., et al., "Porcine epidemic diarrhea virus infection: Etiology, epidemiology, pathogenesis and immunoprophylaxis", The Veterinary Journal, vol. 204, No. 2, Feb. 18, 2015, pp. 134-143.
Kanekiyo M., et al. "New Vaccine Design and Delivery Technologies", The Journal of Infectious Diseases, vol. 219. 2019, pp. S88-S96.
Kavunja H.W., et al., "Delivery of foreign cytotoxic T lymphocyte epitopes to tumor tissues for effective antitumor immunotherapy agaist pre-established solid tumors in mice." Cancer Immunol. Immunother., vol. 66, No. 4. 2017 pp. 451-460.
Kilpatrick K.E., et al., "Rapid Development of Affinity Matured Monoclonal Antibodies Using RIMMS." Hybridoma, vol. 16, No. 4, 1997, pp. 381-389.
Klebanoff C.A., et al., "CD8+ T-cell memory in tumor immunology and immunotherapy." Immunol. Rev., vol. 211, Jun. 2006, pp. 214-224.
Klebanoff C.A., et al., "Central memory self/tumor-reactive CD8+ T cells confer superior antitumor immunity compared with effector memory T cells." Proc. Natl. Acad. Sci. USA, vol. 102, No. 27, Jul. 5, 2005, pp. 9571-9576.
Kohyama, S., et al., "Efficient induction of cytotoxic T lymphocytes specific for severe acute respiratory syndrome (SARS)-associated coronavirus by immunization with surface-linked liposomal peptides derived from a non-structural polyprotein 1a", Antiviral Research, vol. 84, No. 2, 2009, pp. 168-177.
Kotton, C.N., et al., "Safety and immunogenicity of attenuated *Salmonella enterica* serovar Typhimurium delivering an HIV-1 Gag antigen via the *Salmonella* Type III secretion system," Vaccine. vol. 24, No. 37-39, pp. 6216-6224. (2006).
Labreck C.J., et al., "MinC N- and C-Domain Interactions Modulate FtsZ Assembly, Division Site Selection, and MinD-Dependent Oscillation in *Escherichia coli*." J. Bacterial., vol. 201, No. 4, Article ID e00374-18, Nov. 19, 2019, 55 Pages.
Lattemann C T et al., "Autodisplay: Functional Display Of Active Beta-Lactamase on the Surface of *Escherichia coli* by the Aida-I Autotransporter", Journal Of Bacteriology, American Society For Microbiology, US, vol. 182, No. 13, Jul. 1, 2000, pp. 3726-3733.
Lee, J.S., et al. (2000), "Surface-displayed viral antigens on *Salmonella* carrier vaccine," Nat Biotechnol. 18(6):645-648.
Lee et al. (2020) "Evidence of Severe Acute Respiratory Syndrome Coronavirus 2 Reinfection After Recovery from Mild Coronavirus Disease 2019," Clinical Infectious Diseases, vol. 73, Issue 9, pp. e3002-e3008.
Lee et al. "Microbial cell-surface display", in Trends Biotechnology, vol. 21(1):2003, pp. 45-52.
Li C., et al., "Presentation of functional organophosphorus hydrolase fusions on the surface of *Escherichia coli* by the AIDA-I autotransporter pathway." Biotechnol. Bioeng., vol. 99, No. 2, Published online Jul. 5, 2007, pp. 485-490 (2008).
Li et al., "Attenuated Bordetella pertussis BPZE1 as a live vehicle for heterologous vaccine antigens delivery through the nasal route", Bioengineered Bugs, Searched (IPC), vol. 2, No. 6, Nov. 1, 2011, pp. 315-319.
Lu, R., et al., (2020). "Genomic characterisation and epidemiology of 2019 novel coronavirus: implications for virus origins and receptor binding", The Lancet, vol. 395, No. 10224, Jan. 29, 2020, pp. 565-574.
Lu, Y., et al., "Virus-like particle vaccine with B-cell epitope from porcine epidemic diarrhea virus (PEDV) incorporated into hepatitis

(56) References Cited

OTHER PUBLICATIONS

B virus core capsid provides clinical alleviation against PEDV in neonatal piglets through lactogenic immunity" Vaccine vol. 38, 2020, pp. 5212-5218.
Luria-Perez et al., "A fusogenic peptide expressed on the surface of *Salmonella enterica* elicits CTL responses to a dengue virus epitope", Searched (IPC) Vaccine, Elsevier, Amsterdam, NL, vol. 25, No. 27, Jun. 9, 2007, pp. 5071-5085.
Lv, Y., et al., 2009 "Identification of a novel conserved HLA-A*0201-restricted epitope from the spike protein of SARS-CoV", BMC Immunology, vol. 10, No. 1, 2009, 61, pp. 1-9.
Thulasingam, M., et al., "Characterization of *Salmonella typhi* OmpC and OmpF porins engineered with HIV-gp41 epitope on the surface loops: HIV-gp41 Epitope Display on *S. typhi* Porins", Proteins: Structure, Function, and Bioinformatics, vol. 85, No. 4, Feb. 3, 2017, pp. 657-664.
Madu, I. G., "Characterization of a Highly Conserved Domain within the Severe Acute Respiratory Syndrome Coronavirus Spike Protein S2 Domain with Characteristics of a Viral Fusion Peptide", Journal of Virology, vol. 83, No. 15, Aug. 2009, pp. 7411-7421.
Maecker H.T., et al., "Impact of cryopreservation on tetramer, cytokine flow cytometry, and ELISPOT." BMC Immunol. vol. 6 Article No. Jul. 17, 18, 2005, 14 Pages.
Maecker H.T., et al., "Standardizing immunophenotyping for the Human Immunology Project." Nat. Rev. Immunol., vol. 12, No. 3, 2012, pp. 191-200, 21 Pages.
Maeda D.L.N.F., et al., "Killed whole-genome reduced-bacteria surface-expressed coronavirus fusion peptide vaccines protect against disease in a porcine model", Proceedings of the National Academy of Sciences, vol. 118, No. 18, Apr. 15, 2021, pp. 1-10.
Majzner R.G., et al., "Harnessing the Immunotherapy Revolution for the Treatment of Childhood Cancers." Cancer Cell, vol. 31, No. 4, Apr. 10, 2017, pp. 476-485.
Mamat U., et al., "Detoxifying *Escherichia coli* for endotoxin-free production of recombinant proteins", Microbial Cell Factories, Springer, vol. 14, No. 1, 57, Apr. 16, 2015 (Apr. 16, 2015), pp. 1-15.
Mccray, P. B., et al., "Lethal Infection of K18-hACE2 Mice Infected with Severe Acute Respiratory Syndrome Coronavirus", Journal of Virology, vol. 81, No. 2, pp. 813-821.
Mcmahan, K., et al., "Correlates of protection against SARS-CoV-2 in rhesus macaques", Nature, vol. 590, Dec. 4, 2020, doi:10.1038/s41586-020-03041-6.
Melief C.J.M., et al., "Therapeutic cancer vaccines." J. Clin. Invest., vol. 125, No. 9, Sep. 2015, pp. 3401-3412.
Meurens, F., et al., "The pig: a model for human infectious diseases", Trends in Microbiology, vol. 20, No. 1, Jan. 2012, pp. 50-57.
Miyoshi-Akiyama T., et al., "Fully Human Monoclonal Antibody Directed to Proteolytic Cleavage Site in Severe Acute Respiratory Syndrome (SARS) Coronavirus S Protein Neutralizes the Virus in a Rhesus Macaque SARS Model", J Infect Dis, Jun. 1, 2011, vol. 203, No. 11, pp. 1574-81.
Morabito K.M., et al., "Intranasal administration of RSV antigen-expressing MCMV elicits robust tissue resident effector and effector memory CD8+ T cells in the lung." Mucosal. Immunol., vol. 10, No. 2, 2017, pp. 545-554.
Nagaraj S., et al., "Dendritic Cell-based Full-length Survivin Vaccine in Treatment of Experimental tumors," J. Immunother., vol. 30, No. 2, Feb./Mar. 2007, pp. 169-179.
Newman M.A., et al., "Patterns of antibody specificity during the BALB/c immune response to hen eggwhite lysozyme." J. Immunol., vol. 149(10), 1992, pp. 3260-3272.
Ng, K. W., et al., "Preexisting and de novo humoral immunity to SARS-CoV-2 in humans", Science, vol. 370, No. 6522, 2020, pp. 1339-1343.
Nicolay, T., et al., "Autotransporter-based cell surface display in Gram-negative bacteria." Crit. Rev. Microbial. vol. 41(1), pp. 109-123 (2013).
Nizard M., et al., "Induction of resident memory T cells enhances the efficacy of cancer vaccine." Nat. Commun., vol. 8, Article No. 15221, May 24, 2017, 11 Pages.
Notice of Publication corresponding to European Application No. 20875848.2-111 dated Jul. 27, 2022, 1 page.
Odevall, L., et al., (2018). "The Euvichol story—Development and licensure of a safe, effective and affordable oral cholera vaccine through global public private partnerships", Vaccine, vol. 36, pp. 6606-6614.
Office Action (Restriction Requirement) for U.S. Appl. No. 17/769,899, mailed on Dec. 5, 2024, 11 Pages.
Oliveira, M. L. S., et al., "Intranasal vaccines for protection against resipratory and systemic bacterial infections", Expert Review of Vaccines, vol. 6, No. 3, 2007, pp. 419-429.
Onodera T., et al., "CD22 Regulates Time Course of Both B Cell Division and Antibody Response." J. Immunol., vol. 180, No. 2, 2008, pp. 907-913.
Opriessnig, T., et al., (2014). "Porcine Epidemic Diarrhea Virus RNA Present in Commercial Spray-Dried Porcine Plasma Is Not Infectious to Naïve Pigs", PLoS ONE, vol. 9, No. 8, e104766, pp. 1-10.
Ou B., et al: "Genetic engineering of probiotic *Escherichia coli* Nissle 1917 for clinical application", Applied Microbiology and Biotechnology, Springer Berlin Heidelberg, Berlin/Heidelberg, vol. 100, No. 20, Sep. 17, 2016 (Sep. 17, 2016), pp. 8693-8699.
Ou, X., et al., "Identification of the Fusion Peptide-Containing Region in Betacoronavirus Spike Glycoproteins," J Virol, vol. 90, No. 12, pp. 5586-5600. (2016).
Pinto, D., et al., "Structural Basis for Broad HIV-1 Neutralization by the MPER-Specific Human Broadly Neutralizing Antibody LN01," Cell Host Microbe. Nov. 13, 2019;26(5):623-637.e8. Epub Oct. 22, 2019.
Poh, C.M., et al., "Two linear epitopes on the SARS-CoV-2 spike protein that elicit neutralising antibodies in COVID-19 patients," Nat Commun, vol. 11, article 2806 (2020).
Pratelli, A., et al., "Safety and efficacy of a modified-live canine coronavirus vaccine in dogs," Vet Microbial, vol. 99, pp. 43-49 (2004).
Qin H., et al., "Generation of a new therapeutic peptide that depletes myeloid-derived suppressor cells in tumor-bearing mice," Nat. Med., vol. 20, No. 6, May 25, 2014, pp. 676-681.
Rauch et al. (2018) "New vaccine technologies to combat outbreak Situations," Frontiers in Immunology 19; 9: 1963. pp. 1-47.
Rey, F.A., "Common Features of Enveloped Viruses and Implications for Immunogen Design for Next-Generation Vaccines," Cell, vol. 172, pp. 1319-1334 (2018).
Riese P., et al., "Intranasal formulations: promising strategy to deliver vaccines." Expert Opin. Drug Deliv., vol. 11, No. 10, 2014, pp. 1619-1634.
Roe O.D., "The High Cost of New Cancer Therapies—A Challenge of Inequality for All Countries", JAMA Oncol., vol. 3, No. 9, Sep. 2017, pp. 1169-1170.
Roost H-P., et al., "Early high-affinity neutralizing anti-viral IgG responses without further overall improvements of affinity" Proc. Natl. Acad. Sci. US, vol. 92, No. 5, Feb. 1995, pp. 1257-1261.
Rosano G.L., et al., "Recombinant protein expression in *Escherichia coli*: advances and challenges", Frontiers in Microbiology, vol. 5, Article. 172,Apr. 17, 2014 (Apr. 17, 2014) pp. 1-17.
Rostad, C. A., et al., Quantitative SARS-CoV-2 Serology in Children With Multisystem Inflammatory Syndrome (MIS-C), Pediatrics, vol. 146, No. 6, e2020018242. (2020).
Ruiz-Olvera, P., et al., (2003). Display and release of the Plasmodium falciparum circumsporozoite protein using the autotransporter MisL of *Salmonella enterica*. Plasmid, vol. 50, No. 1, pp. 12-27.
Russell M.W., "Immunization for Protection of the Reproductive Tract: A Review." Am. J. Reprod. Immunol., vol. 47, No. 5, 2002, pp. 265-268.
Samuelson P, et al., "Display of proteins on bacteria", Journal of Biotechnology, Elsevier, Amsterdam NL, vol. 96, No. 2, Jun. 26, 2002 (Jun. 26, 2002), pp. 129-154.
Sarmento, L.V., et al., "Detection of porcine epidemic diarrhea virus-neutralizing antibody using high-throughput imaging cytometry," J Vet Diagn Invest, vol. 32, No. pp. 324-328 (2020).
Seder R.A., et al., "Similarities and difference in CD4+ and CD8+ effector and memory T cell generation." Nat. Immunol., vol. 4, No. 9, Sep. 2003, pp. 835-842.

(56) References Cited

OTHER PUBLICATIONS

Shahabi V., et al., "Live, attenuated strains of Listeria and *Salmonella* as vaccine vectors in cancer treatment", Bioengineered Bugs, vol. 1, No. 4, Jan. 1, 2010, pp. 237-245.
Shata M.T., et al., "Recent advances with recombinant bacterial vaccine vectors." Mol. Med. Today, Feb. 2000, vol. 6, No. 2, pp. 66-71.
Shata, M. T., (2001). Mucosal and systemic HIV-1 Env-specific CD8+ T-cells develop after intragastric vaccination with a *Salmonella* Env DNA vaccine vector. Vaccine, 20(3-4), 623-629.
Shen, C-H., et al., "VRC34-Antibody Lineage Development Reveals How a Required Rare Mutation Shapes the Maturation of a Broad HIV-Neutralizing Lineage," Cell Host Microbe. vol. 27, No. 4, pp. 531-543.e6. (2020).
Shi H., et al., "Immunogenicity of a Live Recombinant *Salmonella enterica* Serovar Typhimurium Vaccine Expressing pspA in Neonates and Infant Mice Born from Naïve and Immunized Mothers", (2010a) Clin Vaccine Immunol. 17(3):363-371.
Shi, H., et al (2013). Evaluation of Regulated Delayed Attenuation Strategies for *Salmonella enterica* Serovar Typhi Vaccine Vectors in Neonatal and Infant Mice. Clinical and Vaccine Immunology, 20(6), 931-944.
Shi, H., et al., (2010). Live Recombinant *Salmonella typhi* Vaccines Constructed to Investigate the Role of rpoS in Eliciting Immunity to a Heterologous Antigen. PLoS ONE, 5(6), e11142.
Shoemaker D.R., et al., "Intranasal Delivery of Group B Meningococcal Native Outer Membrane Vesicle Vaccine Induces Local Mucosal and Serum Bactericidal Antibody Responses in Rabbits." Infect. Immunol., vol. 73, No. 8, Aug. 2005, pp. 5031-5038.
Shrock, E., et al., "Viral epitope profiling of COVID-19 patients reveals cross-reactivity and correlates of severity," Science , vol. 370, No. 6520, eabd4250, pp. 1-23, (2020).
Sia, S.F., et al., "Pathogenesis and transmission of SARS-CoV-2 in golden hamsters," Nature, vol. 583, No. 7818, pp. 834-838 (2020).
Sonnenborn U., et al., "The non-pathogenic *Escherichia coli* strain Nissle 1917-features of a versatile probiotic", Microbial Ecology in Health & Disease, Co-Action Publishing, SE, vol. 21, No. 3-4, Jan. 1, 2009 (Jan. 1, 2009), pp. 122-158.
Sowa M.E., et al., "Defining the Human Deubiquitinating Enzyme Interaction Landscape." Cell, vol. 138, No. 2, Jul. 24, 2009, pp. 389-403.
Stavnezer J., et al., "Mechanism and Regulation of Class Switch Recombination." Annu. Rev. Immunol., vol. 26, 2008, pp. 261-292.
Sturmhoefel H., et al., "Potent Activity of Soluble 87-IgG Fusion Proteins in Therapy of Established Tumors and as Vaccine Adjuvant." Cancer Res., vol. 59, No. 19, Oct. 1, 1999, pp. 4964-4972.
Subramaniam, S., et al., "Efficient priming of CD4 T cells by Langerin-expressing dendritic cells targeted with porcine epidemic diarrhea virus spike protein domains in pigs, " Virus Res. vol. 227, pp. 212-219 (2017).
Subramaniam, S., et al., "Vaccination of sows with a dendritic cell-targeted porcine epidemic diarrhea virus S1 protein-based candidate vaccine reduced viral shedding but exacerbated gross pathological lesions in suckling neonatal piglets," J Gen Virol. vol. 99, No. 2, pp. 230-239 (2018).
Supplementary European Search Report for European Application No. 19856026.0-1111, mailed on Apr. 12, 2022. 14 Pages.
Supplementary European Search Report corresponding to European Patent Application No. 21805280.1-1111 dated May 10, 2024, 7 Pages.
Tam H.H., et al., Sustained antigen availability during germinal center initiation enhances antibody responses to vaccination, Proc Natl Acad Sci U S A., vol. 113, No. 43, 2016, pp. E6639-E6648.
Thomsen A.R., et al., "Cooperation of B cells and T cells is required for survival of mice infected with vesicular stomatitis virus." Int. Immunol., vol. 9, No. 11, Aug. 11, 1997, pp. 1757-1766.
Tizard, I.R., "Vaccination against coronaviruses in domestic animals," Vaccine, vol. 38, pp. 5123-5130 (2020).
Tsao, Y-P., "HLA-A*0201 T-cell epitopes in severe acute respiratory syndrome (SARS) coronavirus nucleocapsid and spike proteins," Biochem Biophys Res Commun., vol. 344, No. 1, pp. 63-71 (2006).
Ulmer J.B., et al., "Vaccine manufacturing: challenges and solutions." Nat. Biotechnol., vol. 24, No. 11, Nov. 2006, pp. 1377-1383.
Unnikrishnan M., et al., "Recombinant bacterial vaccines." Curr. Opin. Immunol., vol. 24, No. 3, 2012, pp. 337-342.
Van Bloois, E., et al., "Decorating microbes: surface display of proteins on *Escherichia coli*." Trends Biotechnol., vol. 29, No. 2, 2011, pp. 79-86.
Vincent J., et al., "5-Fluorouracil selectively kills tumor-associated myeloid-derived suppressor cells resulting in enhanced T cell-dependent antitumor immunity." Cancer Research., vol. 70, No. 8, Apr. 15, 2010, pp. 3052-3061.
Walls, A.C., et al., "Structure, Function, and Antigenicity of the SARS-CoV-2 Spike Glycoprotein," Cell, vol. 181, No. 2, pp. 281-292, 2020.
Wang et al. "*Salmonella* Vaccine Vectors Displaying Delayed Antigen Synthesis InVivo To Enhance Immunogenicity" (2010) Infect Immun. vol. 78, No. 9, pp. 3969-3980.
Wang, B., et al., "Identification of an HLA-A*0201-restricted CD8+ T-cell epitope SSp-1 of SARS-CoV spike protein," Blood, vol. 104, No. 1, pp. 200-206 (2004).
Wang, L-F., et al., "Viruses in bats and potential spillover to animals and humans," Curr Opin Virol, vol. 34, pp. 79-89, 2019.
Wang, Q, et al., "Emerging and re-emerging coronaviruses in pigs," Curr Opin Virol, vol. 34, pp. 39-49 (2019).
Wang, Y-D., et al. "T-cell epitopes in severe acute respiratory syndrome (SARS) coronavirus spike protein elicit a specific T-cell immune response in patients who recover from SARS," J Virol. vol. 78, No. 11, pp. 5612-5618 (2004).
Warrier N.M., et al., "Emerging Importance of Survivin in Stem Cells and Cancer: the Development of New Cancer Therapeutics." Stem Cell Rev. Rep., vol. 16, No. 5, Jul. 20, 2020, pp. 828-852.
Wrapages, D., et al., "Cryo-EM structure of the 2019-nCoV spike in the prefusion conformation," Science, vol. 367:1260-1263 (2020).
Xia, S., et al., "Fusion mechanism of 2019-nCoV and fusion inhibitors targeting HR1 domain in spike protein," Cell Mol Immunol, vol. 17, No. 7, pp. 765-767 (2020).
Xu, K., et al., "Epitope-based vaccine design yields fusion peptide-directed antibodies that neutralize diverse strains of HIV-1," Nat Med vol. 24, pp. 857-867 (2018).
Yang Y., et al., "Oral vaccination with Ts87 DNA vaccine delivered by attenuated *Salmonella typhimurium* elicits a protective immune response against Trichinella spiralis larval challenge." Vaccine, vol. 28, No. 15, Jan. 25, 2010, pp. 2735-2742.
Yang, J., et al. Searching immunodominant epitopes prior to epidemic: HLA class II-restricted SARS-CoV spike protein epitopes in unexposed individuals, Int Immunol. vol. 21, No. 1, pp. 63-71 (2009).
Yonker, L, M., et al., "Pediatric Severe Acute Respiratory Syndrome Coronavirus 2 (SARS-CoV-2): Clinical Presentation, Infectivity, and Immune Responses," J Pediatr. vol. 227, pp. 45-52. (2020).
Yusuf H., et al., "Current prospects and future challenges for nasal vaccine delivery." Hum. Vaccin. Immunother., vol. 13, No. 1, 2017, pp. 34-45.
Zaman M., et al., "Strategies for intranasal delivery of vaccines." Drug Deliv. Transl. Res., vol. 3(1), pp. 100-109 (2013).
Zeichner, S.L., "Multisystem Inflammatory Syndrome in Children and SARS-CoV-2 Serology," Pediatrics, vol. 146, No. 6, e2020032888., p. 11 (2020).
Zhai Y., et al., "Bovine papillomavirus-like particles presenting conserved epitopes from membrane-proximal external region of HIV-1 gp41 induced mucosal and systemic antibodies", Vaccine. vol. 31, No. 46, Nov. 4, 2013, pp. 5422-5429. PMC3881962.
Zhang, Y., et al., "Coagulopathy and Antiphospholipid Antibodies in Patients with Covid-19," N Engl J Med, vol. 382, No. 17, e38 (2020).
Zhou, M., et al., "Screening and identification of severe acute respiratory syndrome-associated coronavirus-specific CTL epitopes," J Immunol. vol. 177, No. 4, pp. 2138-2145 (2006).

(56) References Cited

OTHER PUBLICATIONS

Zhu K., et al., "Survivin DNA vaccine generated specific antitumor effects in pancreatic carcinoma and lymphoma mouse models." Vaccine, vol. 25, No. 46, pp. 7955-7961 (2007).
Del Guercio M-F, Alexander J, Kubo RT, Arrhenius T, Maewal A, Appella E, Hoffman SL, Jones T, Valmori D. Sakaguchi K. Potent immunogenic short linear peptide constructs composed of B cell epitopes and Pan DR T helper epitopes (PADRE) for antibody responses in vivo. Vaccine. 1997;15(4):441-8.
Diaz-Dinamarca DA, Manzo RA, Soto DA, Avendaño-Valenzuela MJ, Bastias DN, Soto PI, Escobar DF, Vasquez-Saez V, Carrión F, Pizarro-Ortega MS. Surface immunogenic protein of *Streptococcus* group B is an agonist of toll-like receptors 2 and 4 and a potential immune adjuvant. Vaccines. 2020;8(1):29.
Murthy, A.C., et al., "The (un)structural biology of biomolecular liquid-liquid phase separation using NMR spectroscopy," J Biol Chem, vol. 295 No. 8, pp. 2375-2384, 2020.
Baer, A., et al., "Viral concentration determination through plaque assays: using traditional and novel overlay systems," J Vis Exp., 93:e52065, pp. 1-10, Nov. 4, 2014.
Bolognesi, B., et al., "Physicochemical principles of protein aggregation," Prog Mol Biol Transl Sci., vol. 117, pp. 53-72, 2013.
Cromwell, M, E.M., et al., "Protein aggregation and bioprocessing," AAPS J., vol. 8, No. 3, E572-9, Sep. 15, 2006.
Dacon, C., et al., "Broadly neutralizing antibodies target the coronavirus fusion peptide," Science, vol. 377(6607), pp. 728-735, Aug. 12, 2022.
Dacon, C., et al., "Broadly neutralizing antibodies target the coronavirus fusion peptide," bioRxiv, Apr. 12, 2022, pp. 1-47.
Evans, D.G., et al., Non-replicating oral whole cell vaccine protective against enterotoxigenic *Escherichia coli* (ETEC) diarrhea: stimulation of anti-CFA (CFA/I) and anti-enterotoxin (anti-LT) intestinal IgA and protection against challenge with ETEC belonging to heterologous serotypes, FEMS Microbiol Immunol., vol. 1, No. 3.
Gorbenko, G., et al., "Protein aggregation in a membrane environment," Adv Protein Chem Struct Biol., vol. 84, pp. 113-142, (2011).
Graham, B.S., et al., "Structure-Based Vaccine Antigen Design," Annu Rev Med., vol. 70, pp. 91-104, Jan. 27, 2019.
Hays, M.P., et al., "Vaccinating with conserved *Escherichia coli* antigens does not alter the mouse intestinal microbiome," BMC Res Notes, vol. 9, No. 401, pp. 1-7, Aug. 11, 2016.
Kelly, H.G., et al., "Immunological basis for enhanced immunity of nanoparticle vaccines," Expert Review of Vaccines., vol. 18, No. 3, pp. 269-280, Mar. 2019.
Low, J.S., et al., "ACE2-binding exposes the SARS-CoV-2 fusion peptide to broadly neutralizing coronavirus antibodies," Science, 377(6607), pp. 735-742, Aug. 12, 2022.
Meuskens, I., et al., "Type V Secretion Systems: An Overview of Passenger Domain Functions," Front Microbiol, 10:1163, pp. 1-19, May 31, 2019.
Oladunni, F.S., et al., "Lethality of SARS-CoV-2 infection in K18 human angiotensin-converting enzyme 2 transgenic mice," Nat Commun., vol. 11, No. 1:6122, pp. 1-17, Nov. 30, 2020.
Pavot, V., et al., "New insights in mucosal vaccine development," Vaccine, vol. 30, No. 2, pp. 142-154, Jan. 5, 2012.
Savarino, A., et al., "Shock and kill" effects of class I-selective histone deacetylase inhibitors in combination with the glutathione synthesis inhibitor buthionine sulfoximine in cell line models for HIV-1 quiescence, Retrovirology., vol. 6, No. 52, pp. 1-10, Jun. 2, 2009.
Selim, S.A., et al., "The effect of *Escherichia coli* J5 and modified live *Salmonella* dublin vaccines in artificially reared neonatal calves," Vaccine, vol. 13, No. 4, pp. 381-390, Mar. 1995.
Slota, M., et al., "ELISpot for measuring human immune responses to vaccines," Expert Rev Vaccines., vol. 10, No. 3 pp. 299-306, Mar. 2011.
Sun. S-H., et al., "A Mouse Model of SARS-CoV-2 Infection and Pathogenesis," Cell Host Microbe, vol. 28, No. 1, pp. 124-133, May 27, 2020.
Sun, X., et al., "Neutralization mechanism of a human antibody with pan-coronavirus reactivity including SARS-CoV-2," Nature Microbiology, vol. 7, No. 7, pp. 1063-1074, Jul. 2022.
Ulsen, P.V., et al., "On display: autotransporter secretion and application," FEMS Microbiol Letters, vol. 365, No. 18, pp. 1-21, Sep. 1, 2018.
Seq Id No.: 9 alignment with Geneseq db access No. BEG89323 in W02017143062 by Kyratsous et al.
Seq Id No.: 10 alignment with Geneseq db access No. AXV62568 in W02010019262 by Fischer et al. 2010.
Office Action (Non-Final Rejection) for U.S. Appl. No. 17/769,899, mailed on Jun. 30, 2025, 23 Pages,.
Posfai et al. (2006). "Emergent Properties of Reduced-Genome *Escherichia coli*." Science, 312(5776):1044-1046. (Year: 2006).
Bonhivers et al. (1998). "FhuA, an *Escherichia coli* outer membrane protein with a dual function of transporter and channel which mediates the transport of phage DNA" Biochimie, 80(5):363-369. (Year: 1998).
Office Action (Restriction Requirement) for U.S. Appl. No. 17/924,963, mailed on Jul. 1, 2025, 8 Pages.
Office Action (Non-Final Rejection) for U.S. Appl. No. 17/924,963, mailed on Nov. 4, 2025, 22 Pages.
Meng G. et al., "Repetitive Architecture of the Haemophilus influenzae Hia Trimeric Autotransporter", J. Mol. Bioi., 2008, vol. 384, pp. 824-836. (Year: 2008).
Office Action (Restriction Requirement) for U.S. Appl. No. 18/566,497, mailed on Nov. 12, 2025, 8 Pages.
Office Action for European Patent Application No. 19856026.0-1111, mailed on Jun. 17, 2025, 11 Pages.

* cited by examiner

Dilution

SEQUENCE LISTING

```
<160> NUMBER OF SEQ ID NOS: 15

<210> SEQ ID NO 1
<211> LENGTH: 325
<212> TYPE: PRT
<213> ORGANISM: Artificial Sequence
<220> FEATURE:
<223> OTHER INFORMATION: Artificially synthesized peptide sequence

<400> SEQUENCE: 1
```

```
Gln Tyr Arg Pro Glu Asn Gly Ser Tyr Ala Thr Asn Met Ala Leu Ala
1               5                   10                  15

Asn Ser Leu Phe Leu Met Asp Leu Asn Glu Arg Lys Gln Phe Arg Ala
            20                  25                  30

Met Ser Asp Asn Thr Gln Pro Glu Ser Ala Ser Val Trp Met Lys Ile
        35                  40                  45

Thr Gly Gly Ile Ser Ser Gly Lys Leu Asn Asp Gly Gln Asn Lys Thr
    50                  55                  60

Thr Thr Asn Gln Phe Ile Asn Gln Leu Gly Gly Asp Ile Tyr Lys Phe
65                  70                  75                  80

His Ala Glu Gln Leu Gly Asp Phe Thr Leu Gly Ile Met Gly Gly Tyr
                85                  90                  95

Ala Asn Ala Lys Gly Lys Thr Ile Asn Tyr Thr Ser Asn Lys Ala Ala
            100                 105                 110

Arg Asn Thr Leu Asp Gly Tyr Ser Val Gly Val Tyr Gly Thr Trp Tyr
        115                 120                 125

Gln Asn Gly Glu Asn Ala Thr Gly Leu Phe Ala Glu Thr Trp Met Gln
    130                 135                 140

Tyr Asn Trp Phe Asn Ala Ser Val Lys Gly Asp Gly Leu Glu Glu Glu
145                 150                 155                 160

Lys Tyr Asn Leu Asn Gly Leu Thr Ala Ser Ala Gly Gly Gly Tyr Asn
                165                 170                 175

Leu Asn Val His Thr Trp Thr Ser Pro Glu Gly Ile Thr Gly Glu Phe
            180                 185                 190

Trp Leu Gln Pro His Leu Gln Ala Val Trp Met Gly Val Thr Pro Asp
        195                 200                 205

Thr His Gln Glu Asp Asn Gly Thr Val Val Gln Gly Ala Gly Lys Asn
    210                 215                 220

Asn Ile Gln Thr Lys Ala Gly Ile Arg Ala Ser Trp Lys Val Lys Ser
225                 230                 235                 240

Thr Leu Asp Lys Asp Thr Gly Arg Arg Phe Arg Pro Tyr Ile Glu Ala
                245                 250                 255

Asn Trp Ile His Asn Thr His Glu Phe Gly Val Lys Met Ser Asp Asp
            260                 265                 270

Ser Gln Leu Leu Ser Gly Ser Arg Asn Gln Gly Glu Ile Lys Thr Gly
        275                 280                 285

Ile Glu Gly Val Ile Thr Gln Asn Leu Ser Val Asn Gly Gly Val Ala
    290                 295                 300

Tyr Gln Ala Gly Gly His Gly Ser Asn Ala Ile Ser Gly Ala Leu Gly
305                 310                 315                 320

Ile Lys Tyr Ser Phe
                325


<210> SEQ ID NO 2
<211> LENGTH: 121
<212> TYPE: PRT
<213> ORGANISM: Artificial Sequence
<220> FEATURE:
<223> OTHER INFORMATION: Artificial peptide sequence

<400> SEQUENCE: 2

Leu Asn Pro Thr Lys Glu Ser Ala Gly Asn Leu Thr Val Ser Asn Tyr
1               5                   10                  15

Thr Gly Thr Pro Gly Ser Val Ile Ser Leu Gly Gly Val Leu Glu Gly
            20                  25                  30
```

```
Asp Asn Ser Leu Thr Asp Arg Leu Val Val Lys Gly Asn Thr Ser Gly
        35                  40                  45

Gln Ser Asp Ile Val Tyr Val Asn Glu Asp Gly Ser Gly Gly Gln Thr
    50                  55                  60

Arg Asp Gly Ile Asn Ile Ile Ser Val Glu Gly Asn Ser Asp Ala Glu
65                  70                  75                  80

Phe Ser Leu Lys Asn Arg Val Val Ala Gly Ala Tyr Asp Tyr Thr Leu
                85                  90                  95

Gln Lys Gly Asn Glu Ser Gly Thr Asp Asn Lys Gly Trp Tyr Leu Thr
            100                 105                 110

Ser His Leu Pro Thr Ser Asp Thr Arg
        115                 120
```

<210> SEQ ID NO 3
<211> LENGTH: 72
<212> TYPE: PRT
<213> ORGANISM: Artificial Sequence
<220> FEATURE:
<223> OTHER INFORMATION: Artificially synthesized peptide sequence

<400> SEQUENCE: 3

```
Gly Thr Ala Ser Ala Leu Ala Ala Ser Gln Leu Pro Gln Ala Thr Met
1               5                   10                  15

Pro Gly Lys Ser Met Val Ala Ile Ala Gly Ser Ser Tyr Gln Gly Gln
            20                  25                  30

Asn Gly Leu Ala Ile Gly Val Ser Arg Ile Ser Asp Asn Gly Lys Val
        35                  40                  45

Ile Ile Arg Leu Ser Gly Thr Thr Asn Ser Gln Gly Lys Thr Gly Val
    50                  55                  60

Ala Ala Gly Val Gly Tyr Gln Trp
65                  70
```

<210> SEQ ID NO 4
<211> LENGTH: 50
<212> TYPE: PRT
<213> ORGANISM: Artificial Sequence
<220> FEATURE:
<223> OTHER INFORMATION: Artificially synthesized peptide sequence

<400> SEQUENCE: 4

```
Asn Val Ala Asn Gly Asp Ile Ser Ala Thr Ser Thr Asp Ala Ile Asn
1               5                   10                  15

Gly Ser Gln Leu Tyr Ala Val Ala Lys Gly Val Thr Asn Leu Ala Gly
            20                  25                  30

Gln Val Asn Asn Leu Glu Gly Lys Val Asn Lys Val Gly Lys Arg Ala
        35                  40                  45

Asp Ala
    50
```

<210> SEQ ID NO 5
<211> LENGTH: 137
<212> TYPE: PRT
<213> ORGANISM: Artificial Sequence
<220> FEATURE:
<223> OTHER INFORMATION: Artificially synthesized peptide sequence

<400> SEQUENCE: 5

```
Ala Ser Leu Trp Asn Trp Phe Asp Ile Thr Asn Trp Leu Trp Tyr Ile
1               5                   10                  15
```

-continued

```
Lys Asn Leu Ile Ala Ile Gly Ile Gly Ala Thr Leu Gly Ala Trp Leu
            20                  25                  30

Arg Trp Val Leu Gly Leu Lys Leu Asn Gly Ala Gly Trp Pro Trp Gly
        35                  40                  45

Thr Leu Thr Ala Asn Leu Val Gly Gly Tyr Leu Ile Gly Val Met Val
    50                  55                  60

Ala Leu Ile Ala Ser His Pro Ser Trp Pro Ala Trp Ile Arg Leu Ala
65                  70                  75                  80

Ala Val Thr Gly Phe Leu Gly Gly Leu Thr Thr Phe Ser Thr Phe Ser
                85                  90                  95

Ala Glu Thr Val Asp Met Leu Cys Arg Gly Val Tyr Ala Thr Ala Ala
            100                 105                 110

Ala Tyr Ala Gly Ala Ser Leu Ala Gly Ser Leu Ala Met Thr Gly Leu
        115                 120                 125

Gly Leu Ala Thr Val Arg Leu Leu Leu
    130                 135


<210> SEQ ID NO 6
<211> LENGTH: 224
<212> TYPE: PRT
<213> ORGANISM: Artificial Sequence
<220> FEATURE:
<223> OTHER INFORMATION: Artificially synthesized peptide sequence

<400> SEQUENCE: 6

Lys Pro His Met Asn Leu Val Val Ile Gly His Val Asp His Gly Lys
1               5                   10                  15

Ser Thr Leu Val Gly His Leu Leu Ala Arg Leu Gly Tyr Ile Glu Trp
            20                  25                  30

Phe Lys Leu Thr Asn Leu Leu His Gln Ala Arg Ala Arg Gly Lys Gly
        35                  40                  45

Ser Phe Gly Phe Ala Trp Ile Leu Asp Lys Met Lys Glu Glu Arg Glu
    50                  55                  60

Arg Gly Ile Thr Ile Asp Leu Thr Phe Met Lys Phe Glu Thr Lys Lys
65                  70                  75                  80

Tyr Val Phe Thr Ile Ile Asp Ala Pro Gly His Arg Asp Phe Val Lys
                85                  90                  95

Asn Met Ile Thr Gly Ala Ser Gln Ala Asp Ala Ala Ile Leu Val Val
            100                 105                 110

Ser Ala Arg Lys Gly Glu Phe Glu Ala Gly Met Ser Thr Glu Gly Gln
        115                 120                 125

Thr Arg Glu His Leu Leu Leu Ala Arg Thr Met Gly Ile Glu Gln Ile
    130                 135                 140

Ile Val Ala Val Asn Lys Met Asp Ala Pro Asp Val Asn Tyr Asp Gln
145                 150                 155                 160

Lys Arg Tyr Glu Phe Val Val Ser Val Leu Lys Lys Phe Met Lys Gly
                165                 170                 175

Leu Gly Tyr Gln Val Asp Lys Ile Pro Phe Ile Pro Val Ser Ala Trp
            180                 185                 190

Lys Gly Asp Asn Leu Ile Glu Arg Ser Pro Asn Met Pro Trp Tyr Asn
        195                 200                 205

Gly Pro Thr Leu Val Glu Ala Leu Asp Gln Leu Gln Pro Pro Ala Lys
    210                 215                 220


<210> SEQ ID NO 7
<211> LENGTH: 179
```

```
<212> TYPE: PRT
<213> ORGANISM: Artificial Sequence
<220> FEATURE:
<223> OTHER INFORMATION: Artificially synthesized peptide sequence

<400> SEQUENCE: 7

Ser Asp Pro Val Arg Gln Tyr Leu His Glu Ile Gly Glu Val Leu Glu
1               5                   10                  15

Leu Asp Lys Trp Ala Glu Leu Gly Ala Ala Ala Lys Val Glu Glu Gly
            20                  25                  30

Met Glu Ala Ile Lys Lys Leu Ser Glu Ala Thr Gly Leu Asp Gln Glu
        35                  40                  45

Leu Ile Arg Glu Val Val Arg Ala Lys Ile Leu Gly Thr Ala Ala Ile
    50                  55                  60

Gln Lys Ile Pro Gly Leu Lys Glu Lys Pro Asp Pro Lys Thr Val Glu
65                  70                  75                  80

Glu Val Asp Gly Lys Leu Lys Ser Leu Pro Lys Glu Leu Lys Arg Tyr
                85                  90                  95

Leu His Ile Ala Arg Glu Gly Glu Ala Ala Arg Gln His Leu Ile Glu
            100                 105                 110

Ala Asn Leu Arg Leu Val Val Ser Ile Ala Lys Lys Tyr Thr Gly Arg
        115                 120                 125

Gly Leu Ser Phe Leu Asp Leu Ile Gln Glu Gly Asn Gln Gly Leu Ile
    130                 135                 140

Arg Ala Val Glu Lys Phe Glu Tyr Lys Arg Gly Phe Ala Phe Ser Thr
145                 150                 155                 160

Tyr Ala Thr Trp Trp Ile Arg Gln Ala Ile Asn Arg Ala Ile Ala Asp
                165                 170                 175

Gln Ala Arg


<210> SEQ ID NO 8
<211> LENGTH: 52
<212> TYPE: DNA
<213> ORGANISM: Artificial Sequence
<220> FEATURE:
<223> OTHER INFORMATION: Artificially synthesized HA-tag encoding
      sequence

<400> SEQUENCE: 8

cctgtcttct tatccatacg atgtaccgga ttacgcggga agacgagtgt ta             52


<210> SEQ ID NO 9
<211> LENGTH: 24
<212> TYPE: PRT
<213> ORGANISM: Artificial Sequence
<220> FEATURE:
<223> OTHER INFORMATION: Artificially synthesized peptide sequence

<400> SEQUENCE: 9

Leu Leu Glu Leu Asp Lys Trp Ala Ser Leu Trp Asn Trp Phe Asp Ile
1               5                   10                  15

Thr Asn Trp Leu Trp Tyr Ile Lys
            20


<210> SEQ ID NO 10
<211> LENGTH: 13
<212> TYPE: PRT
<213> ORGANISM: Artificial Sequence
<220> FEATURE:
<223> OTHER INFORMATION: Artificially synthesized peptide sequence
```

<400> SEQUENCE: 10

Ile Phe Ile Ile Ile Val Gly Ser Leu Ile Gly Leu Arg
1 5 10

<210> SEQ ID NO 11
<211> LENGTH: 87
<212> TYPE: PRT
<213> ORGANISM: Artificial Sequence
<220> FEATURE:
<223> OTHER INFORMATION: Artificially synthesized peptide sequence

<400> SEQUENCE: 11

Leu Leu Glu Leu Asp Lys Trp Ala Ser Leu Trp Asn Trp Phe Asp Ile
1 5 10 15

Thr Asn Trp Leu Trp Tyr Ile Ser Gln Leu Pro Gln Ala Thr Met Pro
20 25 30

Gly Lys Ser Met Val Ala Ile Ala Gly Ser Ser Tyr Gln Gly Gln Asn
35 40 45

Gly Leu Ala Ile Gly Val Ser Arg Ile Ser Asp Asn Gly Lys Val Ile
50 55 60

Ile Arg Leu Ser Gly Thr Thr Asn Ser Gln Gly Lys Thr Gly Val Ala
65 70 75 80

Ala Gly Val Gly Tyr Gln Trp
85

<210> SEQ ID NO 12
<211> LENGTH: 94
<212> TYPE: PRT
<213> ORGANISM: Artificial Sequence
<220> FEATURE:
<223> OTHER INFORMATION: Artificially synthesized peptide sequence

<400> SEQUENCE: 12

Leu Leu Glu Leu Asp Lys Trp Ala Ser Leu Trp Asn Trp Phe Asp Ile
1 5 10 15

Thr Asn Trp Leu Trp Tyr Ile Lys Ile Phe Ile Ile Ile Val Ser Gln
20 25 30

Leu Pro Gln Ala Thr Met Pro Gly Lys Ser Met Val Ala Ile Ala Gly
35 40 45

Ser Ser Tyr Gln Gly Gln Asn Gly Leu Ala Ile Gly Val Ser Arg Ile
50 55 60

Ser Asp Asn Gly Lys Val Ile Ile Arg Leu Ser Gly Thr Thr Asn Ser
65 70 75 80

Gln Gly Lys Thr Gly Val Ala Ala Gly Val Gly Tyr Gln Trp
85 90

<210> SEQ ID NO 13
<211> LENGTH: 101
<212> TYPE: PRT
<213> ORGANISM: Artificial Sequence
<220> FEATURE:
<223> OTHER INFORMATION: Artificially synthesized peptide sequence

<400> SEQUENCE: 13

Leu Leu Glu Leu Asp Lys Trp Ala Ser Leu Trp Asn Trp Phe Asp Ile
1 5 10 15

Thr Asn Trp Leu Trp Tyr Ile Lys Ile Phe Ile Ile Ile Val Gly Ser
20 25 30

Leu Ile Gly Leu Arg Ser Gln Leu Pro Gln Ala Thr Met Pro Gly Lys
35 40 45

-continued

```
Ser Met Val Ala Ile Ala Gly Ser Ser Tyr Gln Gly Gln Asn Gly Leu
    50                  55                  60

Ala Ile Gly Val Ser Arg Ile Ser Asp Asn Gly Lys Val Ile Ile Arg
65                  70                  75                  80

Leu Ser Gly Thr Thr Asn Ser Gln Gly Lys Thr Gly Val Ala Ala Gly
                85                  90                  95

Val Gly Tyr Gln Trp
            100


<210> SEQ ID NO 14
<211> LENGTH: 32
<212> TYPE: PRT
<213> ORGANISM: Artificial Sequence
<220> FEATURE:
<223> OTHER INFORMATION: Artificially synthesized peptide sequence

<400> SEQUENCE: 14

Met Lys Gln Ile Glu Asp Lys Ile Glu Glu Ile Leu Ser Lys Ile Tyr
1               5                   10                  15

His Ile Glu Asn Glu Ile Ala Arg Ile Lys Lys Leu Ile Gly Glu Val
            20                  25                  30


<210> SEQ ID NO 15
<211> LENGTH: 27
<212> TYPE: PRT
<213> ORGANISM: Artificial Sequence
<220> FEATURE:
<223> OTHER INFORMATION: Artificially synthesized timerization domain

<400> SEQUENCE: 15

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25
```

COMPOSITIONS AND METHODS FOR PREVENTING AND TREATING VIRUS INFECTION

CROSS REFERENCE TO RELATED APPLICATIONS

This application is a national stage filing of PCT International Application No. PCT/US2019/048396, filed Aug. 27, 2019, incorporated herein by reference in its entirety, which claims benefit of U.S. Provisional Application Ser. No. 62/723,131, filed Aug. 27, 2018. The disclosure of this Provisional Application is incorporated herein by reference in its entirety.

TECHNICAL FIELD

The presently discsdddlosed subject matter relates to compositions and methods useful for treating and preventing viral infections. In particular, the presently disclosed subject matter relates to vaccines that can be administered to subjects to treat and/or prevent viral infections.

BACKGROUND

An effective vaccine, such as but not limited to an effective HIV vaccine, should induce good humoral and mucosal immunity, eliciting production of broadly neutralizing (BN) antibodies (Abs) capable of protecting against infection by a wide variety of HIV-1 viral strains (Mascola et al., 2010; Mascola et al., 2013; Kwong et al., 2013; U.S. Pat. No. 8,637,036). A vaccine that elicits good cell-mediated immunity would offer additional benefits. Some HIV patients, over time, develop antibodies with broadly neutralizing (BN) activity. These BN antibodies, cannot eliminate HIV infection in the patient, of course, but may help to control the amount of circulating virus in the patient (referred to as the viral load "set point"). Immunologists have produced BN monoclonal antibodies (BNMAbs) from the cells of the patients whose sera have BN activity. Structural biologists have identified antigen binding targets for these BNMAbs, which presently fall into seven classes: (1) the CD4 binding site (McLellan et al, 2011; Zhou et al., 2010; Chen et al., 2009; U.S. Pat. No. 9,493,549); (2) the V1-V2 binding site at the trimer apex (Sok et al., 2014; Doria-Rose et al., 2016; Walker et al., 2009); (3) the V3 glycan site (Walker et al., 2011; Mouquet et al., 2012); (4) a glycan site on the gp120 outer domain (2G12 binding site; Trkola et al., 1996; Buchacher et al., 1994); (5) a region comprising residues from both gp120 and gp41 between the membrane-proximal external region (MPER) and gp120 (Huang et al., 2014; Falkowska et al., 2014); (6) the HIV fusion peptide (Kong et al., 2016; van Gils et al., 2016; U.S. Patent Application Publication No. 2009/0270312); and (7) the membrane-proximal external region (MPER) itself (Zhu et al., 2011; Salzwedel et al. 1999; Morris et al., 2011; Muster et al., 199; Zwick et al., 2001; Zwick et al., 2005; Buzon et al., 2010).

A plausible approach to developing an HIV vaccine would involve production of immunogens resembling epitopes bound by BNAbs, but successful development of such immunogens has been challenging. Making immunogens that mimic epitope shapes from discontinuous protein regions is difficult; making immunogens mimicking complex carbohydrates shapes is even harder. MPER, a highly conserved, linear, and non-glycosylated region consisting of 24 residues at the N-terminus of gp41, represents an appealing target from an engineering perspective (Kwong et al., 2013; Muster et al. 1993).

When MPER was first identified as the target of a class of anti-HW BNMAbs, several teams synthesized the MPER peptide and vaccinated animals with the peptide. These vaccinations produced an immune response, but the antibodies did not interact with and did not neutralize HIV, probably because the isolated MPER peptide, when not in the context of the rest of the envelope molecule, did not assume tertiary and quaternary structures that would elicit neutralizing antibodies capable of targeting the viral envelope protein as it exists in the virion.

There is a need in the art for compositions and methods useful for preventing and treating viral infections such as HIV infection. The presently disclosed subject matter addresses these and other needs in the art.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this summary does not list or suggest all possible combinations of such features.

In some embodiments, the presently disclosed subject matter relates to a modified bacterium, or derivatives thereof, comprising an antigen expressed on a surface of a membrane of the bacterium, wherein the antigen is provided in a conformation resembling a native conformation of the antigen. In some embodiments, the bacterium is a Gram-negative bacterium. In some embodiments, the bacterium is selected from the group consisting of *Salmonella, E. coli, Shigella* sp., *Enterobacter* sp., and other Enterobacteriaceae; *Neisseria* sp., *Moraxella* sp., *Haemophilus* sp., *Klebsiella* sp., *Legionella* sp., *Burkholderia* sp., and *Pseudomonas* sp. In some embodiments, the bacterium is a *Salmonella* or an *E. coli*. In some embodiments, the bacterium comprises a mutation. In some embodiments, the modified bacterium comprises an autotransporter (AT) expression vector encoding the antigen. In some embodiments, the autotransporter expression vector comprises a *Haemophilus influenzae* (Hia) autotransporter expression vector. In some embodiments, the AT expression vector comprises a monomeric vector or a trimeric vector. In some embodiments, the antigen is derived from a microbe, optionally a virus. In some embodiments, the antigen is derived from an enveloped virus. In some embodiments, the antigen is derived from HIV. In some embodiments, the antigen derived from HIV comprises a MPER, a CD4 binding site, a discontinuous V1V2 epitope, and a fusion peptide 1. In some embodiments, the MPER peptide comprises a sequence selected from the group consisting of SEQ ID NOs: 5-7, 9, and 11-13, or a homolog or fragment thereof.

The presently disclosed subject matter also relates in some embodiments to vaccine compositions comprising a modified bacterium as set forth herein; and a pharmaceutically acceptable carrier. The presently disclosed subject matter also relates in some embodiments to vaccine compositions comprising a purified trimeric MPER antigen, optionally wherein the purified trimeric MPER antigen is linked to the surface of a bacterium covalently or non-covalently, further optionally wherein the bacterium is a modified bacterium as disclosed herein; and a pharmaceutically acceptable carrier. The presently disclosed subject matter provides in some embodiments a vaccine composition comprising (a) a modified bacterium a disclosed herein, (b) a purified trimeric MPER antigen, optionally wherein the purified trimeric MPER antigen is linked to the surface of a bacterium covalently or non-covalently, further optionally wherein the bacterium is a modified bacterium as disclosed herein, or (c) a combination of (a) and (b); and a pharmaceutically acceptable carrier. In some embodiments, the modified bacterium is a live attenuated bacterium or a killed whole cell bacterium. In some embodiments, the vaccine composition can elicit a neutralizing immune response in a subject. In some embodiments, the vaccine composition is adapted to be administered orally, rectally, vaginally, intranasally, parenterally, intradermally, subcutaneously, or intramuscularly.

The presently disclosed subject matter also related in some embodiments to methods for producing an antibody. In some embodiments, the methods comprise providing a modified bacterium as set forth herein and administering the modified bacterium to a subject, whereby an antibody is produced in the subject. In some embodiments, the antibody is a neutralizing antibody. In some embodiments, the modified bacterium is provided in a pharmaceutically acceptable carrier. In some embodiments, the modified bacterium is administered orally, rectally, vaginally, intra-nasally, parenterally, intradermally, subcutaneously, or intramuscularly.

The presently disclosed subject matter also related in some embodiments to methods for vaccinating subjects in need of vaccination. In some embodiments, the methods comprise providing a vaccine composition as disclosed herein and administering the vaccine to a subject. In some embodiments, the vaccine composition elicits production of a neutralizing antibody in the subject. In some embodiments, the vaccine composition is administered orally, rectally, vaginally, intra-nasally, parenterally, intradermally, subcutaneously, or intramuscularly. In some embodiments, the vaccine composition is directed against is HIV. In some embodiments, the vaccine composition is administered to a subject at risk of exposure to HIV or as a treatment to a subject infected with HIV.

The presently disclosed subject matter also related in some embodiments to expression vectors comprising a nucleotide sequence encoding an antigen. In some embodiments, the expression vectors are configured to express the antigen in a conformation resembling a native conformation of the antigen and on a surface of a bacterium modified to comprise the expression vector. In some embodiments, the expression vectors comprise an autotransporter (AT) expression vector. In some embodiments, the autotransporter expression vector comprises a *Haemophilus influenzae* (Hia) autotransporter expression vector. In some embodiments, the AT expression vector comprises a monomeric vector or a trimeric vector. In some embodiments, the nucleotide sequence encoding the antigen is positioned under control of an inducible promoter. In some embodiments, the antigen is a MPER peptide, optionally wherein the MPER peptide comprises a sequence selected from the group consisting of SEQ ID NOs: 5-7, 9, and 11-13, or a homolog or fragment thereof. In some embodiments, the antigen is expressed as a monomer or as a trimer. In some embodiments, the MPER peptide comprises a native MPER amino acid sequence expressed as a trimer. In some embodiments, the MPER peptide comprises a modified MPER amino acid sequence expressed as a trimer. In some embodiments, the MPER peptide mimics a native trimeric MPER. In some embodiments, the expression vector is provided in a pharmaceutically acceptable carrier.

Accordingly, it is an object of the presently disclosed subject matter to provide methods and compositions for treating and/or preventing infection by viruses.

This and other objects are achieved in whole or in part by the presently disclosed subject matter. Further, an object of the presently disclosed subject matter having been stated above, other objects and advantages of the presently disclosed subject matter will become apparent to those skilled in the art after a study of the following description, Figures, and EXAMPLES.

BRIEF DESCRIPTION OF THE FIGURES

FIG. 5 shows HIV neutralization results obtained using the TZM-bl assay. The TZM-bl cell line is derived from a HeLa cell clone that was engineered to express CD4, CCR5, and CXCR4 and to contain integrated reporter genes for firefly Luc and *E. coli* β-galactosidase under the control of an HIV-1 long terminal repeat, permitting sensitive and accurate measurements of infection. Sera were obtained from mice following intranasal immunization with $10^8$, then $10^9$, formalin-fixed whole cells. Serial dilutions of sera from mice immunized with bacteria expressing the 3AGJ scaffold MPER on their surfaces (top row) and mice immunized with bacteria not expressing the 3AGJ scaffold on their surfaces (middle row) were used in the TZM-bl HIV (HXB2) neutralization assay. The bottom row shows results from the assay using serial dilutions of the well-described anti-HIV broadly neutralizing MAbs 10E8 and 2F5 as positive controls. The results demonstrated that expressing an MPER-related immunogen on the surface of bacteria could elicit an anti-HIV neutralizing response.

DETAILED DESCRIPTION

Figure 1:
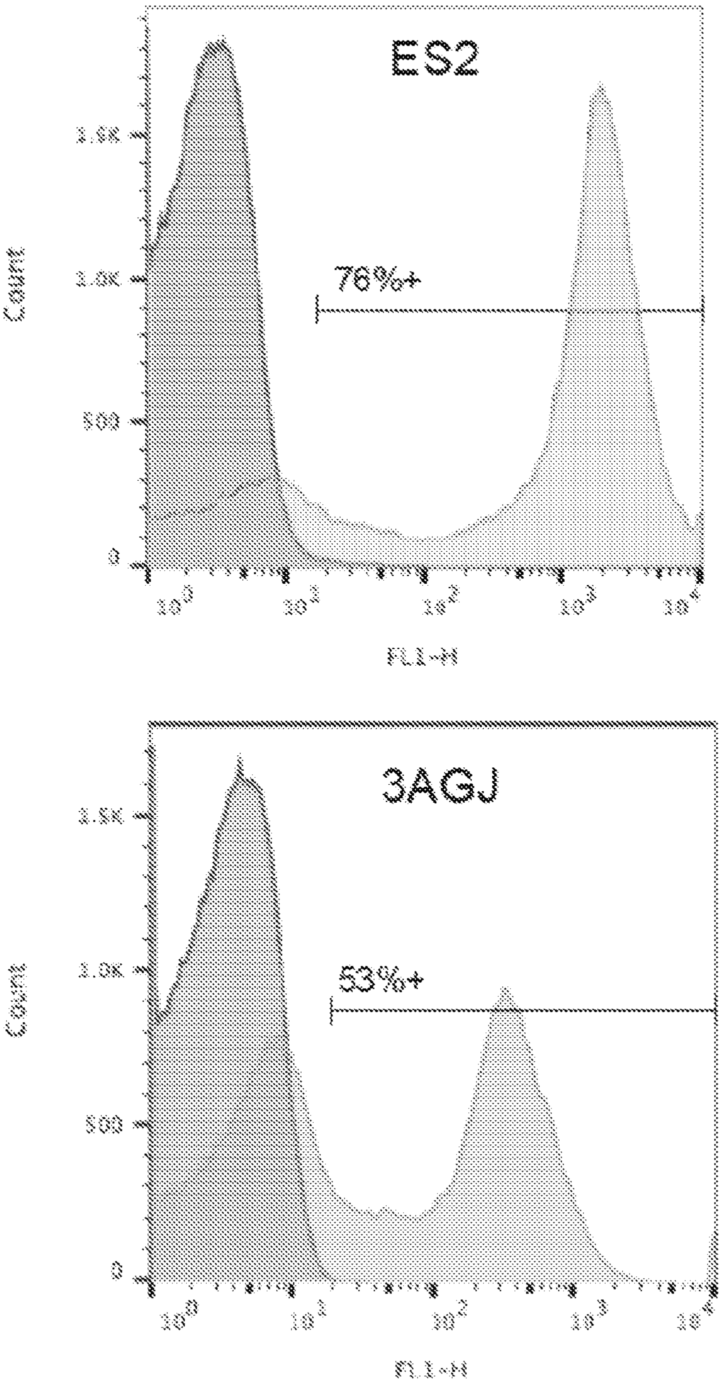
FIG. 1 is a set of plots showing flow cytometry analyses of binding to anti-HIV BN MAbs to scaffold MPER immunogens (see e.g., Kwong et al., 2013) expressed on the surface of a Gram-negative bacterium via an AIDA-I-derived autotransporter expression (AT) cassette. (see Jose et al., 2007; Kramer et al., 2003) As an example of a Gram-negative species of bacteria, *Salmonella* were transformed with plasmids that included rhamnose-inducible versions of an AIDA-I AT surface expression cassette that expressed the two different scaffold MPER proteins, an ES2 MPER scaffold (upper plot) designed to bind the 2F5 BN MAb and the 3AGJ MPER scaffold (lower plot) designed to bind the 10E8 BN MAb (Reichart et al, 2016; Ruja et al., 2016). Expression was induced with an optimized concentration of rhamnose, and then bacteria were exposed to the anti-HIV MPER BNMAbs followed by secondary Ab staining and flow cytometry. Bacteria expressing the MPER-scaffolds (light gray plots) were compared to the untransformed parental bacteria (dark gray plots). The results showed that an AT expression cassette could place two different MPER scaffolds on the bacterial surface so that they were recognized by the anti-HIV BN MAbs that they were designed to bind, indicating that the desired MPER antigen was present on the surfaces of the bacteria in a shape and membrane context sufficiently similar to that of native MPER in the virion envelope so that it was capable of being recognized by the anti-MPER BN MAbs, further indicating that the bacteria that expressed the scaffolded MPER antigens represented effective antigens to elicit anti-MPER immune responses.

Neutralizing antibodies that block infections by enveloped viruses typically target epitopes on viral proteins embedded in the viral envelope lipid bilayer. In some cases, the neutralizing antibodies interact both with a specific protein epitope and the lipid bilayer. Effective vaccines aim to elicit the production of neutralizing antibodies. In accordance with some embodiments of the presently disclosed subject matter, a vaccine is prepared by placing a vaccine epitope close to a lipid bilayer to better elicit the production of antibodies capable of neutralizing the targeted pathogen. Various aspects and embodiments of the presently disclosed subject matter are described in further detail below.

I. Abbreviations and Acronyms

| | |
|---|---|
| Ab | antibody |
| AIDA | adhesin involved in diffuse adherence |
| AT | autotransporter (AT) |
| BN | broadly neutralizing |
| BN monoclonal antibodies | BNMAbs |
| GALT | gut associated lymphoid tissue |
| KWC | killed whole cell |
| MAb | monoclonal antibody |
| MPER | membrane-proximal external region, 24 amino acid residues at the N-terminus of gp41 |
| OM | outer membrane |
| PC | phosphatidyl choline |
| RASV | recombinant attenuated *Salmonella* vector |
| TMD | transmembrane domain |
| TrnAIDA | truncated or shorter AIDA |
| TrnHiaAT | truncated or shorter HiaAT |

II. Definitions

In describing and claiming the presently disclosed subject matter, the following terminology will be used in accordance with the definitions set forth below.

The articles "a" and "an" are used herein to refer to one or to more than one (i.e., to at least one) of the grammatical object of the article. By way of example, "an element" refers to one element or more than one element.

The term "about", as used herein, means approximately, in the region of, roughly, or around. When the term "about" is used in conjunction with a numerical range, it modifies that range by extending the boundaries above and below the numerical values set forth. For example, in some embodiments, the term "about" is used herein to modify a numerical value above and below the stated value by a variance of 20%.

A disease or disorder is "alleviated" if the severity of a symptom of the disease, condition, or disorder, or the frequency at which such a symptom is experienced by a subject, or both, are reduced.

The terms "additional therapeutically active compound" and "additional therapeutic agent", as used in the context of the presently disclosed subject matter, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease, or disorder being treated.

As used herein, the term "adjuvant" refers to a substance that elicits an enhanced immune response when used in combination with a specific antigen.

As use herein, the terms "administration of" and/or "administering" a compound should be understood to refer to providing a compound of the presently disclosed subject matter, or a prodrug and/or precursor of a compound of the presently disclosed subject matter, to a subject in need of treatment.

As used herein, the term "aerosol" refers to suspension in the air. In particular, aerosol refers to the particlization or atomization of a formulation of the presently disclosed subject matter and its suspension in the air.

As used herein, an "analog" of a chemical compound is a compound that, by way of example, resembles another in structure but is not necessarily an isomer (e.g., 5-fluorouracil is an analog of thymine).

As used herein, "amino acids" are represented by the full name thereof, by the three letter code corresponding thereto, or by the one-letter code corresponding thereto, as indicated in the following Table:

| Full Name | 3-Letter Code | 1-Letter Code | Functionally Equivalent Codons |
|---|---|---|---|
| Aspartic Acid | Asp | D | GAC; GAU |
| Glutamic Acid | Glu | E | GAA; GAG |
| Lysine | Lys | K | AAA; AAG |
| Arginine | Arg | R | AGA; AGG; CGA; CGC; CGG; CGU |
| Histidine | His | H | CAC; CAU |
| Tyrosine | Tyr | Y | UAC; UAU |
| Cysteine | Cys | C | UGC; UGU |
| Asparagine | Asn | N | AAC; AAU |
| Glutamine | Gln | Q | CAA; CAG |
| Serine | Ser | S | ACG; AGU; UCA; UCC; UCG; UCU |
| Threonine | Thr | T | ACA; ACC; ACG; ACU |
| Glycine | Gly | G | GGA; GGC; GGG; GGU |
| Alanine | Ala | A | GCA; GCC; GCG; GCU |
| Valine | Val | V | GUA; GUC; GUG; GUU |
| Leucine | Leu | L | UUA; UUG; CUA; CUC; CUG; CUU |
| Isoleucine | Ile | I | AUA; AUC; AUU |
| Methionine | Met | M | AUG |
| Proline | Pro | P | CCA; CCC; CCG; CCU |
| Phenylalanine | Phe | F | UUC; UUU |
| Tryptophan | Trp | W | UGG |

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the presently disclosed subject matter, and particularly at the carboxy- or amino-terminus, can be modified by methylation, amidation, acetylation, and/or substitution with other chemical groups which can change the peptides' circulating half-lives without adversely affecting their activities. Additionally, a disulfide linkage may be present or absent in the peptides of the presently disclosed subject matter.

The term "amino acid" is used interchangeably with "amino acid residue", and may refer to a free amino acid and/or to an amino acid residue of a peptide. It will be apparent from the context in which the term is used whether it refers to a free amino acid or a residue of a peptide.

Amino acids have the following general structure:

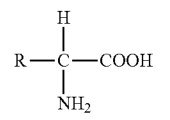

Amino acids may be classified into seven groups on the basis of the side chain R: (1) aliphatic side chains; (2) side chains containing a hydroxylic (OH) group; (3) side chains containing sulfur atoms; (4) side chains containing an acidic or amide group; (5) side chains containing a basic group; (6) side chains containing an aromatic ring; and (7) proline, an imino acid in which the side chain is fused to the amino group.

Synthetic or non-naturally occurring amino acids refer to amino acids which do not naturally occur in vivo but which, nevertheless, can be incorporated into the peptide structures described herein. The resulting "synthetic peptide" contain amino acids other than the 20 naturally occurring, genetically encoded amino acids at one, two, or more positions of the peptides. For instance, naphthylalanine can be substituted for tryptophan to facilitate synthesis. Other synthetic amino acids that can be substituted into peptides include L-hydroxypropyl, L-3,4-dihydroxyphenylalanyl, alpha-amino acids such as L-α-hydroxylysyl and D-α-methylalanyl, L-α-methylalanyl, β-amino acids, and isoquinolyl. D-amino acids and/or non-naturally occurring synthetic amino acids can also be incorporated into the peptides of the presently disclosed subject matter. Other derivatives include replacement of the naturally occurring side chains of the 20 genetically encoded amino acids (or any L- or D- amino acid) with other side chains.

As used herein, the term "conservative amino acid substitution" is defined herein as exchanges within one of the following five groups:

I. Small aliphatic, nonpolar or slightly polar residues:
Ala, Ser, Thr, Pro, Gly;

II. Polar, negatively charged residues and their amides:
Asp, Asn, Glu, Gln;

III. Polar, positively charged residues:
His, Arg, Lys;

IV. Large, aliphatic, nonpolar residues:
Met Leu, Ile, Val, Cys

V. Large, aromatic residues:
Phe, Tyr, Trp

The nomenclature used to describe the peptide compounds of the presently disclosed subject matter follows the conventional practice wherein the amino group is presented to the left and the carboxy group to the right of each amino acid residue. In the formulae representing selected specific embodiments of the presently disclosed subject matter, the amino- and carboxy-terminal groups, although not specifically shown, will be understood to be in the form they would assume at physiologic pH values, unless otherwise specified.

The term "basic" or "positively charged" amino acid, as used herein, refers to amino acids in which the R groups have a net positive charge at pH 7.0, and include, but are not limited to, the standard amino acids lysine, arginine, and histidine.

As used herein, an "analog" of a chemical compound is a compound that, by way of example, resembles another in structure but is not necessarily an isomer (e.g., 5-fluorouracil is an analog of thymine).

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the presently disclosed subject matter may exist in a variety of forms including, for example, polyclonal antibodies, monoclonal antibodies, Fv, Fab and $F(ab)_2$, as well as single chain antibodies and humanized antibodies.

An "antibody heavy chain," as used herein, refers to the larger of the two types of polypeptide chains present in all antibody molecules.

An "antibody light chain," as used herein, refers to the smaller of the two types of polypeptide chains present in all antibody molecules.

The term "synthetic antibody" as used herein, refers to an antibody that is generated using recombinant DNA technology, such as, for example, an antibody expressed by a bacteriophage as described herein. The term should also be construed to refer to an antibody that has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology that is available and well known in the art.

The term "antigen" as used herein refers to a molecule that induces an immune response. This immune response may involve antibody production, the activation of specific immunologically-competent cells, or both. An antigen can be derived, for example, from organisms, subunits of proteins/antigens, killed or inactivated whole cells, or lysates. The term "immunogen" is used interchangeably with "antigen" herein.

The term "antigenic determinant" as used herein refers to that portion of an antigen that makes contact with a particular antibody (i.e., an epitope). When a protein or fragment of a protein or a chemical moiety is used to immunize a host animal, numerous regions of the antigen may induce the production of antibodies that bind specifically to a given region or three-dimensional structure on the protein. These regions or structures are referred to as antigenic determinants. An antigenic determinant may compete with the intact antigen (i.e., the "immunogen" used to elicit the immune response) for binding to an antibody.

The term "antimicrobial agent" as used herein refers to any naturally-occurring, synthetic, or semi-synthetic compound or composition or mixture thereof, which is safe for human or animal use as practiced in the methods of this presently disclosed subject matter, and is effective in killing or substantially inhibiting the growth of microbes. "Antimicrobial" as used herein, includes antibacterial, antifungal, and antiviral agents.

The term "aqueous solution" as used herein can include other ingredients commonly used, such as sodium bicarbonate described herein, and further includes any acid or base solution used to adjust the pH of the aqueous solution while solubilizing a peptide.

The term "binding" refers to the adherence of molecules to one another, such as, but not limited to, enzymes to substrates, ligands to receptors, antibodies to antigens, DNA binding domains of proteins to DNA, and DNA or RNA strands to complementary strands.

"Binding partner", as used herein, refers to a molecule capable of binding to another molecule.

The term "biocompatible", as used herein, refers to a material that does not elicit a substantial detrimental response in the host.

As used herein, the terms "biologically active fragment" and "bioactive fragment" of a peptide encompass natural and synthetic portions of a longer peptide or protein that are capable of specific binding to their natural ligand and/or of performing a desired function of a protein, for example, a fragment of a protein of larger peptide which still contains the epitope of interest and is immunogenic.

The term "biological sample", as used herein, refers to samples obtained from a subject, including but not limited to skin, hair, tissue, blood, plasma, cells, sweat, and urine.

As used herein, the term "carrier molecule" refers to any molecule that is chemically conjugated to an antigen of interest that enables, facilitates, and/induces an immune response (such as but not limited to production of antibodies) that are specific to the antigen.

As used herein, the terms "chemically conjugated" and "conjugating chemically" refer to linking an antigen to a carrier molecule. This linking can occur on the genetic level using recombinant technology, wherein a hybrid protein may be produced containing the amino acid sequences, or portions thereof, of both the antigen and the carrier molecule. This hybrid protein can be produced by an oligonucleotide sequence encoding both the antigen and the carrier molecule, or portions thereof. This linking also includes covalent bonds created between the antigen and the carrier protein using other chemical reactions, such as but not limited to reactions with glutaraldehyde. Covalent bonds may also be created using a third molecule bridging the antigen to the carrier molecule. These cross-linkers are able to react with groups such as but not limited to primary amines, sulfhydryls, carbonyls, carbohydrates, and/or carboxylic acids, on the antigen and the carrier molecule. Chemical conjugation also includes non-covalent linkage between the antigen and the carrier molecule.

A "coding region" of a gene comprises the nucleotide residues of the coding strand of the gene and the nucleotides of the non-coding strand of the gene which are homologous with or complementary to, respectively, the coding region of an mRNA molecule which is produced by transcription of the gene.

The term "competitive sequence" refers to a peptide or a modification, fragment, derivative, or homolog thereof that competes with another peptide for its cognate binding site.

"Complementary" as used herein refers to the broad concept of subunit sequence complementarity between two nucleic acids (e.g., two DNA molecules). When a nucleotide position in both of the molecules is occupied by nucleotides normally capable of base pairing with each other at a given position, the nucleic acids are considered to be complementary to each other at this position. Thus, two nucleic acids are complementary to each other when a substantial number (in some embodiments at least 50%) of corresponding positions in each of the molecules are occupied by nucleotides that can base pair with each other (e.g., A:T and G:C nucleotide pairs). Thus, it is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. By way of example and not limitation, the first region comprises a first portion and the second region comprises a second portion, whereby, when the first and second portions are arranged in an antiparallel fashion, in some embodiments at least about 50%, in some embodiments at least about 75%, in some embodiments at least about 90%, and in some embodiments at least about 95% of the nucleotide residues of the first portion are capable of base pairing with nucleotide residues in the second portion. In some embodiments, all nucleotide residues of the first portion are capable of base pairing with nucleotide residues in the second portion.

A "compound", as used herein, refers to a polypeptide, an isolated nucleic acid, or other agent used in the method of the presently disclosed subject matter.

A "control" cell, tissue, sample, or subject is a cell, tissue, sample, or subject of the same type as a test cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. The control may also be obtained from another source or similar source other than the test group or a test subject, where the test sample is obtained from a subject suspected of having a condition, disease, or disorder for which the test is being performed.

A "test" cell is a cell being examined.

A "pathoindicative" cell is a cell that, when present in a tissue, is an indication that the animal in which the tissue is located (or from which the tissue was obtained) is afflicted with a condition, disease, or disorder.

A "pathogenic" cell is a cell that, when present in a tissue, causes or contributes to a condition, disease, or disorder in the animal in which the tissue is located (or from which the tissue was obtained).

A tissue "normally comprises" a cell if one or more of the cell are present in the tissue in an animal not afflicted with a condition, disease, or disorder.

As used herein, a "derivative" of a bacterium, antigen, composition, or other molecule refers to a bacterium, antigen, composition, or other compound that may be produced from the bacterium, antigen, composition, or other compound of similar structure in one or more steps.

The term "detect" and its grammatical variants refer to measurement of the species without quantification, whereas uses of the words "determine" and "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the detectable marker or reporter molecule in the presence of similar compounds without a detectable marker or reporter molecule. Detectable markers and reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

As used herein, the term "diagnosis" refers to detecting a risk or propensity to a condition, disease, or disorder. In any method of diagnosis exist false positives and false negatives. Any one method of diagnosis does not provide 100% accuracy.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "domain" refers to a part of a molecule or structure that shares common physicochemical features, such as, but not limited to, hydrophobic, polar, globular, and helical domains, and/or properties such as ligand binding, signal transduction, cell penetration, and the like. Specific examples of binding domains include, but are not limited to, DNA binding domains and ATP binding domains.

As used herein, an "effective amount" or "therapeutically effective amount" refers to an amount of a compound or composition sufficient to produce a selected effect, such as but not limited to alleviating symptoms of a condition, disease, or disorder. In the context of administering compounds in the form of a combination, such as multiple compounds, the amount of each compound, when administered in combination with one or more other compounds, may be different from when that compound is administered alone. Thus, an effective amount of a combination of compounds refers collectively to the combination as a whole, although the actual amounts of each compound may vary. The term "more effective" means that the selected effect occurs to a greater extent by one treatment relative to the second treatment to which it is being compared.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA, and mRNA) or a defined sequence of amino acids and the biological properties resulting therefrom. Thus, a gene encodes a protein if transcription and translation of an mRNA corresponding to or derived from that gene produces the protein in a cell or other biological system and/or an in vitro or ex vivo system. Both the coding strand, the nucleotide sequence of which is identical to the mRNA sequence (with the exception of uracil bases presented in the latter) and is usually provided in Sequence Listing, and the non-coding strand, used as the template for transcription of a gene or cDNA, can be referred to as encoding the protein or other product of that gene or cDNA.

An "enhancer" is a DNA regulatory element that can increase the efficiency of transcription, regardless of the distance or orientation of the enhancer relative to the start site of transcription.

The term "epitope" as used herein is defined as a small chemical group on an antigen molecule that can elicit an immune reaction and/or react with an antibody. An antigen can have one or more epitopes. Most antigens have many epitopes; i.e., they are multivalent. In general, an epitope is roughly at least five amino acids or sugars in size. One skilled in the art understands that generally the overall three-dimensional structure, rather than the specific linear sequence of a molecule, is the main criterion of antigenic specificity.

As used herein, an "essentially pure" preparation of a particular protein or peptide is a preparation wherein in some embodiments at least about 95% and in some embodiments at least about 99%, by weight, of the protein or peptide in the preparation is the particular protein or peptide.

A "fragment", "segment", or "subsequence" is a portion of an amino acid sequence, comprising at least one amino acid, or a portion of a nucleic acid sequence comprising at least one nucleotide. The terms "fragment", "segment", and "subsequence" are used interchangeably herein.

As used herein, the term "fragment", as applied to a protein or peptide, can ordinarily be in some embodiments at least about 3-15 amino acids in length, in some embodiments at least about 15-25 amino acids, in some embodiments at least about 25-50 amino acids in length, in some embodiments at least about 50-75 amino acids in length, in some embodiments at least about 75-100 amino acids in length, and in some embodiments greater than 100 amino acids in length.

As used herein, the term "fragment" as applied to a nucleic acid, may ordinarily be in some embodiments at least about 20 nucleotides in length, in some embodiments at least about 50 nucleotides, in some embodiments from about 50 to about 100 nucleotides, in some embodiments at least about 100 to about 200 nucleotides, in some embodiments at least about 200 nucleotides to about 300 nucleotides, in some embodiments at least about 300 to about 350, in some embodiments at least about 350 nucleotides to about 500 nucleotides, in some embodiments at least about 500 to about 600, in some embodiments at least about 600 nucleotides to about 620 nucleotides, in some embodiments at least about 620 to about 650, and in some embodiments the nucleic acid fragment will be greater than about 650 nucleotides in length.

As used herein, a "functional" biological molecule is a biological molecule in a form in which it exhibits a property by which it can be characterized. A functional enzyme, for example, is one that exhibits the characteristic catalytic activity by which the enzyme can be characterized.

As used herein, the term "homologous" refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 5'-ATTGCC-3' and 5'-TATGGC-3' share 50% homology.

As used herein, "homology" is used synonymously with "identity".

The determination of percent identity between two nucleotide or amino acid sequences can be accomplished using a mathematical algorithm. For example, a mathematical algorithm useful for comparing two sequences is the algorithm of Karlin & Altschul, 1990a,b, modified as in Karlin & Altschul, 1993. This algorithm is incorporated into the NBLAST and XBLAST programs of Altschul et al., 1990a,b, and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al., 1997. Alternatively, PSI-Blast or PHI-Blast can be used to perform an iterated search which detects distant relationships between molecules (Altschul et al., 1997) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted. In some embodiments, a percent identity can be calculated over an entire length of one or both sequences, and a percent identity can be calculated over the length of a subsequence of one or both sequences, As used herein, the term "hybridization" is used in reference to the pairing of complementary nucleic acids. Hybridization and the strength of hybridization (i.e., the strength of the association between the nucleic acids) is impacted by such factors as the degree of complementarity between the nucleic acids, stringency of the conditions involved, the length of the formed hybrid, and the G:C ratio within the nucleic acids.

The phrase "immunizing a subject against an antigen" refers to administering to the subject a composition, a protein complex, a DNA encoding a protein complex, an antibody or a DNA encoding an antibody, which elicits an immune response in the subject, and, for example, provides protection to the subject against a disease caused by the antigen or which prevents the function of the antigen.

The term "immunologically active fragments thereof" will generally be understood in the art to refer to a fragment of a polypeptide antigen comprising at least an epitope, which means that the fragment at least comprises 4 or 5 contiguous amino acids from the sequence of the polypeptide antigen.

As used herein, the term "inhaler" refers both to devices for nasal and pulmonary administration of a drug, e.g., in solution, powder, and the like. For example, the term "inhaler" is intended to encompass a propellant driven inhaler, such as is used to administer antihistamine for acute asthma attacks, and plastic spray bottles, such as are used to administer decongestants.

The term "inhibit", as used herein when referring to a particular function or activity, refers to the ability of a compound of the presently disclosed subject matter to reduce or impede the particular function or activity. Inhibition can be in some embodiments by at least 10%, in some embodiments by at least 25%, in some embodiments by at least 50%, and in some embodiments the function is inhibited by at least 75%. When the term "inhibit" is used more generally, such as "inhibit Factor I", it refers to inhibiting expression, levels, and/or activity of Factor I.

The term "inhibit a complex", as used herein, refers to inhibiting the formation of a complex or interaction of two or more proteins, as well as inhibiting a function or activity of the complex. The term also encompasses disrupting a formed complex. However, the term does not imply that each and every one of these functions must be inhibited at the same time or to the same degree.

The term "inhibit a protein", as used herein, refers to any method or technique that inhibits protein synthesis, an expression level, an activity, and/or a function, as well as methods of inhibiting the induction or stimulation of synthesis, expression levels, activities, and/or functions of the protein of interest. The term also refers to any metabolic or regulatory pathway which can regulate the synthesis, level, activity, and/or function of a protein of interest. The term includes binding with other molecules and complex formation. Therefore, the term "protein inhibitor" refers to any agent or compound, the application of which results in the inhibition of a protein function or protein pathway function. However, the term does not imply that each and every one of these functions must be inhibited at the same time or to the same degree.

As used herein "injecting", "applying", and administering" include administration of a compound of the presently disclosed subject matter by any number of routes and modes including, but not limited to, topical, oral, buccal, intravenous, intramuscular, intra-arterial, intramedullary, intrathecal, intraventricular, transdermal, subcutaneous, intraperitoneal, intranasal, enteral, topical, sublingual, vaginal, ophthalmic, pulmonary, vaginal, and rectal approaches.

As used herein, an "instructional material" includes a publication, a recording, a diagram, or any other medium of expression that can be used to communicate the usefulness of and/or a use for a peptide of the presently disclosed subject matter in a kit for effecting alleviation of the various conditions, diseases, or disorders recited herein. Optionally, or alternately, the instructional material may describe one or more methods of alleviating a condition, disease, or disorder in a cell or a tissue of a mammal. The instructional material of the kit of the presently disclosed subject matter may, for example, be affixed to a container which contains the identified compound presently disclosed subject matter or be shipped together with a container which contains the identified compound. Alternatively, the instructional material may be shipped separately from the container with the intention that the instructional material and the compound be used cooperatively by the recipient.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids that have been substantially purified from other components which naturally accompany the nucleic acid it in a cell, e.g., RNA or DNA or proteins. The term therefore includes, for example, a recombinant DNA which is incorporated into a vector, an autonomously replicating plasmid or virus, or the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

As used herein, a "ligand" is a compound that specifically binds to a target compound or molecule. A ligand "specifically binds to" or "is specifically reactive with" a compound when the ligand functions in a binding reaction which is determinative of the presence of the compound in a sample of heterogeneous compounds.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, such as but not limited to through ionic or hydrogen bonds or van der Waals interactions.

The terms "measuring the level of expression" and "determining the level of expression" as used herein refer to any measure or assay which can be used to correlate the results of the assay with the level of expression of a gene or protein of interest. Such assays include measuring the level of mRNA, protein levels, etc. and can be performed by assays such as northern and western blot analyses, binding assays, immunoblots, etc. The level of expression can include rates of expression and can be measured in terms of the actual amount of an mRNA or protein present. Such assays are coupled with processes or systems to store and process information and to help quantify levels, signals, etc. and to digitize the information for use in comparing levels The term "nasal administration" in all its grammatical forms refers to administration of at least one compound of the presently disclosed subject matter through the nasal mucous membranes to the bloodstream for systemic delivery of at least one compound of the presently disclosed subject matter. The advantages of nasal administration for delivery are that it does not require injection using a syringe and needle, it avoids necrosis that can accompany intramuscular administration of drugs, trans-mucosal administration of a drug is highly amenable to self administration, and it introduces antigen to a region of the animal that is rich in lymphoid tissues and cells of the immune system and is adept at identifying potential infectious threats.

The term "nucleic acid" typically refers to large polynucleotides. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

As used herein, the term "nucleic acid" encompasses RNA as well as single and double-stranded DNA and cDNA. Furthermore, the terms, "nucleic acid," "DNA," "RNA" and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the presently disclosed subject matter.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences".

As used herein, the term "nucleic acid" also encompasses RNA as well as single and double-stranded DNA and cDNA. Furthermore, the terms "nucleic acid", "DNA", "RNA", and similar terms also include nucleic acid analogs, e.g., For example, the so-called "peptide nucleic acids", which are known in the art and have peptide bonds instead of phosphodiester bonds in the backbone, are considered within the scope of the presently disclosed subject matter.

The term "nucleic acid construct", as used herein, encompasses DNA and RNA sequences encoding the particular gene or gene fragment desired, whether obtained by genomic or synthetic methods.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "oligonucleotide" typically refers to short polynucleotides, which in some embodiments are no greater than about 50 nucleotides. It will be understood that when a nucleotide sequence is represented by a DNA sequence (i.e., A, T, G, C), this also includes an RNA sequence (i.e., A, U, G, C) in which "U" replaces "T".

By describing two or more polynucleotides as "operably linked" it is meant that a single-stranded or double-stranded nucleic acid comprises the two or more polynucleotides arranged within a nucleic acid molecule in such a manner that at least one of the two or more polynucleotides is able to exert a physiological effect by which it is characterized upon the other. By way of example, a promoter operably linked to the coding region of a gene is able to promote transcription of the coding region.

The term "otherwise identical sample", as used herein, refers to a sample similar to a first sample, that is, it is obtained in the same manner from the same subject from the same tissue or fluid, or it refers a similar sample obtained from a different subject. The term "otherwise identical sample from an unaffected subject" refers to a sample obtained from a subject not known to have the disease or disorder being examined. The sample may of course be a standard sample. By analogy, the term "otherwise identical" can also be used regarding regions or tissues in a subject or in an unaffected subject.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

The term "peptide" typically refers to short polypeptides but when used in the context of a longer amino acid sequence can also refer to a longer polypeptide.

The term "per application" as used herein refers to administration of a drug or compound to a subject.

The term "pharmaceutical composition" refers to a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

"Pharmaceutically acceptable" means physiologically tolerable, for either human or veterinary application. Similarly, "pharmaceutical compositions" include formulations for human and veterinary use.

As used herein, the term "pharmaceutically acceptable carrier" means a chemical composition with which an appropriate compound or derivative can be combined and which, following the combination, can be used to administer the appropriate compound to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

"Plurality" means at least two.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof.

"Synthetic peptides or polypeptides" refers to non-naturally occurring peptides or polypeptides. Synthetic peptides or polypeptides can be synthesized, for example, using an automated polypeptide synthesizer. Various solid phase peptide synthesis methods are known to those of skill in the art.

By "presensitization" is meant pre-administration of at least one innate immune system stimulator prior to challenge with an agent. This is sometimes referred to as induction of tolerance.

The term "prevent", as used herein, means to stop something from happening, or taking advance measures against something possible or probable from happening. In the context of medicine, "prevention" generally refers to action taken to decrease the chance of getting a disease or condition. It is noted that "prevention" need not be absolute, and thus can occur as a matter of degree.

A "preventive" or "prophylactic" treatment is a treatment administered to a subject who does not exhibit signs, or exhibits only early signs, of a condition, disease, or disorder. A prophylactic or preventative treatment is administered for the purpose of decreasing the risk of developing pathology associated with developing the condition, disease, or disorder.

"Primer" refers to a polynucleotide that is capable of specifically hybridizing to a designated polynucleotide template and providing a point of initiation for synthesis of a complementary polynucleotide (e.g., polymerization). Such synthesis occurs when the polynucleotide primer is placed under conditions in which synthesis is induced, e.g., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. In some embodiments, primers can be labeled, e.g., with chromogenic, radioactive, and/or fluorescent moieties and used as detectable moieties.

As used herein, the term "promoter/regulatory sequence" means a nucleic acid sequence which is required for expression of a gene product operably linked to the promoter/regulator sequence. In some embodiments, this sequence may be the core promoter sequence, and in some embodiments, this sequence may also include an enhancer sequence and other regulatory elements which are required for expression of the gene product. The promoter/regulatory sequence may, for example, be one which expresses the gene product in a tissue specific manner.

A "constitutive" promoter is a promoter which drives expression of a gene to which it is operably linked, in a constant manner in a cell. By way of example, promoters which drive expression of cellular housekeeping genes are considered to be constitutive promoters.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a cell substantially only if the cell is a cell of the tissue type corresponding to the promoter.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross & Mienhofer, 1981 for exemplary protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl, and other acceptable groups linked to the terminal carboxyl group through an ester or ether bond.

The term "protein" typically refers to large polypeptides. Conventional notation is used herein to portray polypeptide sequences: the left-hand end of a polypeptide sequence is the amino-terminus; the right-hand end of a polypeptide sequence is the carboxyl-terminus.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process.

A "highly purified" compound as used herein refers to a compound that is in some embodiments greater than 90% pure, that is in some embodiments greater than 95% pure, and that is in some embodiments greater than 98% pure.

"Recombinant polynucleotide" refers to a polynucleotide having sequences that are not generally found joined together in nature. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell". A gene which is expressed in a recombinant host cell wherein the gene comprises a recombinant polynucleotide produces a "recombinant polypeptide".

A "recombinant polypeptide" is one which is produced upon expression of a recombinant polynucleotide, in some embodiments by a recombinant host cell.

As used herein, the term "reporter gene" means a gene, the expression of which can be detected using a known method. By way of example, the *Escherichia coli* lacZ gene may be used as a reporter gene in a medium because expression of the lacZ gene can be detected using known methods by adding the chromogenic substrate o-nitrophenyl-β-galactoside to the medium (Gerhardt et al., 1994).

A "sample", as used herein, refers in some embodiments to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture.

The term "specifically binds to", as used herein, refers to when a compound or ligand functions in a binding reaction or assay conditions which is determinative of the presence of the compound or ligand in a sample of heterogeneous compounds or ligands.

The term "standard", as used herein, refers to something used for comparison. For example, it can be a known standard agent or compound which is administered and used for comparing results when administering a test compound, or it can be a standard parameter or function which is measured to obtain a control value when measuring an effect of an agent or compound on a parameter or function. Standard can also refer to an "internal standard", such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

A "subject" of analysis, diagnosis, or treatment is an animal. Such animals include mammals, in some embodiments, humans.

As used herein, a "subject in need thereof" is a patient, animal, mammal, or human, who will benefit from the method of this presently disclosed subject matter.

As used herein, "substantially homologous amino acid sequences" includes those amino acid sequences which have in some embodiments at least about 95% homology, in some embodiments at least about 96% homology, in some embodiments at least about 97% homology, in some embodiments at least about 98% homology, and in some embodiments at least about 99% or more homology to an amino acid sequence of a reference antibody chain. Amino acid sequence similarity or identity can be computed by using the BLASTP and TBLASTN programs which employ the BLAST (basic local alignment search tool) 2.0.14 algorithm. The default settings used for these programs are suitable for identifying substantially similar amino acid sequences for purposes of the presently disclosed subject matter.

"Substantially homologous nucleic acid sequence" means a nucleic acid sequence corresponding to a reference nucleic acid sequence wherein the corresponding sequence encodes a peptide having substantially the same structure and function as the peptide encoded by the reference nucleic acid sequence; e.g., where only changes in amino acids not significantly affecting the peptide function occur. In some embodiments, the substantially identical nucleic acid sequence encodes the peptide encoded by the reference nucleic acid sequence. The percentage of identity between the substantially similar nucleic acid sequence and the reference nucleic acid sequence is in some embodiments at least about 50%, 65%, 75%, 85%, 95%, 99%, or more. Substantial identity of nucleic acid sequences can be determined by comparing the sequence identity of two sequences, for example by physical/chemical methods (i.e., hybridization) or by sequence alignment via computer algorithm. Suitable nucleic acid hybridization conditions to determine if a nucleotide sequence is substantially similar to a reference nucleotide sequence are: in some embodiments in 7% sodium dodecyl sulfate SDS, 0.5 M $NaPO_4$, 1 mM EDTA at 50° C. with washing in 2× standard saline citrate (SSC), 0.1% SDS at 50° C.; in some embodiments in 7% (SDS), 0.5 M $NaPO_4$, 1 mM EDTA at 50° C. with washing in 1×SSC, 0.1% SDS at 50° C.; in some embodiments in 7% SDS, 0.5 M $NaPO_4$, 1 mM EDTA at 50° C. with washing in 0.5×SSC, 0.1% SDS at 50° C.; and in some embodiments in 7% SDS, 0.5 M $NaPO_4$, 1 mM EDTA at 50° C. with washing in 0.1×SSC, 0.1% SDS at 65° C. Suitable computer algorithms to determine substantial similarity between two nucleic acid sequences include, GCS program package (Devereux et al., 1984), and the BLASTN or FASTA programs (Altschul et al., 1990a,b; Altschul et al., 1997). The default settings provided with these programs are suitable for determining substantial similarity of nucleic acid sequences for purposes of the presently disclosed subject matter.

The term "substantially pure" describes a compound, e.g., a protein or polypeptide, which has been separated from components which naturally accompany it. Typically, a compound is substantially pure when in some embodiments at least 10%, in some embodiments at least 20%, in some embodiments at least 50%, in some embodiments at least 60%, in some embodiments at least 75%, in some embodiments at least 90%, and in some embodiments at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

The term "symptom", as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse, and other observers.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

The term to "treat", as used herein, means an intervention designed to reduce the frequency with which symptoms are experienced by a patient or subject or administering an agent or compound to reduce the frequency with which symptoms are experienced.

By the term "vaccine", as used herein, is meant a composition which when inoculated into a subject has the effect of stimulating an immune response in the subject, which serves to fully or partially protect the subject against a condition, disease or its symptoms. In one aspect, the condition is HIV. The term vaccine encompasses prophylactic as well as therapeutic vaccines. A combination vaccine is one which combines two or more vaccines, or two or more compounds or agents.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer or delivery of nucleic acid to cells, such as, for example, polylysine compounds, liposomes, and the like. Examples of viral vectors include, but are not limited to, adenoviral vectors, adeno-associated virus vectors, retroviral vectors, recombinant viral vectors, and the like. Examples of non-viral vectors include, but are not limited to, liposomes, polyamine derivatives of DNA and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

III. General Considerations

When MPER was first identified as the target of a class of anti-HIV BNMAbs, the MPER peptide was synthesized and used to vaccinate animals. These vaccinations produced an immune response, but the antibodies did not interact with and did not neutralize HIV. This is likely because the isolated MPER peptide did not assume its correct native structure when it was not present in context of the intact trimeric HIV envelope protein.

BNMAbs recognizing MPER, including 4E10, 2F5, and 10E8, have many somatic mutations and a long heavy chain CDR H3, which interacts with cell membranes (Reichart et al., 2016). Although hydrophobic sequences present in CDR H3 are not necessary for antigen recognition, they are required for broad neutralization and high potency (Lu, 2009; Tomaras & Haynes, 2010; Kardani et al., 2016; Rujas et al., 2016; Soto et al., 2016). Lipid bilayer interactions are thought to be needed for MPER neutralizing activity (Lu, 2009; Musich & Robert-Guroff, 2016), an observation that suggests that MPER-containing immunogens should be presented in the context of a lipid bilayer. An MPER-based immunogen, produced and presented in a lipid bilayer, which is inexpensive and easily deployable would make an excellent candidate HIV vaccine. Disclosed herein are novel approaches to making such a vaccine, including a novel way to produce MPER immunogens anchored into a lipid bilayer, the bacterial membrane.

The gp41 domain trimeric HIV envelope protein is anchored into the HIV envelope lipid bilayer. Its structure resembles the structures of other trimeric viral envelope proteins, such as the influenza virus HA stalk (see e.g., U.S. Pat. No. 10,363,301). Interestingly, the structure also resembles the structure of certain trimeric Gram$^-$ autotransporter proteins (Chan et al., 1997; Meng et al., 2006).

A bacterial surface expression system offers a novel way to synthesize and place many MPER-derived immunogens into a lipid bilayer exposed to the immune system: the outer membrane (OM) of Gram$^-$ bacteria. Gram-negative (Gram$^-$) autotransporter (AT) (autodisplay or Type 5 Secretion System) proteins are a protein family from Gram$^-$ bacteria that enable bacteria to place proteins into their outer membranes, with one region anchored in the membrane lipid bilayer and another exposed to the extracellular environment (Zwick et al., 2001; Zwick et al., 2005; Buzon et al., 2010; Burton et al., 2012). AT proteins have 3 key domains: an N-terminal signal sequence that directs protein across the inner membrane, a C-terminal β-barrel domain that intercalates into the Gram$^-$ outer membrane, yielding a pore-like structure; and a central passenger protein domain that transits through the β-barrel pore to be exposed extracellularly, attached to the (3-barrel, which remains anchored in the outer membrane, "displaying" the passenger protein to the extracellular environment. Native passenger protein coding sequence can be replaced with sequence encoding another protein of interest, yielding a recombinant AT protein, displaying the recombinant passenger protein domain to the extracellular environment, anchored in and closely adjacent to the OM lipid bilayer. About $2\times10^5$ recombinant proteins can be placed on the surface of each bacterial cell (Burton et al., 2012). AT expression systems have been used for recombinant vaccine applications, particularly to express pathogen vaccine antigens on the surfaces of *Salmonella* vectors (Wang et al., 2013; Shi et al., 2013; Kong et al., 2013; Kong et al., 2012; Kramer et al., 2003; Jose & Meyer, 2007; Benz & Schmidt, 1992; Grundner et al., 2005; Phogat & Wyatt, 2007; Sanders et al., 2015).

Several different live attenuated *Salmonella* vaccine vectors have been described. Licensed live and killed whole cell *Salmonella* vaccines are currently marketed for human and veterinary use. *Salmonella* and other recombinant vaccines can be produced for less than one dollar per dose, can be delivered orally, and can be lyophilized and reconstituted at time of use without need for a cold chain, making them ideal for use in a global health context. Billions of doses of live *Salmonella* veterinary vaccines are administered annually, so technology for efficient production of live *Salmonella* vaccines is well established.

Killed whole cell bacterial vaccines are also in common use. Killed whole cell vaccines against diseases like Typhoid fever, plague, and cholera have been used for a hundred years or more. Licensed and/or WHO-prequalified killed Gram$^-$ bacterial vaccines for humans exist for cholera and traveler's diarrhea among other diseases. Live attenuated human Gram$^-$ bacterial vaccines, for example for *Salmonella*, also are licensed.

IV. Compositions and Methods

In some embodiments of the presently disclosed subject matter, it is shown that when ATs are used to place MPER derived proteins on the bacterial surface those proteins bind known broadly neutralizing monoclonal antibodies targeting MPER. By way of particular example and not limitation, this is shown for monomeric ATs expressing scaffold MPERs (heterologous proteins that included MPER-derived sequences with structures designed to mimic MPER shapes) on the surfaces of bacteria and for trimeric ATs expressing native MPER peptides on the surfaces of bacteria. It is further shown that when animals are immunized with bacteria that express MPER-derived proteins (both scaffold MPERs expressed using monomeric ATs and trimeric native MPER peptides expressed using trimeric ATs) on their surfaces that the production of sera that bind the MPER-derived proteins on the bacterial surfaces is elicited. It is also shown that the sera elicited by immunizing animals with bacteria expressing MPER-derived proteins on their surfaces neutralize HIV. The data therefore show that expressing MPER-derived proteins on the surfaces of bacteria using ATs yield a vaccine capable of eliciting an immune response required of an HIV vaccine.

While it is not desired to be bound by a particular theory of operation, in some embodiments of the presently disclosed subject matter, ATs are employed for the production of an HIV vaccine by expressing MPER-derived proteins on the surfaces of bacteria because ATs can help promote correct folding of proteins placed on the bacterial surface because the AT β-barrel can have chaperonin-like characteristics. The trimeric ATs, like the *Haemophilus influenzae* Hia autotransporter (Surana et al., 2004; Cotter et al., 2006), trimerizes in forming the bacterial outer membrane-anchored β-barrel and then translocates 3 passenger proteins through the β-barrel's pore simultaneously. As mentioned above, the structure of these trimeric autotransporters strongly resembles the structure of the HIV envelope trimer embedded in the virion envelope (Chan et al., 1997; Meng et al., 2006), suggesting that trimeric ATs may be helpful in engineering an expression system to place MPER peptides onto a bacterial surface in conformations resembling the native trimer.

Thus, aspects of the presently disclosed subject matter involve placing HIV MPER envelope antigens, both monomeric scaffold MPER antigens using a monomeric autotransporter and native MPER peptide using a trimeric autotransporter (and by extension other similar antigens from other enveloped viruses, like influenza) on the surfaces of Gram-negative bacteria, produced as an antigen that binds the appropriate anti-HIV broadly neutral monoclonal antibody, indicating that the correct immunogenic structure exists on the surfaces of the bacteria. Immunizing a subject with such modified bacteria causes the subject to make antibodies that bind to the desired structure and neutralize the pathogen, like HIV. This means that the bacteria can be used as a vaccine.

Provided in accordance with some embodiments of the presently disclosed subject matter is a modified bacterium comprising an antigen expressed on a surface of a membrane of the bacterium adjacent to a lipid bilayer of the membrane. In some embodiments, the antigen is heterologous with respect to the bacteria. In some embodiments, wherein the antigen is provided in a conformation resembling a native conformation of the antigen. In some embodiments the antigen is modified to satisfy engineering and clinical goals, such as ease of production, enhanced immunogenicity, or decreased toxicity or reactogenicity. In addition, derivatives of the modified bacterium, such as bacterial fragments, vesicles, minicells, blebs, ghost cells, etc, can be used, wherein the antigen is expressed on a surface of the derivative.

In some embodiments, the bacterium is a Gram-negative bacterium. In some embodiments, the bacterium is selected from the group consisting of *Salmonella, E. coli, Shigella* sp, *Enterobacter* sp, and other Enterobacteriaceae; *Neisseria* sp, *Moraxella* sp, *Haemophilus* sp., *Klebsiella* sp, *Legionella* sp, *Burkholderia* sp, and *Pseudomonas* sp. Representative non-limiting example is a recombinant attenuated, *Salmonella*, or attenuated *Salmonella* vaccine strains, including attenuated human and veterinary vaccines. In some embodiments, the modified bacterium is modified to have an attenuated pathogenic phenotype. In some embodiments, the bacterium is a Gram-positive bacteria, modified by a vector other the type 5 secretion system autotransporter, such as but not limited to a staphylococcal protein A surface display system, which is a representative example of an N-terminal fusion method. (See Lee et al., 2003; PCT Publication No. WO9709437, U.S. Pat. No. 5,616,686, PCT Publication No. WO9318163, U.S. Pat. No. 5,958,736, PCT Publication No. WO9640943, and U.S. Pat. No. 5,821,088).

In some embodiments, the bacteria have mutations or include gains of function that enhance immunogenicity, such as the expression of additional molecules that interact with Toll-like receptors or in other ways enhance interactions with phagocytes or lymphocytes to promote a stronger immune response. In some embodiments, the bacteria have loss of function mutations in genes that encode for products that mediate reactogenicity, such as LPS synthesis. In some embodiments, the bacteria have mutations or deletions of genes that blunt the immune response, such as antiphagocytic proteins. In some embodiments, the bacteria have multiple mutations in several genes that affect the immune response or the presentation of antigens in or on the bacteria. In some embodiments, the bacteria have large scale mutations or deletions such that the bacteria have a substantially reduced set of genes, up to the limits of bacterial cell viability.

In some embodiments, the modified bacterium comprises an autotransporter (AT) expression vector encoding the antigen. In some embodiments, the autotransporter expression vector comprises monomeric autotransporter, such as the AIDA-I autotransporter. In some embodiments, the autotransporter expression vector comprises a trimeric autotransporter, such as the *Haemophilus influenzae* (Hia) autotransporter. In some embodiments, the AT expression vector encompasses other classes of autotransporters. In some embodiments, the expression vector places the antigen into outer member using other classes of transporter proteins, other than the autotransporters of the Type 5 class of secretion systems. In some embodiments, the antigen is attached to or associated with the membrane by other approaches, such as covalent or non-covalent coupling to surface molecules, or by association with a receptor, for example biotin and avidin.

In some embodiments, the heterologous antigen is derived from a microbe, optionally a virus. In some embodiments, the heterologous antigen is derived from an enveloped virus. In some embodiments, the heterologous antigen is derived from HIV. In some embodiments, the heterologous antigen derived from HIV comprises a MPER, a CD4 binding site, a discontinuous V1V2 epitope, or a fusion peptide. In some representative, non-limiting embodiments, the MPER peptide comprises a sequence selected from the group consisting of SEQ ID NOs: 5-7, 9, and 11-13, or a homolog or fragment thereof. In some embodiments, the antigen is derived from the envelope or virion protein of any enveloped or non-enveloped virus.

While representative amino acids sequences are disclosed herein (e.g., monomeric scaffold MPER and trimeric native MPER), the presently disclosed subject matter is not limited to these representative sequences. Any suitable amino acid sequence of a desired antigen or nucleotide sequence encoding the same or encoding a molecule to which a broadly neutralizing monoclonal antibody can bind can be employed in the presently disclosed subject matter. Also, depending on the bacterial species and strain used to produce the antigen, it may be helpful to codon optimize for that species/strain.

Trimerization domains are used in some but not all embodiments. By way of example and not limitation, a GCN4 trimerization domain is employed. An exemplary GCN4 trimerization domain comprises the amino acid sequence GYIPEAPRDGQAYVRKDGEWVLLSTFL (SEQ ID NO: 15), although other suitable trimerization domains can be employed, as would be apparent to one of ordinary skill in the art upon a review of the instant disclosure. See PCT International Patent Application Publication No. WO 2019/097466 for examples of trimerization domains that can be employed in the compositions and methods of the presently disclosed subject matter.

The presently disclosed subject matter also provides for the use of other types of promoters as disclosed herein or the use of other promoters known in the art, including constitutive promoters and inducible promoters. In some embodiments, a useful promoter of the presently disclosed subject matter is active only under selected physiologic conditions or particular body compartments. Promoters could, for example, include promoters induced by nutritional substrates, such as the beta-gal or rhamnose promoters.

The presently disclosed subject matter also provides a vaccine composition comprising a modified bacterium as disclosed herein and a pharmaceutically acceptable carrier. In some embodiments, the modified bacterium is a live attenuated bacterium or a killed whole cell bacterium. The presently disclosed subject matter also provides a vaccine composition comprising a purified trimeric MPER antigen and a pharmaceutically acceptable carrier, wherein in some embodiments purified trimeric MPER antigen(s) is/are linked to the surface of the bacterium covalently or non-covalently. The presently disclosed subject matter provides in some embodiments a vaccine composition comprising (a)

a modified bacterium a disclosed herein, (b) a purified trimeric MPER antigen, optionally wherein the purified trimeric MPER antigen is linked to the surface of a bacterium covalently or non-covalently, further optionally wherein the bacterium is a modified bacterium as disclosed herein, or (c) a combination of (a) and (b); and a pharmaceutically acceptable carrier.

In some embodiments, the purified trimeric MPER antigen is produced in bacteria using an autotransporter expression cassette. In some embodiments, additional adjuvants are added to the bacteria prior to immunization, such as cholera toxin B subunit. In some embodiments, the bacteria are fixed with formalin. In some embodiments, the bacteria are fixed with other inactivating agents, such as glutaraldehyde. In some embodiments, the vaccine composition can elicit a neutralizing immune response in a subject. In some embodiments, the vaccine composition is adapted to be administered orally, rectally, vaginally, intra-nasally, parenterally, dermally, intradermally, subcutaneously, or intramuscularly.

In some embodiments, subjects are immunized with a single antigen. In some embodiments, subjects are immunized with two or more antigens targeting the same pathogen molecule. In some embodiments, subjects are immunized with two or more antigens targeting different pathogen molecules or different regions of the same pathogen molecule.

In some embodiments, the antigens are purified or separated from whole intact bacterial cells. In some embodiments the antigens are produced in derivatives of the cell, such as minicells, vesicles (including outer membrane vesicles), blebs, or ghost cells.

In some embodiments of the presently disclosed subject matter, a method of producing an antibody is provided. In some embodiments, the method comprises providing a modified bacterium of the presently disclosed subject matter to a subject, whereby an antibody is produced in the subject. In some embodiments, the antibody is a neutralizing antibody. In some embodiments, the modified bacterium is provided in a pharmaceutically acceptable carrier. In some embodiments, the modified bacterium is administered orally, rectally, vaginally, intra-nasally, parenterally, dermally, intradermally, subcutaneously, or intramuscularly.

In some embodiments of the presently disclosed subject matter, a method of producing a cell-mediated immune response is provided. In some embodiments, the method comprises providing a modified bacterium of the presently disclosed subject matter to a subject, whereby a cell-mediated immune response is produced in the subject. In some embodiments, the modified bacterium is provided in a pharmaceutically acceptable carrier. In some embodiments, the modified bacterium is administered orally, rectally, vaginally, intra-nasally, parenterally, dermally, intradermally, subcutaneously, or intramuscularly.

In some embodiments of the presently disclosed subject matter, a method of vaccinating a subject in need of vaccination is provided. In some embodiments, the method comprises providing a vaccine composition according to the presently disclosed subject matter and administering the vaccine to a subject. In some embodiments, the vaccine composition elicits production of a neutralizing antibody in the subject. In some embodiments, the vaccine composition is administered orally, rectally, vaginally, intra-nasally, parenterally, dermally, intradermally, subcutaneously, or intramuscularly.

In some embodiments, the vaccine composition is directed against is HW. In some embodiments, the vaccine composition is administered to a subject at risk of exposure to HIV or as a treatment to a subject infected with HIV. In some embodiments, the presently disclosed subject matter provides a vaccine for preventing or treating HIV infection. In some embodiments, the vaccine can elicit a neutralizing anti-HIV immune response when used to immunize a subject with a construct of the presently disclosed subject matter. The constructs that are prepared for use to elicit an immunogenic response as a vaccine are, for example, useful for inducing a broad immunogenic response. The compositions and methods of the presently disclosed subject matter are useful against multiple strains of HIV. In some embodiments, the presently disclosed subject matter provides compositions and methods for preventing and treating HIV. In some embodiments, the presently disclosed subject matter provides compositions and methods for preventing sexual transmission of HIV.

In some embodiments, the presently disclosed subject matter provides an inexpensive bacterial vaccine that can be orally delivered. In some embodiments, it is delivered intra-nasally, and in another aspect as described below. In some embodiments, the vaccine elicits a broadly neutralizing anti-MPER immune response. In some embodiments, more than one HIV MPER-related or other HIV antigen can be expressed on the bacterial surface. In some embodiments the immune response is directed against another HIV component that is the target of a broadly neutralizing immune response or antibody.

In some embodiments, a vaccine bacterial construct of the presently disclosed subject matter induces humoral immunity when administered to a subject. In some embodiments, a vaccine of the presently disclosed subject matter induces mucosal immunity when administered to a subject. In some embodiments, a vaccine of the presently disclosed subject matter induces cellular immunity when administered to a subject. In some embodiments, a vaccine of the presently disclosed subject matter induces humoral, mucosal, and cellular immunities when administered to a subject.

In some embodiments, the compositions and methods of the presently disclosed subject matter are useful for neutralizing HIV. In some embodiments, HIV-neutralizing activity is elicited in a subject following immunization of the subject with a vaccine of the presently disclosed subject matter. In some embodiments, the compositions and methods disclosed herein are useful for treating a subject already infected with HIV.

The present application provides compositions and methods for constructs and vectors for vaccines useful against viruses other than HIV, including, but not limited to, influenza, and other enveloped viruses, and also provides compositions and methods for constructs and vectors for vaccines useful against other microbial pathogens whose surface proteins are the targets of important neutralizing immune responses. In some embodiments, a vaccine of the presently disclosed subject matter elicits production of broadly neutralizing antibodies.

In some embodiments, the composition and methods are used to produce a vaccine designed to elicit an immune response in humans. In some embodiments the composition and methods are used to produce a vaccine designed to elicit an immune response in animals, to prevent or treat animal infections.

In some embodiments, an expression vector comprising a nucleotide sequence encoding an antigen (such as but not limited to a MPER peptide) is provided according to the presently disclosed subject matter. In some embodiments, the expression vector is configured to express the antigen (such as but not limited to a MPER peptide) in a conformation resembling a native conformation of the antigen (such as but not limited to a MPER peptide) and on a surface of a bacterium modified to comprise the expression vector. In some embodiments, the antigen is heterologous with respect to the bacterium. The presently disclosed subject matter provides various sequences as well as fragments and homologs thereof that can be used in the expression cassettes. The expression vector comprises a suitable promoter operably linked to the nucleotide sequence and can comprise other desired sequences, such as enhancers and the like. Promoters could, for example, include promoters induced by nutritional substrates, such as the beta-gal or rhamnose promoters.

In some embodiments, the expression vector comprises an autotransporter (AT) expression vector. In some embodiments, the autotransporter expression vector comprises a *Haemophilus influenzae* (Hia) autotransporter expression vector. In some embodiments, the AT expression vector comprises a monomeric vector or a trimeric vector.

In some embodiments of an expression vector of the presently disclosed subject matter, the nucleotide sequence encoding the antigen (such as but not limited to a MPER peptide) is positioned under control of an inducible promoter. In some embodiments, the MPER peptide comprises a sequence selected from the group consisting of SEQ ID NOs: 5-7, 9, and 11-13, or a homolog or fragment thereof. In some embodiments, the antigen (such as but not limited to a MPER peptide) is expressed as a monomer or as a trimer. In some embodiments, the MPER peptide comprises a native MPER amino acid sequence expressed as a trimer. In some embodiments, the MPER peptide comprises a modified MPER amino acid sequence expressed as a trimer. In some embodiments, the MPER peptide mimics a native trimeric MPER. In some embodiments, the expression vector is provided in a pharmaceutically acceptable carrier.

Thus, disclosed herein are expression vectors comprising plasmids employing several variations of MPER peptide expressed on the surface of the bacterial cell using the Hia trimeric AT (see below). Disclosed herein are flow cytometric data showing that when a 24 amino acid MPER sequence was expressed on the cell surface using the Hia AT expression cassette, the surface-expressed MPER peptide is bound by three distinct anti-HIV MPER BNMAbs. This suggests that when using the Hia autotransporter to place MPER on the bacterial surface that the resulting structure closely resembles the structure of the native MPER in the virion envelope. The results disclosed herein using trimeric AT were unexpected.

In some embodiments, the presently disclosed subject matter provides a system expressing MPER on bacterial surfaces via the Hia trimeric autotransporter either as a live attenuated *Salmonella* vaccine or other live recombinant bacterial vaccine or by making a killed whole cell vaccine from the bacteria, or by using purified trimeric protein MPER antigen from the bacteria.

In some embodiments, the presently disclosed subject matter provides compositions and methods for use of bacterial surface expression of the monomeric scaffold as disclosed herein.

In some embodiments, the presently disclosed subject matter addresses several problems in the art, including, but not limited to: (1) presenting antigens that are binding targets of HIV BNMabs directly to the immune system; (2) placing MPER antigen on the exterior of a cell, embedded in a lipid bilayer, thereby presenting an antigen in a context that resembles the native configuration in the viral envelope; (3) providing tightly coupled synthesis and AT-mediated surface export to address previous problems of aggregate formation with MPER-derived proteins made in bacteria and mammalian cells; and (4) providing effective yet inexpensive compositions, i.e., bacteria are inexpensive to grow, easy to transport when lyophilized, and highly immunogenic, serving as their own adjuvants. Vaccines encompassed by the presently disclosed subject matter include recombinant live Gram-negative bacteria and killed whole cells (KWC).

In some embodiments, the presently disclosed subject matter provides an MPER construct useful for inducing an immunogenic response. In some embodiments, it is administered to a subject as a vaccine composition useful for preventing an HIV infection. In some embodiments, it is administered as a treatment to a subject infected with HIV. In some embodiments, the presently disclosed subject matter provides a pharmaceutical composition comprising an MPER construct useful as a vaccine for HIV. In some embodiments, the presently disclosed subject matter provides a pharmaceutical composition comprising an MPER construct useful for treating HIV. In some embodiments, the compositions comprise a bacterium comprising the MPER construct. In some embodiments, bacteria of the presently disclosed subject matter comprise an MPER construct that produces an MPER-derived protein. In some embodiments, the presently disclosed subject matter provides a recombinant bacterial vaccine comprising an MPER useful for preventing and treating HIV infection. In some embodiments, use of bacterial vaccine produces surface MPER.

In some embodiments, the presently disclosed subject matter provides a MPER having a sequence as disclosed herein, or a homolog thereof that elicits the same immunogenic response. In some embodiments, the presently disclosed subject matter provides modified MPERs. In some embodiments, the modified MPERs have been fitted to a monomeric autotransporter to enable surface expression on the bacteria. In some embodiments, the Gram-negative bacteria are *E. coli*. In some embodiments, the presently disclosed subject matter encompasses the use of other Gram-negative bacteria.

In some embodiments, the presently disclosed subject matter provides a MPER that is a scaffold protein. In some embodiments, an AVER sequence or active fragment or homolog thereof is used. See for example, SEQ ID NOs: 5-7, 9, and 11-13. In some embodiments, an MPER sequence or active fragment or homolog thereof can be used as part of a larger protein scaffold. In some embodiments, the larger protein scaffold comprises an MPER-derived sequence or active fragment or homolog thereof. In some embodiments, the MPER scaffold mimics an MPER-like tertiary structure. In some embodiments, the MPER-derived sequence includes MPER-derived amino acids present within a heterologous protein scaffold such that the scaffold-MPER protein mimics an MPER-like tertiary structure. In some embodiments, the MPER mimics a native trimeric MPER. In some embodiments, the MPER-derived protein is native MPER amino acid sequences expressed as a trimer. In one aspect, the MPER-derived protein is native MPER amino acid sequences expressed as a trimer via a trimeric $Gram^-$ autotransporter. In some embodiments, the MPER-derived protein is modified MPER amino acid sequences expressed as a trimer via a trimeric $Gram^-$ autotransporter. In some embodiments, the MPER-derived protein comprises amino acid sequences that have been selected to resemble the three dimensional structure of MPER expressed as a trimer via a trimeric $Gram^-$ autotransporter.

In some embodiments, a pharmaceutical composition comprising one or more components of the presently disclosed subject matter is administered orally. In one aspect, it is administered intra-nasally, rectally, vaginally, parenterally, employing intradermal, subcutaneously, or intramuscularly. In some embodiments, the pharmaceutical composition is a vaccine.

In some embodiments, the presently disclosed subject matter provides for the production of native MPER on the surface of bacteria using a trimeric autotransporter.

In some embodiments, the presently disclosed subject matter provides compositions and methods where HIV MPER-related antigens can be expressed on bacterial surfaces such that the antigens are recognized by their cognate BNMAbs, that immunization with bacteria expressing HIV MPER-related antigens elicits an immune response in sera, vaginal washes, the gastrointestinal tract, or in other mucosal components that bind bacterial surfaces expressing MPER-derived antigens, and that elicited sera have HIV neutralizing activity. In addition, the presence of non-immunogen proteins in the outer membrane (OM) do not appear to block the induction of a neutralizing immune response. The data suggest that the bacterial surface expression of MPER-related antigens represents a highly novel, but plausible approach for HIV vaccine development. That is, it is disclosed herein that immunization with bacteria expressing MPER-derived proteins on their surfaces can elicit HIV neutralizing immune responses as demonstrated, for example, in vivo by immunizing mice with an *E. coli* KWC vaccine expressing the 3AGJ scaffold MPER on their surfaces.

The presently disclosed subject matter provides compositions and methods to produce HIV-1 vaccine candidates employing MPER-derived proteins placed on the bacterial surface using AT expression cassettes, methods to test and evaluate the ability of the vaccines to elicit production of MPER-specific neutralizing sera, methods to produce and evaluate recombinant attenuated *Salmonella* vector (RASV) vaccines surface-expressing MPER-derived immunogens, and methods to test the ability of the candidate vaccines to block transmission in a humanized mouse model. Disclosed herein are unexpectedly good results in experiments constructing and using vaccines where MPER-derived proteins were placed on the bacterial surface using AT expression cassettes.

In some embodiments, the presently disclosed subject matter provides the Hia AT to place MPER peptides (see for example, SEQ ID NOs: 5-7, 9, and 11-13), or other immunogenic peptides, or active homologs or fragments thereof, on the surface of bacteria. In some embodiments, the peptides are recombinant. In some embodiments, the MPER is monomeric. In some embodiments, the MPER is trimeric.

In addition to HIV MPER, the compositions and methods of the presently disclosed subject matter are also useful for other proteins recognized by BNMABs, including the CD4 binding site, discontinuous V1V2 epitopes (quaternary antibody binding regions), and the fusion peptide 1.

The system can also be used to express other viral proteins on the surface of bacteria to be used for immunization or treatment directed against the other viral proteins.

As disclosed herein, the placement of viral envelope antigens, targets of BN immune responses, anchored and close to a lipid bilayer, as with the Gram$^-$ autotransporters will help in eliciting a desired anti-envelope protein neutralizing immune responses, particularly when the known neutralizing antibodies interact both with the protein epitope and the lipid bilayer of the virion envelope.

The presently disclosed subject matter provides a series of proteins or peptides and systems to produce or express those peptides in the context of cell structures, such as a lipid bilayer and other membrane structures found to have immunogenic activity that can be used singly or in combination to elicit an immunogenic response and are useful for preventing and treating HIV, other viral infections, and microbial infections. The presently disclosed subject matter could also be used to produce immunizing antigens targeting the conserved regions of other virion envelope proteins, for or example, a universal influenza vaccine.

In some embodiments, the presently disclosed subject matter provides a set of peptides that can be used together as a cocktail or individually as a component of a vaccine (immunogen) to prevent or to treat HIV. When administered, the cocktail or combination of peptides elicits an immunogenic response. The presently disclosed subject matter further encompasses the use of biologically active homologues of the peptides and wells as biologically active fragments of the peptides. The homologues can, for example, comprise one of more conservative amino acid substitutions, additions, or deletions.

In some embodiments, the presently disclosed subject matter provides an immunogenic vaccine composition for use in treating and preventing HIV. In some embodiments, the composition comprises at least one isolated peptide selected from the group of peptides disclosed herein, or biologically active fragments or homologs thereof. In some embodiments, the immunogenic vaccine composition is a system comprising a viral peptide expressed on the surface of a bacteria. The vaccine composition can also include an adjuvant or a pharmaceutically acceptable carrier. In one aspect, at least two peptides are included in the composition. Any combination of the peptides can be used.

In some embodiments, an immunogenic fragment or homolog of a peptide of the presently disclosed subject matter is used. In some embodiments, the biologically active fragments or homologs of the peptide share at least about 50% sequence identity with the peptide. In some embodiments, they share at least about 75% sequence identity with the peptide. In some embodiments, they share at least about 95% sequence identity with the peptide.

In some embodiments, at least one of the active fragments or homologs being used comprises a serine or alanine amino acid substitution for a cysteine residue. In some embodiments, at least one of the active fragments or homologs being used comprises at least one conservative amino acid substitution. The presently disclosed subject matter encompasses the use of amino acid substitutions at any of the positions, as long as the resulting peptide maintains the desired biologic activity of being immunogenic. The presently disclosed subject matter further includes the peptides where amino acids have been deleted or inserted, as long as the resulting peptide maintains the desired biologic activity of being immunogenic.

In some embodiments, the methods of the presently disclosed subject matter provide for administering the vaccine composition to a subject at least about 2 times to about 50 times. In some embodiments, the method comprises administering the vaccine composition to a subject at least about 5 times to about 30 times. In some embodiments, the methods of the presently disclosed subject matter provide for administering the vaccine composition to a subject at least about 10 times to about 20 times. The method also provides for administering the composition daily, weekly, or monthly. One of ordinary skill in the art can design a regimen based on the needs of a subject, taking into account the age, sex, and health of the subject.

As described herein, the peptides are immunogenic, so a useful composition comprising one or more of the peptides of the presently disclosed subject matter, even when using active fragments or homologs, or additionally short peptides, elicits an immunogenic response.

In some embodiments, a homolog of a peptide of the presently disclosed subject matter is one with one or more amino acid substitutions, deletions, or additions, and with the sequence identities described herein. In some embodiments, the substitution, deletion, or addition is conservative. In some embodiments, a serine or an alanine is substituted for a cysteine residue in a peptide of the presently disclosed subject matter.

In some embodiments, the subject is a mammal. In some embodiments, the mammal is a human.

The presently disclosed subject matter encompasses the use of purified isolated, recombinant, and synthetic peptides.

The presently disclosed subject matter further provides methods for producing peptides which are not easily soluble in an aqueous solution, by immediately expressing the peptides on the surface of the bacteria.

The methods and compositions of the presently disclosed subject matter encompass multiple regimens and dosages for administering the peptides of the presently disclosed subject matter for use in preventing and treating HIV and other diseases and disorders caused by infectious agents. For example, a subject can be administered a combination of peptides, such as a combination of peptides on a bacterium, or a combination of bacteria expressing different peptides, of the presently disclosed subject matter once or more than once. The frequency and number of doses can vary based on many parameters, including the age, sex, and health of the subject. In some embodiments, up to 50 doses are administered. In some embodiments, up to 40 doses are administered, and in some embodiments up to 30 doses are administered. In some embodiments, up to 20 doses are administered, and in some embodiments up to 10 doses are administered. In some embodiments, 5-10 doses are administered. In some embodiments, 5, 6, 7, 8, 9, or 10 doses can be administered.

In some embodiments, a peptide, or two or more peptides, and/or bacteria expressing a peptide, and/or bacteria expressing two or more peptides are administered daily, in some embodiments weekly, and in some embodiments monthly. Treatment periods may be for a few days, or about a week, or about several weeks, or for several months. Follow-up administration or boosters can be used as well and the timing of that can be varied.

The amount of peptide and/or bacteria expressing a peptide or derivative of the bacteria administered per dose can vary as well. For example, in some embodiments, the compositions and methods of the presently disclosed subject matter include a range of peptide amounts (for example as provided by bacteria expressing a peptide) between about 10 micrograms of each peptide per dose to about 10,000 micrograms of peptide per dose. In some embodiments, the number of micrograms is the same for each peptide. In some embodiments, the number of micrograms is not the same for each peptide. In some embodiments, the range of amounts of each peptide administered per dose is from about 20 micrograms to about 1,000 micrograms. In some embodiments, it is from about 50 micrograms to about 500 micrograms. In some embodiments, it is from about 75 micrograms to about 400 micrograms. In some embodiments, it is from about 100 micrograms to about 300 micrograms, and in some embodiments from about 150 micrograms to about 250 micrograms. In some embodiments, about 300 micrograms of each peptide is used per dose per treatment. The number of bacteria administered can be varied over a large range, from $10^4$ to $10^{10}$ cells. The doses of the peptide and/or cells can also be varied from one administration to the next, to elicit the most useful immune responses.

Subjects can be monitored before and after bacteria and/or peptide administration for antibody levels against the peptides being administered (for example as provided by bacteria expressing a peptide) and by monitoring T cell responses, including CD4+ and CD8+. Methods for these tests are routinely used in the art and are either described herein or, for example, in publications cited herein.

Although a vaccine composition construct, bacteria, mixture of bacteria, derivatives thereof, or cocktail of peptides or a combination therefor is described herein, when more than one bacterial construct or peptide is administered, each different bacterial construct or peptide can be administered separately. When a vaccine composition is administered more than once to a subject, the dose of each bacterial construct or peptide may vary per administration.

To increase the immunological response, various adjuvants may be used depending on the host species, including but not limited to cholera toxin B subunit, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as cholera toxin B subunit, alum, saponins, nucleic acids, LPS, BCG (bacille Calmette-Guerin), and *Corynebacterium parvum.*

The peptides of the presently disclosed subject matter may be readily prepared by standard, well-established techniques, such as solid-phase peptide synthesis (SPPS) as described by Stewart et al., 1984 and as described by Bodanszky & Bodanszky, 1984. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenly esters.

Examples of solid phase peptide synthesis methods include the BOC method which utilized tert-butyloxcarbonyl as the α-amino protecting group, and the FMOC method which utilizes 9-fluorenylmethyloxcarbonyl to protect the α-amino of the amino acid residues, both methods of which are well known by those of skill in the art.

Incorporation of N- and/or C-blocking groups can also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dicholoromethane. Esterification of the suitably activated carboxyl function e.g., with DCC, can then proceed by addition of the desired alcohol, followed by deprotection and isolation of the esterified peptide product.

Incorporation of N-terminal blocking groups can be achieved while the synthesized peptide is still attached to the resin, for instance by treatment with a suitable anhydride and nitrile. To incorporate an acetyl-blocking group at the N-terminus, for instance, the resin-coupled peptide can be treated with 20% acetic anhydride in acetonitrile. The N-blocked peptide product can then be cleaved from the resin, deprotected and subsequently isolated.

To ensure that the peptide obtained from either chemical or biological synthetic techniques is the desired peptide, analysis of the peptide composition should be conducted. Such amino acid composition analysis may be conducted using high-resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide. Prior to its use, the peptide is purified to remove contaminants. In this regard, it will be appreciated that the peptide will be purified so as to meet the standards set out by the appropriate regulatory agencies. Any one of a number of a conventional purification procedures may be used to attain the required level of purity including, for example, reversed-phase high-pressure liquid chromatography (HPLC) using an alkylated silica column such as C4-, C8- or C18-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

It will be appreciated, of course, that the peptides or antibodies, derivatives, or fragments thereof may incorporate amino acid residues which are modified without affecting activity. For example, the termini may be derivatized to include blocking groups, i.e., chemical substituents suitable to protect and/or stabilize the N- and C-termini from “undesirable degradation”, a term meant to encompass any type of enzymatic, chemical or biochemical breakdown of the compound at its termini which is likely to affect the function of the compound, i.e., sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines ($—NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the presently disclosed subject matter are also contemplated, for example, inverted peptides in which all amino acids are substituted with D-amino acid forms.

Acid addition salts of the presently disclosed subject matter are also contemplated as functional equivalents. Thus, a peptide in accordance with the presently disclosed subject matter treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the presently disclosed subject matter.

The presently disclosed subject matter also provides for homologs of proteins and peptides of the presently disclosed subject matter. Homologs can differ from naturally occurring proteins or peptides by conservative amino acid sequence differences or by modifications which do not affect sequence, or by both.

For example, conservative amino acid changes may be made, which although they alter the primary sequence of the protein or peptide, do not normally alter its function. To that end, 10 or more conservative amino acid changes typically have no effect on protein function.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides or antibody fragments which have been modified using ordinary molecular biological techniques so as to improve their resistance to proteolytic degradation or to optimize solubility properties or to render them more suitable as a therapeutic agent. Homologs of such polypeptides include those containing residues other than naturally occurring L-amino acids, e.g., D-amino acids or non-naturally occurring synthetic amino acids. The peptides of the presently disclosed subject matter are not limited to products of any of the specific exemplary processes listed herein.

Substantially pure protein or peptide obtained as described herein may be purified by following known procedures for protein purification, wherein an immunological, enzymatic, or other assay is used to monitor purification at each stage in the procedure. Protein purification methods are well known in the art, and are described, for example in Deutscher et al., 1990.

One of ordinary skill in the art will appreciate that when more than one peptide is used (for example as provided by a bacteria expressing two or more peptides or by different bacteria expressing different peptides or derivative of the bacteria) that they do not necessarily have to be administered in the same pharmaceutical composition at the same time, and that multiple administrations can also be used. When multiple injections are used they can be administered, for example, in a short sequence such as one right after the other or they can be spaced out over predetermined periods of time, such as every 5 minutes, every 10 minutes, every 30 minutes, etc. Of course, administration can also be performed by administering a pharmaceutical comprising all components to be administered, such as a cocktail comprising bacteria expressing a peptide or derivative of the bacteria of the presently disclosed subject matter. It can also be appreciated that a treatment regimen may include more than one round of injections, spaced over time such as weeks or months, and can be altered according to the effectiveness of the treatment on the particular subject being treated. The administrations can also include different amounts or doses of the same immunogen, or the same immunogen combined with different vehicles or adjuvants, or using different routes.

The presently disclosed subject matter provides multiple methods of using specifically prepared bacteria expressing a peptide or derivative of the bacteria, for example, in fresh or lyophilized liposome, proper routes of administration of the bacteria or derivative thereof, proper doses of the bacteria or derivative thereof, and specific combinations of heterologous immunization including priming in one administration route followed by liposome-mediated antigen boost in a different route to tailor the immune responses in respects of enhancing cell mediated immune response, cytokine secretion, humoral immune response, especially skewing T helper responses to be Th1 or a balanced Th1 and Th2 type. For more detail, see U.S. patent application Ser. No. 11/572,453 (corresponds to U.S. Pat. No. 8,012,932), which claims priority to PCT International Patent Application Serial No. PCT/US2005/026102 (corresponds to PCT International Patent Application Publication No. WO 2006/012539).

A homolog herein is understood to comprise an immunogenic peptide having in some embodiments at least 70%, in some embodiments at least 80%, in some embodiments at least 90%, in some embodiments at least 95%, in some embodiments at least 98%, and in some embodiments at least 99% amino acid sequence identity with the peptides mentioned above and is still capable of eliciting at least the immune response obtainable thereby. A homolog or analog may herein comprise substitutions, insertions, deletions, additional N- or C-terminal amino acids, and/or additional chemical moieties, such as carbohydrates, to increase stability, solubility, and immunogenicity.

In some embodiments of the presently disclosed subject matter, the present immunogenic polypeptides as defined herein, are glycosylated. Without wishing to be bound by any particular theory, it is hypothesized herein that by glycosylation of these polypeptides the immunogenicity thereof may be increased. Therefore, in some embodiments, the aforementioned immunogenic polypeptide as defined herein before, is glycosylated, having a carbohydrate content varying from 10-80 wt %, based on the total weight of the glycoprotein or glycosylated polypeptide. Said carbohydrate content ranges can be from 15-70 wt %, or from 20-60 wt %. In another embodiment, said glycosylated immunogenic polypeptide comprises a glycosylation pattern that is similar to that of the peptides of the human that is treated. It is hypothesized that this even further increases the immunogenicity of said polypeptide. Thus, in some embodiments, the immunogenic polypeptide comprises a glycosylation pattern that is similar to that of the corresponding glycoprotein.

In some embodiments, the source of a peptide comprises an effective amount of at least one immunogenic peptide selected from the peptides described herein, and immunologically active homologs thereof and fragments thereof, or a nucleic acid sequence encoding said immunogenic peptide.

In some embodiments, the present method of immunization comprises the administration of a source of immunogenically active peptide fragments, said peptide fragments being selected from the peptide fragments and/or homologs thereof as defined herein before.

Peptides may advantageously be chemically synthesized and may optionally be (partially) overlapping and/or may also be ligated to other molecules, peptides, or proteins. Peptides may also be fused to form synthetic proteins, as in Welters et al., 2004. It may also be advantageous to add to the amino- or carboxy-terminus of the peptide chemical moieties or additional (modified or D-) amino acids in order to increase the stability and/or decrease the biodegradability of the peptide. To improve immunogenicity, immuno-stimulating moieties may be attached, e.g., by lipidation or glycosylation. To enhance the solubility of the peptide, addition of charged or polar amino acids may be used, in order to enhance solubility and increase stability in vivo.

For immunization purposes, the aforementioned immunogenic peptides of the presently disclosed subject matter may also be fused or bound, covalently or non-covalently, or combined with proteins, such as, but not limited to, tetanus toxin/toxoid, diphtheria toxin/toxoid, cholera toxin B subunit, or other carrier molecules. The polypeptides according to the presently disclosed subject matter may also be advantageously fused to heatshock proteins, such as recombinant endogenous (murine) gp96 (GRP94) as a carrier for immunodominant peptides as described in Rapp & Kaufmann, 2004; Zugel, 2001 or fusion proteins with Hsp70 (see e.g., PCT International Patent Application Publication No. WO 1999/54464).

The individual amino acid residues of the present immunogenic (poly)peptides of the presently disclosed subject matter can be incorporated in the peptide by a peptide bond or peptide bond mimetic. A peptide bond mimetic of the presently disclosed subject matter includes peptide backbone modifications well known to those skilled in the art. Such modifications include modifications of the amide nitrogen, the alpha carbon, amide carbonyl, complete replacement of the amide bond, extensions, deletions, or backbone cross-links. See generally, Spatola, 1983. Several peptide backbone modifications are known and can be used in the practice of the presently disclosed subject matter.

Amino acid mimetics may also be incorporated in the polypeptides. An "amino acid mimetic" as used here is a moiety other than a naturally occurring amino acid that conformationally and functionally serves as a substitute for an amino acid in a polypeptide of the presently disclosed subject matter. Such a moiety serves as a substitute for an amino acid residue if it does not interfere with the ability of the peptide to elicit an immune response. Amino acid mimetics may include non-protein amino acids. A number of suitable amino acid mimetics are known to the skilled artisan, they include cyclohexylalanine, 3-cyclohexylpropionic acid, L-adamantyl alanine, adamantylacetic acid and the like. Peptide mimetics suitable for peptides of the presently disclosed subject matter are discussed by Morgan & Gainor, 1989.

In some embodiments, the present method comprises the administration of a composition (e.g, bacteria or derivative thereof) comprising one or more of the present immunogenic peptides as defined herein above, and at least one excipient. Excipients are well known in the art of pharmacy and may for instance be found in textbooks such as Remington's *Pharmaceutical Sciences,* 18*th ed.* (1990) Mack Publishing, Easton, Pennsylvania, United States of America or *Remington: The Science and Practice of Pharmacy,* 19*th ed.* (1995) Mack Publishing, Easton, Pennsylvania, United States of America.

The present method for immunization may further comprise the administration, and in one aspect, the co-administration, of at least one adjuvant. Adjuvants may comprise any adjuvant known in the art of vaccination or composition for eliciting an immune response and may be selected using textbooks like Colligan et al. (eds.) (1994-2004) Current Protocols in Immunology, John Wiley & Sons, Inc., New York, New York, United States of America.

Adjuvants are herein intended to include any substance or compound that, when used, in combination with an antigen, to immunize a human or an animal, stimulates the immune system, thereby provoking, enhancing or facilitating the immune response against the antigen, preferably without generating a specific immune response to the adjuvant itself. In some embodiments, adjuvants can enhance the immune response against a given antigen by at least a factor of 1.5, 2, 2.5, 5, 10, or 20, as compared to the immune response generated against the antigen under the same conditions but in the absence of the adjuvant. Tests for determining the statistical average enhancement of the immune response against a given antigen as produced by an adjuvant in a group of animals or humans over a corresponding control group are available in the art. The adjuvant preferably is capable of enhancing the immune response against at least two different antigens. The adjuvant of the presently disclosed subject matter will usually be a compound that is foreign to a human, thereby excluding immunostimulatory compounds that are endogenous to humans, such as e.g., interleukins, interferons, and other hormones.

A number of adjuvants are well known to one of ordinary skill in the art. Suitable adjuvants include, e.g., incomplete Freund's adjuvant, alum, aluminum phosphate, aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxy-phosphoryloxy)-ethylamine (CGP 19835A, referred to as MTP-PE), DDA (2 dimethyldioctadecylammonium bromide), polyIC, Poly-A-poly-U, RIBI™, GERBU™, Pam3™, Carbopol™, Specol™, Titermax™, tetanus toxoid, diphtheria toxoid, meningococcal outer membrane proteins, cholera toxin B subunit, diphtheria protein $CRM_{197}$ (and other inactivated diphtheria toxin derivatives). Preferred adjuvants comprise a ligand that is recognized by a Toll-like-receptor (TLR) present on antigen presenting cells. Various ligands recognized by TLR's are known in the art and include e.g., lipopeptides (see e.g., PCT International Patent Application Publication No. WO 04/110486), lipopolysaccharides, peptidoglycans, liopteichoic acids, lipoarabinomannans, lipoproteins (from mycoplasma or spirochetes), double-stranded RNA (poly I:C), unmethylated DNA, flagellin, CpG-containing DNA, and imidazoquinolines, as well derivatives of these ligands having chemical modifications.

In some embodiments of the present methods, one or more immunogenic peptide or bacteria expressing a peptide or derivative of the bacteria are typically administered at a dosage of about 1 ug/kg patient body weight or more at least once. Often dosages are greater than 10 μg/kg. According to the presently disclosed subject matter, the dosages range in some embodiments from 1 μg/kg to 1 mg/kg.

In some embodiments typical dosage regimens comprise administering a dosage of in some embodiments 1-1000 ug/kg, in some embodiments 10-500 μg/kg, in some embodiments 10-150 μg/kg, once, twice or three times a week for a period of one, two, three, four or five weeks. According to some embodiments, 10-100 μg/kg is administered once a week for a period of one or two weeks. In some embodiments, the number of bacteria administered can be varied over a large range, from $10^4$ to $10^{10}$ cells. The doses of the peptide and/or cells can also be varied from one administration to the next, to elicit the most useful immune responses.

The present method, in some embodiments, comprises administration of the present immunogenic peptide or bacteria expressing a peptide or derivative of the bacteria and compositions comprising them via the injection, transdermal, or oral route. In some embodiments of the presently disclosed subject matter, the present method comprises vaginal or rectal administration of the present immunogenic peptide or bacteria expressing a peptide or derivative of the bacteria and compositions comprising them.

Another aspect of the presently disclosed subject matter relates to a pharmaceutical preparation comprising as the active ingredient the present source of a polypeptide as defined herein before. More particularly pharmaceutical preparation comprises as the active ingredient one or more of the aforementioned immunogenic peptides, homologues thereof and fragments of said peptides and homologs thereof, or, alternatively, a bacteria expressing a peptide or derivative of the bacteria as defined herein above.

The presently disclosed subject matter further provides a pharmaceutical preparation comprising one or more of the peptide or bacteria expressing a peptide or derivative of the bacteria of the presently disclosed subject matter. The concentration of said peptides in the pharmaceutical composition can vary widely, i.e., from less than about 0.1% by weight, usually being at least about 1% by weight to as much as 20% by weight or more.

The composition may comprise a pharmaceutically acceptable carrier in addition to the active ingredient. The pharmaceutical carrier can be any compatible, non-toxic substance suitable to deliver the immunogenic peptide or bacteria expressing a peptide or derivative of the bacteria to the patient. For polypeptides, sterile water, alcohol, fats, waxes, and inert solids may be used as the carrier. Pharmaceutically acceptable adjuvants, buffering agents, dispersing agents, and the like, may also be incorporated into the pharmaceutical compositions.

In some embodiments, the present immunogenic peptide or bacteria expressing a peptide or derivative of the bacteria are administered by injection. The parenteral route for administration of the polypeptide is in accordance with known methods, e.g., injection or infusion by intravenous, intraperitoneal, intramuscular, intra-arterial, subcutaneous, rectal, vaginal, or intralesional routes. The peptide or bacteria expressing a peptide or derivative of the bacteria may be administered continuously by infusion or by bolus injection. In some embodiments, a composition for intravenous infusion could be made up to contain 10 to 50 ml of sterile 0.9% NaCl or 5% glucose optionally supplemented with a 20% albumin solution and between 10 μs and 50 mg, in some embodiments between 50 μg and 10 mg, of the peptide or bacteria expressing a peptide or derivative of the bacteria. A typical pharmaceutical composition for intramuscular injection would be made up to contain, for example, 1-10 ml of sterile buffered water and between 10 μg and 50 mg, in some embodiments between 50 ug and 10 mg, of the peptide or bacteria expressing a peptide or derivative of the bacteria of the presently disclosed subject matter. Methods for preparing parenterally administrable compositions are well known in the art and described in more detail in various sources, including, for example, *Remington's Pharmaceutical Sciences,* 18th ed. (1990) Mack Publishing, Easton, Pennsylvania, United States of America; incorporated by reference in its entirety for all purposes.

For convenience, immune responses are often described in the presently disclosed subject matter as being either "primary" or "secondary" immune responses. A primary immune response, which is also described as a "protective" immune response, refers to an immune response produced in an individual as a result of some initial exposure (e.g., the initial "immunization") to a particular antigen. Such an immunization can occur, for example, as the result of some natural exposure to the antigen (for example, from initial infection by some pathogen that exhibits or presents the antigen). Alternatively, the immunization can occur because of vaccinating the individual with a vaccine containing the antigen. For example, the vaccine can be a vaccine comprising one or more antigenic epitopes or fragments of the peptides of the presently disclosed subject matter.

Amino Acid Substitutions

In certain embodiments, the disclosed methods and compositions may involve preparing peptides with one or more substituted amino acid residues. In various embodiments, the structural, physical and/or therapeutic characteristics of peptide sequences may be optimized by replacing one or more amino acid residues. In some embodiments, the presently disclosed subject matter encompasses the substitution of a serine or an alanine residue for a cysteine residue in a peptide of the presently disclosed subject matter. Support for this includes what is known in the art. For example, Kittlesen et al., 1998 provides justification of such a serine or alanine substitution.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the presently disclosed subject matter are also contemplated, for example, inverted peptides in which all amino acids are substituted with D-amino acid forms.

The skilled artisan will be aware that, in general, amino acid substitutions in a peptide typically involve the replacement of an amino acid with another amino acid of relatively similar properties (e.g., conservative amino acid substitutions). The properties of the various amino acids and effect of amino acid substitution on protein structure and function have been the subject of extensive study and knowledge in the art. For example, one can make the following isosteric and/or conservative amino acid changes in the parent polypeptide sequence with the expectation that the resulting polypeptides would have a similar or improved profile of the properties described above:

Substitution of alkyl-substituted hydrophobic amino acids: including alanine, leucine, isoleucine, valine, norleucine, S-2-aminobutyric acid, S-cyclohexylalanine or other simple alpha-amino acids substituted by an aliphatic side chain from C1-10 carbons including branched, cyclic and straight chain alkyl, alkenyl or alkynyl substitutions.

Substitution of aromatic-substituted hydrophobic amino acids: including phenylalanine, tryptophan, tyrosine, biphenylalanine, 1-naphthylalanine, 2-naphthyl alanine, 2-benzothienylalanine, 3-benzothienylalanine, histidine, amino, alkylamino, dialkylamino, aza, halogenated (fluoro, chloro, bromo, or iodo) or alkoxy-substituted forms of the previous listed aromatic amino acids, illustrative examples of which are: 2-,3- or 4-aminophenylalanine, 2-,3- or 4-chlorophenylalanine, 2-,3- or 4-methylphenylalanine, 2-,3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2, 3, or 4-biphenylalanine, 2',-3',- or 4'-methyl-2, 3 or 4-biphenylalanine, and 2- or 3-pyridylalanine.

Substitution of amino acids containing basic functions: including arginine, lysine, histidine, ornithine, 2,3-diaminopropionic acid, homoarginine, alkyl, alkenyl, or aryl-substituted (from $C_1$-$C_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha methyl arginine, alpha methyl 2,3-diaminopropionic acid, alpha methyl histidine, alpha methyl ornithine where alkyl group occupies the pro-R position of the alpha carbon. Also included are the amides formed from alkyl, aromatic, heteroaromatic (where the heteroaromatic group has one or more nitrogens, oxygens, or sulfur atoms singly or in combination) carboxylic acids or any of the many well-known activated derivatives such as acid chlorides, active esters, active azolides and related derivatives) and lysine, ornithine, or 2,3-diaminopropionic acid.

Substitution of acidic amino acids: including aspartic acid, glutamic acid, homoglutamic acid, tyrosine, alkyl, aryl, arylalkyl, and heteroaryl sulfonamides of 2,4-diaminopriopionic acid, ornithine or lysine and tetrazole-substituted alkyl amino acids.

Substitution of side chain amide residues: including asparagine, glutamine, and alkyl or aromatic substituted derivatives of asparagine or glutamine.

Substitution of hydroxyl containing amino acids: including serine, threonine, homoserine, 2,3-diaminopropionic acid, and alkyl or aromatic substituted derivatives of serine or threonine. It is also understood that the amino acids within each of the categories listed above can be substituted for another of the same group.

For example, the hydropathic index of amino acids may be considered (Kyte & Doolittle, 1982). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are in some embodiments within +/−2 is employed, in some embodiments within +/−1 are employed, and in some embodiments within +/−0.5 are employed.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5+/−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In some embodiments, replacement of amino acids with others of similar hydrophilicity is employed.

Other considerations include the size of the amino acid side chain. For example, it would generally not be preferred to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974; Chou & Fasman, 1978; Chou & Fasman, 1979.

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, gln; Asp (D) asn, glu; Cys (C) ala, ser; Gln (Q) glu, asn; Glu (E) gln, asp; Gly (G) ala; His (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Trp. (See e.g., the PROWL website of Rockefeller University). For solvent exposed residues, conservative substitutions would include: Asp and Asn; Asp and Glu; Glu and Gln, Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. (Id.) Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded peptide sequence are well known and a matter of routine experimentation for the skilled artisan, for example by the technique of site-directed mutagenesis or by synthesis and assembly of oligonucleotides encoding an amino acid substitution and splicing into an expression vector construct.

The presently disclosed subject matter is also directed to methods of administering the compounds of the presently disclosed subject matter to a subject.

Pharmaceutical compositions comprising the present compositions are administered to an individual in need thereof by any number of routes including, but not limited to, topical, oral, rectally, vaginally, intravenous, intramuscular, intra-arterial, intramedullary, intrathecal, intraventricular, transdermal, subcutaneous, intraperitoneal, intranasal, enteral, topical, sublingual, or rectal means.

The presently disclosed subject matter is also directed to pharmaceutical compositions comprising the bacteria and/or immunogens of the presently disclosed subject matter. More particularly, such compounds can be formulated as pharmaceutical compositions using standard pharmaceutically acceptable carriers, fillers, solublizing agents, and stabilizers known to those skilled in the art.

The presently disclosed subject matter also encompasses the use of pharmaceutical compositions of an appropriate compound, homolog, fragment, analog, or derivative thereof to practice the methods of the presently disclosed subject matter, the composition comprising at least one appropriate compound, homolog, fragment, analog, or derivative thereof and a pharmaceutically-acceptable carrier.

The pharmaceutical compositions useful for practicing the presently disclosed subject matter may be administered to deliver a dose of between 1 ng/kg/day and 100 mg/kg/day. Pharmaceutical compositions that are useful in the methods of the presently disclosed subject matter may be administered systemically in oral solid formulations, ophthalmic, suppository, aerosol, topical or other similar formulations. In addition to the appropriate compound, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer an appropriate compound according to the methods of the presently disclosed subject matter.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation.

Subjects to which administration of the pharmaceutical compositions of the presently disclosed subject matter is contemplated include, but are not limited to, humans and other primates, mammals including commercially relevant mammals such as cattle, pigs, horses, sheep, cats, and dogs, birds including commercially relevant birds such as chickens, ducks, geese, and turkeys.

Pharmaceutical compositions that are useful in the methods of the presently disclosed subject matter may be prepared, packaged, or sold in formulations suitable for oral, rectal, vaginal, parenteral, topical, pulmonary, intranasal, buccal, ophthalmic, intrathecal or another route of administration. Other contemplated formulations include projected nanoparticles, liposomal preparations, resealed erythrocytes containing the active ingredient, and immunologically-based formulations.

A pharmaceutical composition of the presently disclosed subject matter may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the presently disclosed subject matter will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the presently disclosed subject matter may further comprise one or more additional pharmaceutically active agents. Particularly contemplated additional agents include anti-emetics and scavengers such as cyanide and cyanate scavengers.

Controlled- or sustained-release formulations of a pharmaceutical composition of the presently disclosed subject matter may be made using conventional technology. A formulation of a pharmaceutical composition of the presently disclosed subject matter suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

Liquid formulations of a pharmaceutical composition of the presently disclosed subject matter which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as *arachis*, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, and hydroxypropylmethylcellulose.

Known dispersing or wetting agents include, but are not limited to, naturally occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively).

Known emulsifying agents include, but are not limited to, lecithin and acacia. Known preservatives include, but are not limited to, methyl, ethyl, or n-propyl para hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the presently disclosed subject matter may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the presently disclosed subject matter may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the presently disclosed subject matter may also be prepared, packaged, or sold in the form of oil in water emulsion or a water-in-oil emulsion. The oily phase may be a vegetable oil such as olive or *arachis* oil, a mineral oil such as liquid paraffin, or a combination of these. Such compositions may further comprise one or more emulsifying agents such as naturally occurring gums such as gum acacia or gum tragacanth, naturally occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the presently disclosed subject matter may also be prepared, packaged, or sold in a formulation suitable for rectal administration, vaginal administration, parenteral administration The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally acceptable diluent or solvent, such as water or 1,3 butane diol, for example.

Other acceptable diluents and solvents include, but are not limited to, Ringer's solution, isotonic sodium chloride solution, and fixed oils such as synthetic mono or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi liquid preparations such as liniments, lotions, oil in water or water in oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the presently disclosed subject matter may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder dispensing container such as a device comprising the active ingredient dissolved or suspended in a low-boiling propellant in a sealed container.

In some embodiments, such powders comprise particles wherein at least 98% of the particles by weight have a diameter greater than 0.5 nanometers and at least 95% of the particles by number have a diameter less than 7 nanometers. In some embodiments, at least 95% of the particles by weight have a diameter greater than 1 nanometer and at least 90% of the particles by number have a diameter less than 6 nanometers. Dry powder compositions can include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the presently disclosed subject matter formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the presently disclosed subject matter.

Another formulation suitable for intranasal administration is a coarse powder comprising the active ingredient and having an average particle from about 0.2 to 500 micrometers. Such a formulation is administered in the manner in which snuff is taken i.e., by rapid inhalation through the nasal passage from a container of the powder held close to the flares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the presently disclosed subject matter may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, have in some embodiments an average particle or droplet size in the range from about 0.1 to about 200 nanometers, and may further comprise one or more of the additional ingredients described herein.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the presently disclosed subject matter are known in the art and described, for example in Remington's Pharmaceutical Sciences, 18th ed. (1990) Mack Publishing, Easton, Pennsylvania, United States of America, which is incorporated herein by reference.

Typically, dosages of the composition of the presently disclosed subject matter which may be administered to an animal, preferably a human, range in amount from 1 μg to about 100 g per kilogram of body weight of the subject. While the precise dosage administered will vary depending upon any number of factors, including but not limited to, the type of animal and type of disease state being treated, the age of the animal and the route of administration. In some embodiments, the dosage of the compound will vary from about 10 mg to about 10 g per kilogram of body weight of the animal. In another embodiment, the dosage will vary from about 10 mg to about 1 g per kilogram of body weight of the subject.

The composition may be administered to a subject as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the sex and age of the subject, etc.

The presently disclosed subject matter further provides kits comprising peptide or bacteria expressing a peptide or derivative of the bacteria peptides and cocktails of the presently disclosed subject matter useful for eliciting an immunogenic response, and further includes an applicator and an instructional material for the use thereof.

EXAMPLES

The following EXAMPLES provide illustrative embodiments. In light of the present disclosure and the general level of skill in the art, those of skill will appreciate that the following Examples are intended to be exemplary only and that numerous changes, modifications, and alterations can be employed without departing from the scope of the presently disclosed subject matter.

Without further description, it is believed that one of ordinary skill in the art can, using the preceding description and the following illustrative EXAMPLES, make and utilize the compounds of the presently disclosed subject matter and practice the methods of the presently disclosed subject matter. The following EXAMPLES therefore particularly point out embodiments of the presently disclosed subject matter and are not to be construed as limiting in any way the remainder of the disclosure.

Materials and Methods Employed in Examples

Representative HIV Vaccine Construct Components of the Presently Disclosed Subject Matter:

Truncated or Shorter AIDA (TrnAIDA):

(SEQ ID NO: 1)
QYRPENGSYATNMALANSLFLMDLNERKQFRAMSDNTQPESASVWMKITG
GISSGKLNDGQNKTTTNQFINQLGGDIYKFHAEQLGDFTLGIMGGYANAK
GKTINYTSNKAARNTLDGYSVGVYGTWYQNGENATGLFAETWMQYNWFNA
SVKGDGLEEEKYNLNGLTASAGGGYNLNVHTWTSPEGITGEFWLQPHLQA
VWMGVTPDTHQEDNGTVVQGAGKNNIQTKAGIRASWKVKSTLDKDTGRRF
RPYIEANWIHNTHEFGVKMSDDSQLLSGSRNQGEIKTGIEGVITQNLSVN
GGVAYQAGGHGSNAISGALGIKYSF.

The above-presented AIDA construct was prepared by removing 122 amino acids at the N-terminus:

(SEQ ID NO: 2)
LNPTKESAGNLTVSNYTGTPGSVISLGGVLEGDNSLTDRLVVKGNTSGQS
DIVYVNEDGSGGQTRDGINIISVEGNSDAEFSLKNRVVAGAYDYTLQKGN
ESGTDNKGWYLTSHLPTSDTR

This removed the adhesin fragment that extended from the B-barrel of the autotransporter. With this construction, MPER scaffolds are presented closer to the bacterial cell wall surface because placing the MPER antigen on the exterior of a cell, embedded in a lipid bilayer, presents the antigen in a context that resembles the native configuration in the viral envelope.

Truncated or Shorter HiaAT (TrnHiaAT):

(SEQ ID NO: 3)
GTASALAASQLPQATMPGKSMVAIAGSSYQGQNGLAIGVSRISDNGKVII
RLSGTTNSQGKTGVAAGVGYQW

The above-presented HiaAT construct was shorted by removing 50 amino acids at the N-terminus:

(SEQ ID NO: 4)
NVANGDISATSTDAINGSQLYAVAKGVTNLAGQVNNLEGKVNKVGKRAD
A.

This removed an adhesin fragment and the distal portion of the trimer that extends out of the B-barrel of the autotransporter. The structure of the HiaAT strongly resembles the structure of the HIV envelope trimer embedded in the virion envelop. This construct presents the native MPER in its natural confirmation as a trimer on the bacterial surface.

ScafMPER.024:

This MPER-scaffold peptide mimics the 10E8 broadly neutralizing epitope:

```
                                        (SEQ ID NO: 5)
ASLWNWFDITNWLWYIKNLIAIGIGATLGAWLRWVLGLKLNGAGWPWGTL

TANLVGGYLIGVMVALIASHPSWPAWIRLAAVTGFLGGLTTFSTFSAETV

DMLCRGVYATAAAYAGASLAGSLAMTGLGLATVRLLL.
```

3AGJ Scaffold:

This construct is a computationally engineered polypeptide designed to mimic the 10E8 broadly neutralizing epitope:

```
                                        (SEQ ID NO: 6)
KPHMNLVVIGHVDHGKSTLVGHLLARLGYIEWFKLTNLLHQARARGKGSF

GFAWILDKMKEERERGITIDLTFMKFETKKYVFTIIDAPGHRDFVKNMIT

GASQADAAILVVSARKGEFEAGMSTEGQTREEILLLARTMGIEQIIVAVN

KMDAPDVNYDQKRYEFVVSVLKKFMKGLGYQVDKIPFIPVSAWKGDNLIE

RSPNMPWYNGPTLVEALDQLQPPAK.
```

ES2 Scaffold:

```
                                        (SEQ ID NO: 7)
SDPVRQYLHEIGEVLELDKWAELGAAAKVEEGMEAIKKLSEATGLDQELI

REVVRAKILGTAAIQKIPGLKEKPDPKTVEEVDGKLKSLPKELKRYLHIA

REGEAARQHLIEANLRLVVSIAKKYTGRGLSFLDLIQEGNQGLIRAVEKF

EYKRGFAFSTYATWWIRQAINRAIADQAR
```

Computationally engineered protein designed by Peter Kwong to mimic the 2F5 broadly neutralizing epitope.

Design Strategy:

1) New TrnAIDA constructs were designed with an HA stuffer containing an HA-tag (CCTGTCTTCTTATCCATACGATGTACCGGATTACGCGGGAAGACG AGTGTTA; SEQ ID NO: 8) in pUC57. The construct has restriction sites (BsaI and XmaI) flanking the "TrnAIDA-HA stuffer" region that is utilized to clone the expression cassette in RASV. Also the HA-stuffer is flanked by two BbsI sites that replace the HA with scaffolded MPER. Furthermore, three (3) variants were designed containing different number of glycine residues (3G, 5G, 7G) separating TrnAIDA and the HA-stuffer. The additional glycine residues assist in pushing out the HA-tag of the chimeric protein further into the extracellular space beyond the autotransporter's beta barrel pore.

2) New TrnAIDA constructs were designed with either the 3AGJ, ES2, or ScafMPER.024 MPER scaffold in pUC57. These constructs contain a rhamnose-inducible promoter (Rh) to provide the ability to tightly induce and regulate the gene expression. The constructs have restriction sites (XbaI and NotI) flanking the cassette containing Rhamnose promoter-TrnAIDA-MPER-scaffold, to allow the sub-cloning into the pD861 vector background. Furthermore, three (3) variants of each MPER that contain glycine residues (3G, 5G, and 7G) separating TrnAIDA and the respective scaffolded-MPERs. Extra glycines are added so that the scaffolded MPER moiety of the autotransporter/scaffolded MPER chimeric protein is "pushed out" further into the extracellular space beyond the autotransporter's beta barrel pore.

3) The Native MPER (LLELDKWASLWNWFDITNWLWYIK; SEQ ID NO: 9) was designed and constructed in fusion with TrnHiaAT along with some or all residues from the gp41 transmembrane stalk domain (IFIIIVGSLIGLR; SEQ ID NO: 10). As representative non-limiting examples, for TrnHiaAT-Native MPER constructs, three (3) approaches were designed and attempted to fuse the MPER to HiaAT while matching and conserving the heptad assignments from the gp41 transmembrane domain to promote the native trimeric, coiled-coil conformation of MPER. These representative non-limiting fusion sequences are as described below. In accordance with the presently disclosed subject matter, additional examples of fusion sequences can be provided by adding or subtracting amino acids. Such examples are meant to be included with the terms "homolog" and/or "fragment" as used herein. Fusion peptide sequences, which are not MPER sequence per se. They are from a different part of the Envelope protein:

```
(1) Native MPER Version 1:
                                        (SEQ ID NO: 11)
LLELDKWASLWNWFDITNWLWYISQLPQATMPGKSMVAIAGSSYQGQNGL

AIGVSRISDNGKVIIRLSGTTNSQGKTGVAAGVGYQW

(2) Native MPER Version 2:
                                        (SEQ ID NO: 12)
LLELDKWASLWNWFDITNWLWYIKIFIIIVSQLPQATMPGKSMVAIAGSS

YQGQNGLAIGVSRISDNGKVIIRLSGTTNSQGKTGVAAGVGYQW

(3) Native MPER Version 1:
                                        (SEQ ID NO: 13)
LLELDKWASLWNWFDITNWLWYIKIFIIIVGSLIGLRSQLPQATMPGKSM

VAIAGSSYQGQNGLAIGVSRISDNGKVIIRLSGTTNSQGKTGVAAGVGYQ

W
```

Furthermore, a trimeric GCN4 motif (MKQIEDKIEEILSKIYHIENEIARIKKLIGEV; SEQ ID NO: 14) was added at the N-terminus of the Native MPER to further stabilize the TrnHiaAT trimer, promoting the Native MPER to be presented in its native confirmation at the cell surface. A series of fusion versions with different linker lengths are designed and tested for the native-like affinities. All these constructed are cloned in pD861-rhamnose inducible vector using XbaI and NotI restriction sites. The trimerization domains were used in some but not all implementations. Again, the GCN4 trimerization domain is one example of a trimerization domain. Other trimerization domains can be employed and are within the scope of the presently disclosed subject matter.

Introduction to the EXAMPLES

An effective HIV vaccine should induce good humoral and mucosal immunity, eliciting production of broadly neutralizing (BN) antibodies (Abs) capable of protecting against infection by a wide variety of HIV-1 viral strains (Mascola & Montefiori, 2010; Mascola & Haynes, 2013; Kwong et al., 2013). A vaccine that elicited good cell mediated immunity would offer additional benefits. Antigen targets for 7 classes of BNAbs have been identified: (1) the CD4 binding site (Chen et al., 2009; Zhou et al., 2010; McLellan et al., 2011);

(2) the V1V2 binding site at the trimer apex (Walker et al., 2009; Walker et al., 2011a; Walker et al., 2011b; U.S. Pat. No. 9,988,424); (3) the V3 glycan site (Calarese et al., 2003; Pejchal et al., 2011); (4) a glycan site on the gp120 outer domain (2G12 binding site; Kong et al., 2016; van Gils et al., 2016); (5) a region comprising residues from both gp120 and gp41 between MPER and gp120 (Salzwedel et al., 1999; Zhu et al., 2011); (6) the HIV fusion peptide (Muster et al., 1993; Morris et al., 2011); and (7) the membrane-proximal external region (MPER; Zwick et al., 2001; Zwick et al., 2005; Buzon et al., 2010; Burton et al., 2012; van Bloois et al., 2011; Nicolay et al., 2015; Henderson et al., 2000).

A compelling approach to developing an HIV vaccine would involve production of immunogens resembling epitopes bound by BNAbs, but successful development of such immunogens has been challenging. Making immunogens that mimic epitope shapes from discontinuous protein regions is difficult; making immunogens mimicking complex carbohydrates shapes is even harder. MPER, a highly conserved, linear and non-glycosylated region comprising 24 residues at the N-terminus of gp41, represents an appealing target from an engineering perspective (Jose & Meyer, 2007; Kwong et al., 2013).

A broad consensus holds that an ideal HIV vaccine would be orally administered and inexpensive and that the best way to produce an effective vaccine involves construction of an antigen that elicits production of antibodies like the few identified Broadly Neutralizing (BN) Monoclonal Antibodies (MAbs). One Env BN MAb binding site, the gp41 Membrane Proximal External Region (MPER), is a small (17-22 aa), linear region in the gp41 trimeric stalk adjacent to the transmembrane domain and virion lipid bilayer. Unfortunately, synthetic MPER peptides do not elicit the required immune responses, probably because they do not assume the correct shape absent the context of complete Env. Recent efforts to make "scaffold" MPERs, where computational modeling informs placement of MPER-like sequences in a larger scaffold protein designed to create an MPER-like shape, have been hampered because scaffold MPERs made in bacteria or mammalian cells produce insoluble aggregates. However, the presently disclosed subject matter places scaffold MPER-derived proteins and trimeric native MPER peptides in bacterial outer membranes using Gram$^-$ autotransporter (AT) expression cassettes, obviating aggregation problems. This approach also places the MPER-derived antigens in close proximity to a lipid bilayer (the bacterial outer member), which is helpful since some known anti-MPER BNMAbs bind MPER while also interacting with the virion envelope lipid bilayer. Expression on the exterior of the bacteria enables direct binding to BCRs, as well as subsequent antigen processing and presentation.

Candidate HIV recombinant bacterial vaccines are prepared through two complementary approaches: (1) a more conventional Killed Whole Cell (KWC) approach; and (2) a live recombinant bacteria. AT surface expression cassettes function well in live bacteria. In addition to the killed and live bacteria derivatives of the bacteria, such as bacterial fragments, blebs, vesicles, minicells etc., can be used.

The following EXAMPLES show the surface-expressed MPER-derived proteins bind anti-MPER BN MAbs, that mice immunized with Gram-bacteria expressing MPER-derived antigens on their surfaces develop immune responses in sera and vaginal wash material that bind bacteria expressing MPER-derived antigens on their surfaces, and that at least one scaffold MPER surface expressed in bacteria can elicit the production of sera with HIV neutralizing activity.

Aspects of the following EXAMPLES include:

1. Production of HIV-1 vaccine constructs with MPER-derived proteins placed on the bacterial surface using AT expression cassettes;
2. Evaluation of the ability of the vaccine candidates to bind anti-MPER broadly neutralizing MAbs and to elicit production of mucosal secretions and antisera that bind MPER; and
3. Testing of HIV neutralizing ability of mucosal secretions and antisera, testing of cellular immune responses elicited by the vaccines; and testing of the ability of the immune responses elicited by the candidate vaccines to block transmission in animal model systems.

MPER-derived constructs are placed on the surfaces of bacteria for KWC candidate vaccines and RASVs using AT expression cassettes, the ability of the MPER-derived immunogens produced to bind BN MAbs is confirmed, and the ability of the MPER-producing RASVs to elicit BN mucosal, humoral, and cell-mediated immunity is tested using ELISAs and ELIspot assays. Available scaffold MPER constructs are iteratively tested as follows: expressed via a monomeric autotransporter, native MPER sequence expressed with a trimeric autotransporter, using intranasal, oral, and subcutaneous routes, in multiple prime-boost schema, evaluating sera and vaginal wash material for their ability to bind bacteria expressing MPER-derived antigens on their surfaces and neutralize HIV. Production of an MPER-producing RASV that elicits a BN anti-MPER neutralizing immune responses provides for the development of an HIV vaccine.

HIV-1 candidate vaccines are prepared by placing MPER immunogens on the surfaces of bacteria using Gram$^-$ autotransporter (AT) surface expression cassettes using two alternative approaches. In one approach, these are killed (formalin fixed) whole cell vaccines, analogous to the licensed/WHO qualified vaccines for *Salmonella Typhi* and cholera, and in a second approach, live recombinant bacterial vaccines. The strategy solves several problems: (1) the system presents antigens that are binding targets of HIV BNMAbs directly to the immune systems of the oropharyngeal and GI mucosa; (2) placing MPER antigen on the exterior of a cell, embedded in a lipid bilayer, presents antigen in a context that resembles the native configuration in the viral envelope; (3) tightly coupled synthesis and AT-mediated surface export obviates previous problems of aggregate formation with MPER-derived proteins made in bacteria and mammalian cells; and (4) bacteria are inexpensive to grow, easy to transport when lyophilized, and highly immunogenic, serving as their own adjuvants. Both KWC Gram$^-$ bacterial vaccines and live bacterial vaccines are in current human and veterinary use. Millions of doses of KWC *Salmonella* and cholera vaccines are produced each year. Similarly, live attenuated bacterial vaccines have been licensed for human and veterinary applications. KWC and live bacterial vaccines can be produced for less than $1 per dose, lyophilized and reconstituted at time of use, without need for a cold chain, making them ideal for use in a global health context. They have been delivered orally, or by general exposure to poultry and livestock by spraying flocks and herds. Live *Salmonella* vaccines are in current clinical use.

Without wishing to be bound by any particular theory, it is provided herein that: Gram$^-$ bacteria expressing MPER-derived proteins via monomeric AT expression cassettes or native MPER via trimeric AT expression cassettes bind anti-MPER BNMAbs. Immunization with the bacteria expressing MPER immunogens elicit broadly neutralizing mucosal secretion and sera immune responses, representing candidate prophylactic HIV vaccines.

The following EXAMPLES can employ both a KWC approach and an live bacterial vaccine platform: (1) scaffold MPER (heterologous proteins with MPER-derived sequences designed to mimic an MPER-like tertiary structure); and (2) native trimeric MPERs, confirming that the bacteria bind BNMAbs. It is confirmed that the MPER-derived antigens on the surfaces of the bacteria bind the anti-MPER BNMAbs, then their ability to elicit anti-MPER binding activity in mucosal secretions and sera after oral immunization is evaluated. It is determined whether the secretions and sera neutralize HIV in vitro. Neutralization breadth is also determined. The ability of the candidates to block HIV transmission in animal models is also tested and rapid clinical testing and development is pursued.

MPER is an attractive target for vaccine development. Gram$^-$ bacterial vaccines are orally delivered, inexpensive to produce, elicit potent immune responses, and have characteristics ideal for global use. They represent well-established technology for the prevention of bacterial disease. The production of oral recombinant bacterial HIV-1 vaccines that elicit a broadly neutralizing anti-MPER immune response provides for the development of a protective prophylactic HIV vaccine. Also provided is a bacterial MPER-based candidate oral vaccine, suitable for advanced preclinical studies and early clinical trials, as an attractive candidate for a globally appropriate HIV vaccine.

Engineering immunogens that elicit immune responses like those of known BNAbs is a goal for HIV vaccine development but producing such immunogens has been difficult. An immunogen that elicits an anti-MPER BN mucosal immune response would make an important contribution. The following EXAMPLE illustrates a novel approach to produce HIV MPER candidate vaccines. The vaccines are particularly innovative in that they use monomeric and trimeric Gram$^-$ autotransporters to place MPER-scaffolds and native trimeric MPER peptides on the bacterial surface, associated with a lipid bilayer, similar to the environment of gp41 in the virion envelope. The vaccines are also innovative in that they are designed to elicit a mucosal immune response via interactions with both the mucosa of the oral cavity and the gut-associated lymphoid tissue (GALT), and so should be particularly effective in producing mucosal immunity in compartments important for HIV transmission, including genital and GI tracts.

Overview of Examples 1-4

A series of experiments were conducted to test essential concepts and components of the vaccine system. These experiments included the demonstration that: (a) MPER scaffold-derived constructs can be placed on the surfaces of Gram$^-$ bacteria; (b) the MPER-derived constructs expressed on the surfaces of the Gram$^-$ bacteria bind their cognate anti-HIV BNMAbs; and (c) the MPER scaffold-derived proteins on the surface of Gram$^-$ bacteria are sufficiently immunogenic to elicit sera and vaginal wash material that bind the surface-expressed MPER scaffold-derived proteins. Data is also presented that at least one of our immunogens can elicit an anti-HIV neutralizing response.

Example 1

AT Surface Expression Cassettes for HIV Vaccine Antigen Production

Plasmids were synthesized with AIDA-I AT expression cassettes as disclosed herein above. The parental versions of the plasmids have an influenza virus HA immunotag in the surface expression cassettes, with a trypsin cleavage site placed between the HA immunotag and the β-barrel of the autotransporter (Kramer et al., 2003; Jose & Meyer, 2007; Benz & Schmidt, 1992). This trypsin site enabled verification that the autotransporter places the recombinant protein on the bacterial cell surface. Protein extracts from untransformed Gram$^-$ bacteria showed no band recognized by the anti-HA MAb in immunoblots. A band was observed from protein extracts from bacteria transformed with the plasmids. When the bacteria are treated with trypsin and then washed prior to protein extract production, the band is no longer present because trypsin treatment removes the HA immunotag due to the trypsin cleavage site engineered into the recombinant protein between the HA passenger protein and the β-barrel anchored into the bacterial outer membrane, indicating that the systems place essentially all of the recombinant chimeric AT proteins on the cell surface, since essentially no trypsin-insensitive protein was observed. Synthesis of the chimeric AT protein and export to the cell surface is thus very tightly coupled. For the MPER-scaffolds this was important because it suggested that there is no accumulation of MPER scaffold proteins in the bacterial cytoplasm, which in the past has been problematic. The finding encouraged the employing of the AT system for scaffold MPER expression, as previous attempts at producing MPER scaffolds in bacteria produced large amounts of insoluble aggregates as inclusion bodies.

To show that the AIDA-I surface expression cassette effectively places HIV MPER vaccine immunogens on the surfaces of Gram$^-$ bacteria, scaffold MPER proteins were inserted into an AIDA-I surface expression cassette under the control of a rhamnose-inducible promoter, which provided for the control the expression level of the scaffold MPER proteins in these experiments. Plasmids were transformed into a *Salmonella* strain. The constructs include ES2, designed to bind the 2F5 BNMAb and 3AGJ, designed to bind the newer, higher affinity 10E8 BNMAb. Cells were induced with optimized rhamnose concentrations, comparing them to the parental untransformed bacteria, using as a primary antibody the 2F5 or 10E8 anti-HIV MPER BNMAb, followed by staining with Alexa Fluor 488 anti-IgG secondary Ab, and the stained bacteria were tested with flow cytometry (FIG. 1). The results showed that expressing either of the MPER-scaffold proteins on the surfaces of bacteria using an AT expression cassette yielded *Salmonella* with antigens placed in their outer membranes that bound their respective anti-HIV BNMAbs. This suggested that the AT cassette-expressed MPER epitope placed on the surfaces of the bacteria existed in the desired shape, so the chimeric proteins represent an excellent candidate MPER immunogen. The structures on the surfaces of the bacteria that can bind BNMAbs are expected to elicit the production of antibodies with binding characteristics similar to those of the BNMAbs when the bacteria are used as immunogens.

Example 2

Testing Preliminary Versions of the Surface Expression System and Using Gram$^-$ Bacteria for Scaffold MPER Expression for the Ability to Elicit Immune Responses To obtain preliminary evidence about whether the vaccine systems would be able to elicit an anti-MPER immune response when introduced into an animal, prior to the construction and evaluation of the live a live *Salmonella* vaccine, MPER scaffolds were expressed on the surface of an RASV strain, using the initial rhamnose-inducible system with which MPER scaffold expression was optimized by titrating the rhamnose concentration. A formalin-fixed killed whole cell test vaccine was prepared, verifying MPER expression flow cytometrically as in FIG. 1. Mice were immunized intranasally, in parallel with a positive control bacterial preparations expressing the HA immunotag on the cell surface. After six weeks, at the end of the experiment, following immunization and boosts at 14 and 28 days, vaginal wash material and sera at terminal bleeds were collected, and flow cytometry was used to test the ability of sera and vaginal wash material to bind bacteria expressing the scaffold MPERs.

Figure 2:
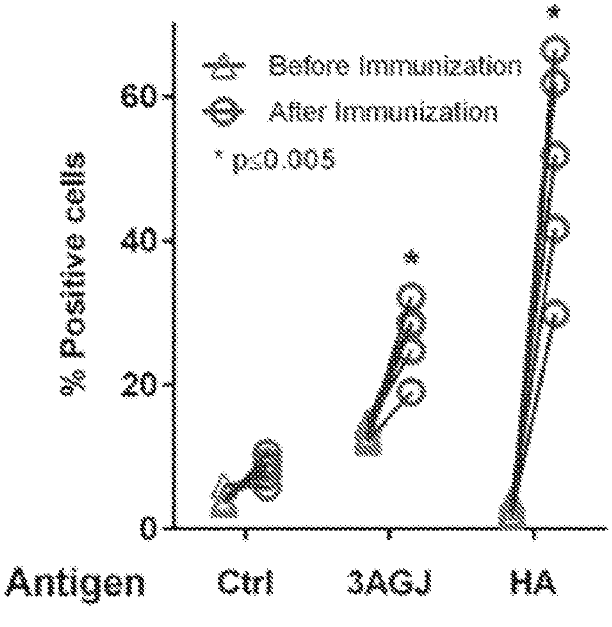
FIG. 2 is a plot showing binding of vaginal wash material following intranasal immunization with surface-expressed MPER scaffold protein. Mice were immunized intranasally with a formalin-fixed killed whole cell *Salmonella* vaccine. The plot shows results evaluating vaginal wash material from mice immunized with negative control *Salmonella, Salmonella* expressing the 3AGJ MPER scaffold-derived protein on its surface, and control *Salmonella* expressing the influenza virus HA immunotag (triangles show before immunization; circles show after immunization). The binding of vaginal wash material obtained after 6 weeks was tested, at the end of the experiment, to bind the bacteria using flow cytometry. Immunization with the 3AGJ-expressing bacteria produced a significant increase in binding activity to the 3AGJ-expressing bacteria. Because a goal for any HIV vaccine would be to block sexual transmission of HIV, at least in part by inactivating the virus in the female genital tract, this finding indicated that the vaccine would likely be able to inhibit HIV sexual transmission. $^{*}p \leq 0.005$.

FIG. 2 shows the results from testing vaginal wash material from mice immunized with bacteria expressing the 3AGJ MPER scaffold designed to bind the 10E8 BNMAb. A significant increase in MPER scaffold binding activity was found in the vaginal wash material after immunization with bacteria expressing the 3AGJ. Similar results were found with the ES2 MPER scaffold, and with sera. The results suggested that mucosal immunization with bacteria expressing MPER scaffold-derived proteins on the surface elicited production of a mucosal immune response in the female genital tract, a key characteristic for a prophylactic HIV vaccine.

The ability of a live *Salmonella* vaccine to elicit an immune response to an MPER scaffold protein was also tested. A live *Salmonella* vaccine with MPER scaffold AT-mediated surface expression under the control of a rhamnose-inducible promoter, inducing expression with high levels of rhamnose, was produced, and that the expression was maintained for at least three passages in liquid culture and in serial passages on plates for >1 week was demonstrated.

Figure 3:
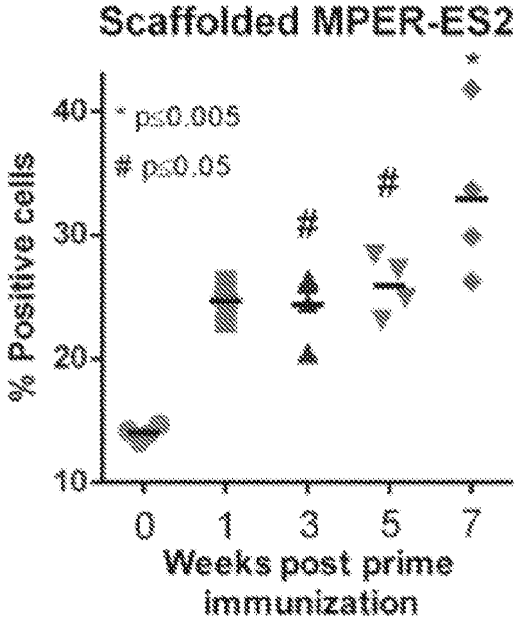
FIG. 3 is a plot showing induction of humoral immunity by a live *Salmonella* strain expressing a scaffolded MPER protein on the bacterial surface, as an example of another way to elicit immune responses directed against the HIV MPER when MPER-derived proteins are expressed on the bacterial surface using a Gram-negative autotransporter. Mice were orally immunized with $10^8$ live *Salmonella* expressing the ES2 scaffolded MPER-derived protein on their surfaces. Blood was collected at serial times as indicated after immunization and sera were tested for their abilities to bind the scaffolded MPER-derived ES2 proteins on their surfaces by flow cytometry. A significant increase in binding to the *Salmonella* following the immunizations was observed compared to the pre-immunization baseline. This result indicated further that the MPER-related immunogens expressed on the surface of the bacteria functioned as effective immunogens in the context of an immunization with live Gram-negative bacteria. p-values as indicated were determined by t-test. $*p \leq 0.005$; $\#p \leq 0.05$.

Mice were inoculated orally with the vaccine (prime immunization at day 0, with boosts at 1, 3, and 5 weeks). Serial sera, vaginal washes, and feces were collected. FIG. 3 shows the results for studies testing the induction of the ability of the sera to bind the bacteria expressing the ES2 MPER scaffold. It was found that oral immunization with the live *Salmonella* vaccine expressing the MPER-derived antigen on their surfaces elicited an increasing and significant anti-MPER derived protein binding activity, as assessed by flow cytometry. Similar results were observed for the 3AGJ scaffold MPER, and for vaginal wash samples. Thus, a live bacterial vaccine, even an early design, elicited a humoral immune response against MPER scaffold protein expressed on the surface of bacteria via an AT expression cassette, and the MPER scaffolds were immunogenic when expressed on the surfaces of the bacteria.

Example 3

Native MPER Expressed Via Trimeric Autotransporters

Data (FIG. 1) showed that placing a scaffold MPER-derived protein on the surface of $Gram^-$ bacteria enabled binding of BNMAbs to the bacteria, suggesting that the proteins bacterial surface assumed shapes similar to that of the native MPER in the virion envelope. This was highly promising for an immunogen capable of eliciting an anti-MPER response. Nonetheless, an alternative approach was evaluated in this EXAMPLE.

A recombinant or synthetic trimer has been recognized by many investigators as an ideal goal in HIV vaccine immunogen production (Burton et al., 2012), but it has been technically difficult to develop an immunogenic soluble trimeric Env-derived vaccine antigen capable of eliciting a BN neutralizing response (Grundner et al., 2005; Phogat & Wyatt, 2007; Sanders et al., 2015). However, in addition to monomeric ATs, there also exists a class of trimeric ATs, like the *Haemophilus influenzae* Hia autotransporter (Surana et al., 2004; Cotter et al., 2006) that trimerizes in forming the bacterial outer membrane-anchored β-barrel and then translocates 3 passenger proteins through the β-barrel's pore simultaneously. The structure of these trimeric autotransporters strongly resembles the structure of the HIV envelope trimer embedded in the virion envelope (Chan et al., 1997; Meng et al., 2006), suggesting that trimeric ATs may be helpful in engineering an expression system to place MPER peptides onto a bacterial surface in conformations resembling the native trimer.

Figure 4:
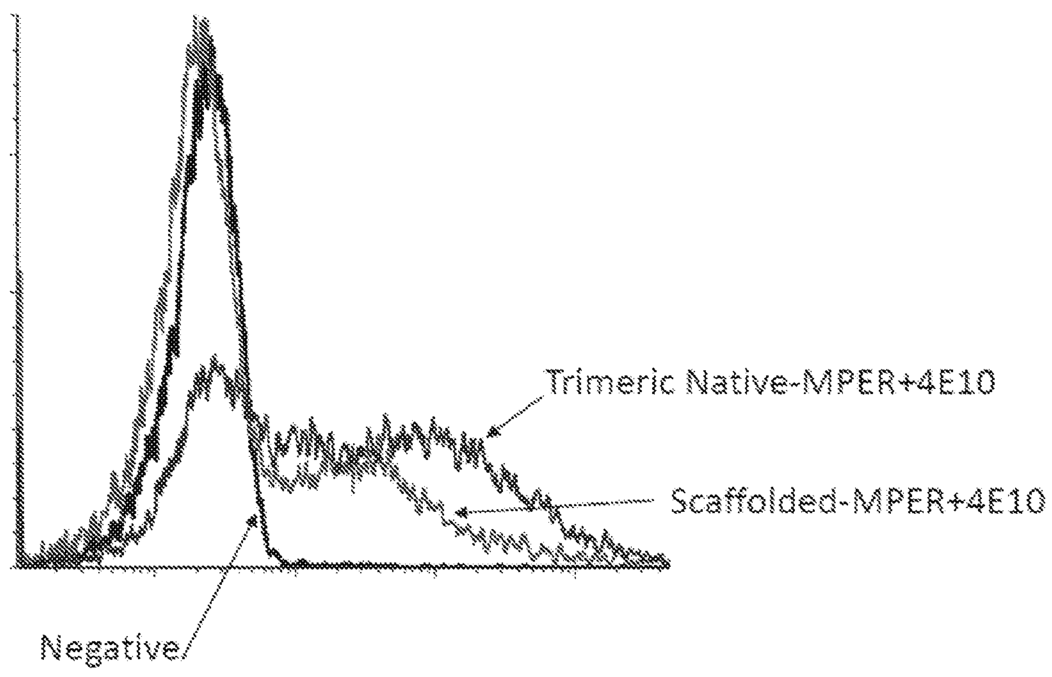
FIG. 4 is a plot showing that a native MPER peptide (that is, not a scaffold MPER protein) expressed on the bacterial surface via a different autotransporter protein, the Hia trimeric autotransporter (Meng et al., 2006), bound anti-HIV BNMAbs. The Hia trimeric autotransporter has a structure that shares similarities with the structure of the HIV envelope protein. Bacteria transformed with a monomeric AIDA-I AT expression cassette expressing the 3AGJ MPER scaffold ("Scaffolded-MPER+4E10"), a monomeric scaffold MPER protein, or bacteria transformed with a trimeric Hia AT expression cassette expressing the native (non-scaffold) 24 amino acid MPER peptide ("Trimeric Native-MPER+4E10") were stained with the 4E10 anti-MPER BNMAb. Untransformed bacteria ("Negative") were not stained with the BNMAb. All samples were then stained with a fluorescently tagged secondary Ab and subjected to flow cytometry. Both the surface-expressed MPER scaffold protein and the trimeric native MPER peptides were recognized by the anti-MPER BNMAb, suggesting that when the trimeric Hia autotransporter was used to place a native MPER peptide (i.e., not a scaffold MPER), the result was bacteria that expressed an MPER-derived immunogen in a conformation sufficiently close to native MPER to be recognized by the anti-MPER BN MAb was present on the surfaces of the bacteria. This finding in turn, again, suggested that the recombinant HIV MPER antigen placed on the surface of the bacteria was in a shape and cellular context adjacent to a lipid bilayer sufficiently similar to the native conformation in the HIV virion to elicit an anti-HIV immune response.

Expression plasmids employing the Hia trimeric AT were produced and data were obtained showing that that the Hia AT could be used to place recombinant MPER peptides on the surfaces of $Gram^-$ bacteria (FIG. 4). In this experiment, the 24-amino acid MPER sequence was expressed on the cell surface using the Hia AT expression cassette, with surface expression evaluated by flow cytometry using the 4E10 BNMAb as primary Ab. The results showed that the 4E10 BNMAb recognized the surface expressed trimeric MPER peptide. In other experiments it was determined that native MPER peptide expressed on the bacterial surface using the Hia trimeric AT bound all BNMAbs tested (i.e., 2F5 and 10E8, in addition to 4E10).

Trimeric AT expression cassettes therefore represent an alternative approach to place MPER trimers on the bacterial surfaces, in a structure resembling native trimeric gp41, in addition to the monomeric AIDA-I AT expression cassette approach.

Example 4

HIV Neutralization by Sera from Mice Immunized with a KWC Bacteria Expressing a Scaffold MPER on their Surfaces To determine whether immunization with bacteria expressing an MPER-derived protein on their surfaces can elicit an HIV neutralizing humoral immune response, mice were immunized with formalin killed bacteria expressing the 3AGJ scaffold MPER on their surfaces, via the intranasal route, with $10^8$ cells on day 1 and then $10^9$ cells on day 3. Neutralization activity was assessed using HXB2 pseudovirus TZM-bl assay (see e.g., Huang et al., 2012).

Figure 5:
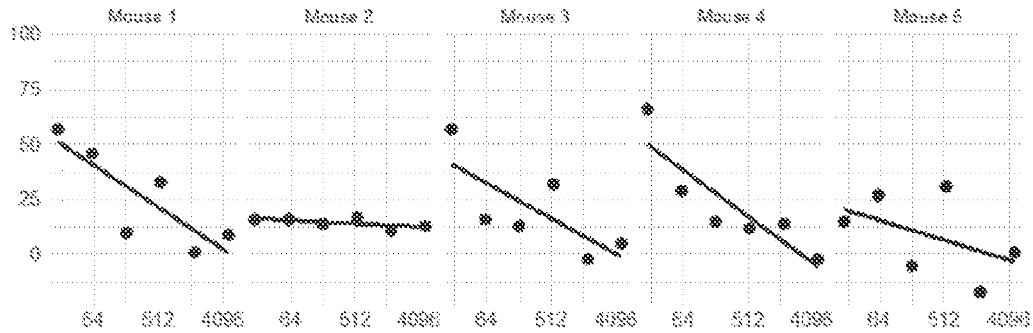
FIG. 5 is a set of plots showing HIV neutralizing activity elicited by intranasal immunization of mice using formalin killed whole cell Gram-negative bacteria expressing the 3AGJ scaffold MPER
Figure 5:
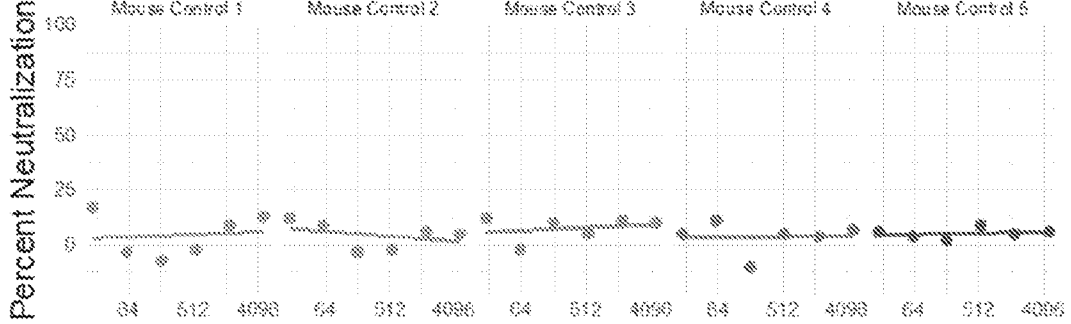
Figure 5:
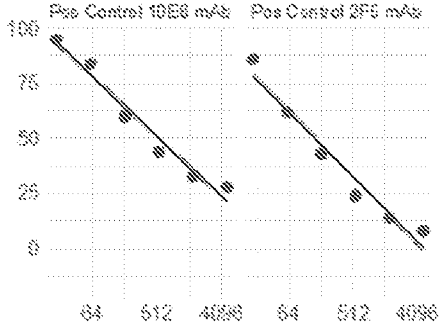

FIG. 5 shows the results of this experiment. The top row of FIG. 5 shows neutralization by serial dilutions of sera from mice that had been immunized with KWC vaccine surface expressing 3AGJ. The data showed that the sera showed neutralizing activity that diminished at higher dilutions. The middle row shows neutralization results obtained using sera from mice immunized with the same bacteria and the same immunization protocol except that these bacteria did not express the 3AGJ scaffold MPER. There was no apparent neutralizing activity and no change in neutralizing activity at higher dilutions. The bottom two panels show neutralization results for serial dilutions of purified anti-MPER BN MAbs 2F5 and 10E8 as a positive control. The data showed strong HIV neutralization, diminishing at higher dilutions.

Overall, the data from EXAMPLES 1-4 indicated that a number of HIV MPER-related antigens could be expressed on the surface of bacteria such that those antigens were recognized by their cognate BNMAbs, that when mice were immunized with the bacteria expressing the HIV MPER-related antigens the production of a humoral immune response was elicited in sera and vaginal wash material capable of binding bacteria surface expressing the MPER-derived antigens. In one example, it was demonstrated that the elicited sera had HIV neutralizing activity. The data supported that the bacterial surface expression of MPER-related antigens represented a novel and plausible approach for HIV vaccine development.

Overview of Examples 5-11

Above, it is shown that MPER-derived proteins could be expressed on the surfaces of bacteria, that those MPER-derived proteins bound anti-HIV BNMAbs, and that when those constructs were used to immunize mice, as intranasal killed whole cell vaccines and as oral live bacteria, they elicited sera/vaginal wash material that bound the surface-expressed MPER-derived proteins, and in one case neutralize HIV.

Live bacteria, for example *Salmonella*, are envisioned to have several advantages, which include: (a) the MPER derived antigens are mobile in the bacterial outer membrane, providing greater access to the surrounding lipid bilayer and interactions with the lipid bilayer constitute an aspect of virion binding for some anti-MPER BNMAbs; (b) avoidance of formalin fixation, which may diminish accessibility of the MPER-derived antigen to the immune system due to cross-linking of multiple proteins in the bacterial outer membrane; and (c) the biological features of *Salmonella* (exit out into the gut-associated lymphoid tissue and replication both extracellularly and within professional phagocytes) aid the development of mucosal immune responses. For each candidate vaccine, surface expression is assessed, test binding of BNMAbs by flow cytometry is assessed, and test immunogenicity in vivo is assessed. Also assessed is the induction of humoral immunity (oral secretions, vaginal washes, fecal extracts, and sera), including binding to the surface-expressed MPER-derived proteins by flow cytometry, and induction of cellular immunity. Expression variants (plasmid copy number, expression, and lysis systems) that are most immunogenic individually are determined, and then those best systems are tested in heterologous prime/boost schedules. Both binding in the flow cytometry assays and in neutralization studies are tested. Anti-MPER binding activity in oral samples, vaginal washes, fecal extracts, and serum is tested. Induction of cellular immune responses is tested. Candidates for subsequent humanized mouse HIV infection challenge experiments are selected. Denton et al., 2014; Denton et al., 2008; Denton et al., 2010; Denton et al., 2011.

Example 5

Producing Oral HIV-1 Vaccine Constructs with MPER-Derived Proteins Placed on the Bacterial Surface Using AT Expression Cassettes Recombinant Gram$^-$ bacterial vaccines employing a monomeric autotransporter expression cassette are produced based on three MPER-derived proteins set forth herein above: 3AGJ, ES2, and ScafMPER.024 (like 3AGJ, designed to mimic the 10E8 binding site). Monomeric AIDA-I AT expression cassettes are used to place these MPER immunogens on the bacterial surface. As in EXAMPLES 1-4, expression systems are initially constructed under the control of a rhamnose-inducible promoter, to establish maximal levels of antigen production not toxic to the bacteria. Guided by these results, each construct is cloned into regulated expression plasmids with alternate origins of replication, promoter modifications in the plasmids, and codon selection to yield the ideal levels of immunogen expression. These variations achieve maximal levels of protein production possible for the bacteria and provide systems that express lower amounts of MPER-derived proteins as controls and comparators.

For each of the MPER-derived proteins, alternates are synthesized that contain varying numbers of additional glycine residues between the AIDA-I AT and the MPER-scaffold, to test and optimize placement of the MPER-derived protein with respect to the AT β-barrel pore and the outer membrane's lipid bilayer. The glycine residues provide a flexible extension for optimizing placement of the MPER immunogen with respect to the β-barrel and bacterial membrane. The design goal is to express the MPER-scaffold far enough out of the beta-barrel pore to be fully exposed to the immune system but close enough to the lipid membrane to promote the development of antibodies with a long, hydrophobic CDR H3 region, which play a role broad neutralization. These constructs are tested to see which have the most native-like affinities for their respective BNMAbs. The best BNMAb binding constructs are selected using serial dilution/flow cytometric studies to obtain semi-quantitative binding curves.

For the trimeric MPER constructs, native gp41 MPER/transmembrane domain (Montero et al., 2008) constructs are synthesized, using the trimeric Hia AT expression cassette to express native MPER plus the N-terminus of the gp41 transmembrane domain on the bacterial cell surface. Three alternate ways to fuse MPER to Hia are designed, matching heptad assignments from the gp41 transmembrane domain, which is expected to promote the trimeric, coiled-coil conformation of native MPER. Additional variants that contain a trimeric GCN4 motif (Harbury et al., 1993) at the N-terminus of native MPER are designed to further stabilize the trimer to promote presentation of the MPER in its native confirmation at the cell surface (Yang et al., 2000; Liu et al., 2009; Hulsik et al., 2013). In some constructs, portions of the gp41 transmembrane domain (TMD) are included since inclusion of the TMD increases 10E8 affinity (Reichart et al., 2016) and some crystal structures show the 10E8 binding site extends to this region (Rujas et al., 2016). A series of constructs with these modifications and fusions with different linker lengths to place the MPER sequence at alternative locations with respect to the β-barrel and outer membrane are made and which constructs have the highest affinities for the 2F5 and 10E8 BNMAbs in flow cytometry serial dilution experiments is tested. First produced are rhamnose-inducible constructs, subsequently down-selecting candidates based on the BNMAb affinities before moving the constructs to the RASV modulated expression plasmids for testing for ability to elicit immune responses. Because the structures of trimeric ATs strongly resemble the structure of the HIV envelope trimer embedded in the virion envelope, the constructs are envisioned to recapitulate the native trimeric, coiled-coil confirmation of the gp41 MPER and transmembrane domains (Chan et al., 1997; Meng et al., 2006).

Example 6

Production and Bacterial Toxicity Testing of MPER-Proteins on the Surface of a Live *Salmonella* Vaccine It is shown in EXAMPLES 1-4 that AIDA-I expression cassettes functioned in Gram$^-$ bacteria, and that these could place MPER-scaffold proteins on the bacterial surface such that anti-MPER BNMAbs could bind MPER-scaffolds. For each construct, the quantity of each MPER scaffold antigen and native trimeric MPER peptide that could be placed on the surfaces of the bacteria without bacterial toxicity (no growth inhibition) is determined, quantifying protein by immunoblot. Once conditions under which production of vaccine antigens is not toxic to the bacteria are established and surface expression is confirmed, vaccination experiments are initiated. Rhamnose-inducible versions, both AIDA-I and trimeric Hia expression cassettes are synthesized. Low, medium, and high copy ori versions of the plasmids can be produced, comparing protein production with the rhamnose dose-response experiments, monitoring protein production by SDS-PAGE and immunoblot. Bacterial toxicity of MPER immunogens is further assessed by testing the stability of the plasmids, passaging bacteria for at least 50 generations (5 successive subcultures using 1:1000 dilutions). For inducible protein production, strains are grown under permissive and non-permissive conditions. MPER-derived protein production is re-confirmed, repeat growth curves are conducted, and the MPER-derived protein-encoding plasmids are resequenced. Colony production and morphology are monitored when plated on medium with and without induction at subculture. Once the maximal antigen production possible without toxicity is determined, protein copy number/cell is determined and the appropriate plasmid and ori type (low, medium, or high) is selected for immunizations.

Example 7

Design and Testing of MPER Expression Cassettes

Multiple variant MPER-derived immunogens are tested to create a maximally immunogenic vaccine. For the scaffold MPERs, expression cassettes are produced based on three MPER-derived proteins: 3AGJ, ES2, and ScafMPER.024, and other scaffold MPERs as developed, using monomeric AIDA-I AT surface expression cassettes. Variants are synthesized that contain differing numbers of glycine residues between the AIDA-I AT and the scaffold MPER to optimize placement of the scaffold MPER protein with respect to the AT β-barrel pore and the OM lipid bilayer. The scaffold MPER is expressed far enough out of the β-barrel pore to be fully exposed to the immune system but close enough to the bilayer to promote development of antibodies that interact with the bilayer, which have previously been shown to be important for broad neutralization (Rujas et al., 2016; Soto et al., 2016; Lu, 2009; Tomaras & Haynes, 2010; Kardani et al., 2016; Musich & Robert-Guroff, 2016).

For native trimeric MPER immunogens, constructs are made using the Hia AT expression cassette to express native MPER peptide plus the N-terminus of the gp41 transmembrane domain on the bacterial surface (Montero et al., 2008). The constructs should recapitulate native trimeric, coiled-coil confirmation of gp41 MPER and transmembrane domains (Chan et al., 1997; Meng et al., 2006), as supported by the data described in EXAMPLES 1-4 (See e.g., FIG. 1). Three alternate ways to fuse MPER to Hia are designed, matching heptad assignments from the gp41 transmembrane domain (TMD), which are expected to promote trimeric, coiled-coil conformations of native MPER. Additional variants are designed that contain a GCN4 trimerization motif (Harbury et al., 1993) and others with an HIV Env trimerization motif to further stabilize trimers, promoting presentation of MPER in its native confirmation (Yang et al., 2000; Liu et al., 2009; Hulsik et al., 2013). Some constructs include portions of the gp41 TMD since inclusion of the TMD increases 10E8 affinity (Reichart et al., 2016), and some crystal structures show the 10E8 binding site extends to the TMD (Rujas et al., 2016). Constructs are made with these modifications and fusions with different linker lengths to place the MPER sequence at alternative locations with respect to the β-barrel and OM. Constructs are tested to determine which have the highest affinities for the BNMAbs, judged by a serial dilution/flow cytometric studies, staining with goat Anti-Human IgG FITC (Abcam) secondary Ab, to determine 50% and 10% BNMAb concentration. Constructs are synthesized in a plasmid with a rhamnose-inducible promoter to determine maximum expression without bacterial toxicity, subsequently down-selecting candidates based on BNMAb affinities before making KWC vaccines and moving constructs to the RASV systems for testing for ability to elicit immune responses.

Example 8

Production and Bacterial Toxicity Testing of MPER-Proteins on the Surface of Bacteria The quantity of each MPER-derived antigen that can be placed on the surfaces of the bacteria without bacterial toxicity is determined. Rhamnose-inducible versions are initially synthesized. Constructs are cloned into low, medium, and high copy ori plasmids, and into plasmids with built-in affinity tags (His6, HA, FLAG), which are used to make MPER constructs for ELISAs and protein interaction studies, if needed (see below). Protein production with the rhamnose dose-response experiments is evaluated, monitoring protein production by immunoblot. Bacterial toxicity of MPER immunogens is assessed by assessing maintenance and stability of the plasmids, passaging bacteria for at least 50 generations (5 successive subcultures using 1:1000 dilutions). For inducible protein production strains are grown under permissive and non-permissive conditions, and the MPER-derived protein-encoding plasmids are resequenced. Colony production and morphology are monitored when plated on medium with and without induction at subculture. Once maximal antigen production possible without toxicity is determined, preferred vectors are selected for subsequent experiments.

The ability of BNMAbs to bind MPER-derived proteins on the bacterial surface is tested using flow cytometry. These experiments will follow closely those used in EXAMPLES 1-4 for data shown in FIG. 1. Each surface-expressed construct is tested with 2F5, 4E10, and 10E8 BNMAbs, using goat anti-human AlexaFluor 488 antibody as secondary Ab. Primary Ab binding is assessed in a series of 2-fold serial dilutions, from 1:500 to 1:16000, to optimize flow cytometry conditions. The region of highest cell population density is gated to ensure only viable cells are analyzed. Bacteria transformed with plasmids that place HA immunotags on the bacterial surface using the AT expression cassette are used as positive controls. Cells transformed with a plasmid with an empty expression cassette serve as a negative control for both sets of studies.

Example 9

Evaluate the Ability of Vaccines to Elicit Production of MPER-Specific Neutralizing Sera Immunization with KWC vaccines. Mice are immunized intranasally, as described above in EXAMPLES 1-4. Alternate immunization routes, including subcutaneous injection (formalin-fixed bacteria in 200 μl 1×PBS and 1 μg of cholera toxin B subunit (CTB)) and oral immunization (following buffer administration, bacteria resuspended in 200 μl 10% sucrose solution with 1 μg CTB by gavage are also tested. The immunization method yielding the best immune responses as judged by the flow cytometry dilution studies is adopted as a standard for future comparisons of the different immunogens and in the KWC vaccine protection experiments. Conventional prime/boost regimens plus alternate day exponentially increasing doses are tested for the most effective route.

Evaluating humoral immunity. Sera are evaluated for their ability to bind MPER-derived antigens using bacteria placing chimeric MPER proteins on the bacterial cell surface as in EXAMPLES 1-4 via flow cytometry, using serial dilutions, with goat Anti-Mouse IgG FITC (Invitrogen) as secondary Ab (FIGS. 1-3).

Evaluating mucosal immunity. Anti-MPER mucosal immune responses are evaluated in fecal extracts and vaginal washes. Fecal pellets are resuspended in 1×PBS/0.01% sodium azide, vortexed until homogenized, clarified by centrifugation, and stored as supernatants at −80° C. For vaginal mucosal immunity vaginal washes (50 ul PBS washes) are tested. For GI and vaginal humoral immunity studies, flow cytometric assays as in EXAMPLES 1-4 are run. Serial 5-fold dilutions and assays using goat anti-mouse IgG- and IgA-FITC (since ~50% of vaginal Abs are IgG and 50% IgA) are run. Simultaneous positive controls are run with the known BNMAbs (and appropriate anti-human secondary Abs).

HIV neutralization assays. To determine if MPER vaccines elicit anti-HIV neutralizing immune responses, and to assess neutralization breadth the single-round Env pseudovirus TZM-bl method (Montefiori, 2009; Huang et al., 2012) is employed using an env panel developed to standardize assessment of vaccine-induced Abs (Li et al., 2005). An abbreviated panel of 15 viruses is first tested, with subsequent expansion for vaccines showing evidence of eliciting neutralizing responses, with sera induced by vaccinating larger animals (guinea pigs or rabbits, once the most effective immunogen in mouse studies is determined), and Abs isolated from mucosal sites. Sera are compared with both negative controls (pre-immune, mice immunized with bacteria not expressing Ag) and positive controls (2F5, 4E10, 10E8 BNMAbs). Pre-titrated doses are incubated of pseudovirus with serial dilutions of sample in duplicate. Freshly trypsinized TZM-bl cells are added to each well. One set of control wells receives cells+pseudovirus (virus control) and another receives cells only (background control). After 48 hours, medium is removed from each well, and assayed using a luciferase detection system. Neutralization titers are the dilution of sera at which luminescence is reduced by 50% or 90% compared to virus control wells after background subtraction ($ID_{50}$ and $ID_{90}$). Serial dilutions of mouse terminal bleeds, vaginal washes, and coproantibodies are studied. If studies confirm that the immunogen induces a BN response against MPER, a long-term culture experiments to assess the evolution of escape mutants is studied.

Testing for MPER specificity. To test for MPER specificity the neutralizing ability of the sera elicited against an HIV-1 sensitive to all known MPER-BNMAbs (CNE59), HIV-2 (MPER-BNMAb resistant, 7312A.Y720S), and an HIV-2 chimera with an HIV-1 MPER (MPER-BNMAb sensitive, 7312A.C1.Y720S; Davis et al., 2009; Sanchez-Merino et al., 2016) is compared.

Evaluating cell-mediated immunity (CMI). To evaluate CMI induction against MPER, T-cell phenotypes of spleen cells obtained at sacrifice are compared in the unvaccinated versus vaccinated mouse samples based on CD4, CD8, CD45RA, CD45RO, CD62L, CD27, CD28 and CCR7, and chemokine receptor expression, using antibodies CCR7, CCR4 and CXCR3 and CLA. Also evaluated is T-cell cytokine release by intracellular cytokine assay (for CD3+/62L-+/RAneg/IFNγ/IL-2 double secreting central memory T-cells) and Cytokine Bead Array (Weber et al., 2013a; Weber et al., 2013b). To determine whether vaccination can elicit a T-cell response to MPER (obtained from Proimmune as a full-length peptide and/or affinity purified tagged scaffold MPER synthesized in *E. coli*), the frequency of CTL precursors specific for MPER is measured, plus responses to Gag as a negative control by ELIspot. If there is a failure to detect MPER-specific T-cells, sensitivity is increased by adding a prior stimulation step (MPER pulse), then testing in an IFNγ ELISpot assay (Cruz et al., 2013).

Example 10

Production of at Least 2 Different Recombinant Bacterial Vaccines that Demonstrate MPER-Specific Neutralization Demonstration of neutralization. For this part, neutralization is quantified by computing the log-slope for each of 5 animals in a serial dilution neutralization study, as per EXAMPLES 1-4. A one-sided, one-sample t-test is used to compare the mean of these slopes to 0, with the alternative hypothesis that the mean slope is less than 0. The development of ≥2 candidate vaccines for which the mean slope is significantly different from 0, while the control slopes are not significantly different from 0, is target. With 5 animals per group, the one-sample t-test has 80% power, with a one-sided significance level of 5%, for an effect size of −1.37.

Demonstration of MPER specificity. Immune responses elicited by candidate vaccines demonstrate MPER specificity by showing neutralization of HIV-1, no neutralization of HIV-2, and neutralization of a chimeric HIV-2 with HIV-1 MPER, as described above.

Example 11

Production of MPER-Derived Immunogens in Mutant Bacteria

Various strategies can be used to enhance the immunogenicity of recombinant bacterial vaccine antigen expression vectors and systems. These include bacteria administered with additional adjuvants, bacteria engineered to produce material with adjuvant activity, such as pathogen-associated molecular patterns (PAMPs) like pili, fimbriae, nucleic acid, LPS, bacteria engineered to be less reactogenic, such as alterations in LPS production, bacteria with one or small numbers of mutations or deletions in immunosuppressive genes, and/or bacterial that have had large numbers of non-essential genes deleted or mutated.

Alternatives for Examples 1-11

Two independent antigen routes are pursued to produce MPER recombinant bacterial vaccines: scaffold MPERs surface expressed via a monomeric AT, such as AIDA-I, and native trimeric AVER, expressed via a trimeric AT, such as Hia. Also tested are both KWC and live a Gram⁻ bacterial vaccine systems. Independent routes to an MPER-based vaccine substantially enhance the likelihood of success.

Alternative immunization schedules. Since both the 3AGJ and scafMPER.024 are designed to bind the 10E8 BNMAb, to enhance development of 10E8-like Ab responses while minimizing responses against other irrelevant epitopes in the scaffolds, a prime-boost strategy can be used, priming with one and boosting with the other (3AGJ, then scafMPER.024, and/or vice versa). In this case, since the scaffolds are completely different, the only epitope shared among the prime and boost would be the MPER epitope, enhancing the development of a specific anti-MPER immune response. The trimeric native MPER vaccines offer a similar option.

Alternative bacterial lipid profiles. The known anti-MPER BNMAbs interact both with MPER and with the lipid bilayer in the virion envelope. It is shown that the bacteria we tested can elicit an anti-MPER response with neutralizing activity, but responses may be improved if we alter the OM lipid composition to make it more similar to mammalian membranes. If it is desired to enhance responses the binding of the BNMAbs to MPER-derived surface expressed immunogens is tested in bacteria transformed with a plasmid containing phosphatidylethanolamine N-methyltransferase, which catalyzes the production of phosphatidyl choline (PC) from phosphatidyl ethanol, since mammalian membranes have increased PC (Hanada et al., 2001).

Alternatives to flow cytometric assays to test for induction of anti-MPER immune responses. It is believed the bacterial flow cytometric dilution assay is best, since it evaluates binding to the MPER antigen expressed in the context of a lipid bilayer, which is important for binding of the known anti-MPER BNMAbs. But, as an alternative, the humoral response by ELISA is evaluated, built with MPER peptide (synthetic peptide or recombinant produced via affinity purification of bacterially expressed immunotags (e.g., HA) with an alkaline phosphatase conjugated anti-mouse antibody as the secondary and luminescent detection (Huang et al., 2012).

Alternative MPER scaffold proteins. For AT antigen production the MPER scaffold proteins as disclosed herein above are employed. But, substantially different scaffold MPERs (Ho et al., 2008; Lee et al., 2000) are available and these represent alternatives.

Alternative Ab assays and production. In the case of the observation of high background binding with mouse sera and in some instances relatively lower neutralization titers, alternative approaches are provided. Several approaches can mitigate high background in binding assays: blocking agents (serum albumin, milk proteins, FBS, fish serum (e.g., SEA BLOCK), but if needed, key immunizations are repeated in another species that tends to give lower backgrounds and/or better neutralization activity (e.g., guinea pigs and/or rabbits), which also enable collection of larger amounts of mucosal antibodies from oral samples, vaginal washes, and feces, and much larger amounts of sera.

Alternative approaches—animal toxicity. An MPER vaccine might elicit an autoreactive immune response. However, identifying any vaccine that elicited good anti-MPER BN activity provides a "lead immunogen" for optimization. Several approaches are used to refine engineering of the recombinant AT-MPER. Modifications can include adding sequence to 'push out' MPER further from the β-barrel and the bacterial outer membrane lipid bilayer so that MPER is farther from the lipid bilayer.

Summary of Examples 1-11

In summary, several bacteria-based HIV MPER vaccine candidates have been developed. These candidates express MPER-derived antigens on their surfaces using Gram⁻ autotransporters. The surface-expressed MPER antigens bind several different MPER-directed anti-HIV Broadly Neutralizing Monoclonal Antibodies. When the bacteria expressing the MPER-derived antigens on their surfaces are used to immunize mice they elicit the production of sera and vaginal wash material that bind the bacteria expressing the MPER antigens. At least one of the bacteria expressing MPER-derived antigens on their surfaces elicits the production of sera with anti-HIV neutralizing activity. Killed whole cell and live *Salmonella* expressing the MPER derived antigens on their surfaces constitute new and effective approaches to HIV vaccine development that can yield an inexpensive, globally appropriate candidate vaccine that could be rapidly produced and deployed largely using currently available technology.

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

REFERENCES

All references listed in the instant disclosure, including but not limited to all patents, patent applications and publications thereof, scientific journal articles, and database entries (including but not limited to UniProt, EMBL, and GENBANK® biosequence database entries and including all annotations available therein) are incorporated herein by reference in their entireties to the extent that they supplement, explain, provide a background for, and/or teach methodology, techniques, and/or compositions employed herein. The discussion of the references is intended merely to summarize the assertions made by their authors. No admission is made that any reference (or a portion of any reference) is relevant prior art. Applicants reserve the right to challenge the accuracy and pertinence of any cited reference.

Alam et al. (2009) Role of HIV membrane in neutralization by two broadly neutralizing antibodies. Proc Natl Acad Sci USA. 106(48):20234-9.

Altschul et al. (1990a) J Mol Biol. 215(3):403-10.

Altschul et al. (1990b) Proc Natl Acad Sci USA. 87(14):5509-13.

Altschul et al. (1997) Nucleic Acids Res. 25(17):3389-402.

Ameiss et al. (2010) Vaccine. 28(41):6704-13.

Ashraf et al. (2011) Vaccine. 29(23):3990-4002.

Atkins et al. (2006) Vaccine. 24(15):2710-7.

Benz & Schmidt (1989) Infect Immun. 57(5):1506-11.

Benz & Schmidt (1992) Mol Microbiol. 6(11):1539-46.

Bodanszky & Bodanszky (1984) in *The Practice of Peptide Synthesis*, Springer-Verlag, New York, New York, United States of America.

Brenneman et al. (2012) J Microbiol Methods. 89(2):137-47.

Brenneman et al. (2013) J Bacteriol. 195(13):3062-72. 3697538

Buchacher et al. (1994) AIDS Res Hum Retroviruses. 10(4): 359-69.

Burton et al. (2012) Cell Host Microbe. 12(4):396-407.

Buzon et al. (2010) PLoS Pathog. 6(5):e1000880.

Calarese et al. (2003) Science. 300(5628):2065-2071.

Chan et al. (1997) Cell. 89(2):263-273.

Chateau et al. (2013) J Virol. 87(2):1274-7. 3554084

Chen et al. (2009) Science. 326(5956):1123-1127.

Chin'ombe (2013) Viruses. 5(9):2062-78. 3798890

Chin'ombe & Ruhanya (2013) Open Virol J. 7:121-6. 3905348

Chou & Fasman (1974) Biochemistry 13:222-245.

Chou & Fasman (1978) Ann Rev Biochem. 47:251-276.

Chou & Fasman (1979) Biophys J. 26:367-384.

Colligan et al. (eds.) (1994-2004) *Current Protocols in Immunology*, John Wiley & Sons, Inc., New York, New York, United States of America.

Correia et al. (2010) Structure. 18(9):1116-26.

Correia et al. (2011) J Mol Biol. 7; 405(1):284-97.

Cotter et al. (2006) J Bacteriol. 188(15):5400-5407.

Cruz et al. (2013) Clin Exp Immunol. 174(1):89-96.

Curtiss et al. (1991) Nonrecombinant and recombinant avirulent *Salmonella* live vaccines for poultry. in Blankenship et al. (eds) (1991) *Colonization control of human bacterial enteropathogens in poultry*. Academic Press, New York, New York, United States of America. pp. 169-98.

Curtiss et al. (2009) Infect Immun. 77(3):1071-82. 2643627

Curtiss et al. (2010) Crit Rev Immunol. 30(3):255-70.

Davis et al. (2009) J Virol. 83(3):1240-59. PMC2620909

Dawood et al. (2013) Aids. 27(5):717-30.

Denton et al. (2008) PLoS Med. 5(1):e16. 2194746

Denton et al. (2010) PLoS One. 5(1):e8829. 2809117

Denton et al. (2011) J Virol. 85(15):7582-93. 3147928

Denton et al. (2014) Vaginal and Rectal HIV Transmission in Humanized Mice. in Poluektova et al. (eds) (2014) *Humanized Mice for HIV Research*. Springer, New York, New York, United States of America. pp. 235-45.

Deutscher et al. (ed.) (1990) *Guide to Protein Purification*, Harcourt Brace Jovanovich, San Diego, California, United States of America.

Devereux et al. (1984) Nucleic Acids Res. 12(1 Pt 1):387-95.

Doria-Rose et al. (2016) J Virol. 90(1):76-91.

Ehretsmann et al. (1992) Genes Dev. 6(1):149-59.

Excler et al. (2013) Curr Opin HIV AIDS. 8(5):421-31.

Falkowska et al. (2014) Immunity. 40(5):657-68.

Frey et al. (2013) Vaccine. 31(42):4874-80.

Galan et al. (1990) Gene. 94(1):29-35.

Galen et al. (2009) Immunol Cell Biol. 87(5):400-12.

Garmory et al. (2003) Vaccine. 21(21-22):3051-3057.

Gerhardt et al. (eds.) (1994) *Methods for General and Molecular Bacteriology*, American Society for Microbiology, Washington, D.C., United States of America. p. 574.

Gross & Mienhofer (eds.) (1981) *The Peptides, vol.* 3, Academic Press, New York, New York, United States of America. pp. 3-88.

Grundner et al. (2005) Virology. 331(1):33-46.

Gunn et al. (2010) Clin Vaccine Immunol. 17(3):354-62.

Hanada et al. (2001) Biosci Biotechnol Biochem. 65(12): 2741-8.

Harbury et al. (1993) Science. 262(5138):1401-7.

Hashimoto et al. (2005) Mol Microbiol. 55(1):137-49.

Henderson et al. (2000) Trends Microbiol. 8(12):529-532.

Ho et al. (2008) Infect Immun. 76(1):111-119.

Huang et al. (2012) Nature. 491(7424):406-12.

Huang et al. (2014) Nature. 515(7525):138-42.

Hulsik et al. (2013) PLoS Pathog. 9(3):e1003202.

Irimia et al. (2017) PLoS Pathog. 13(2):e1006212. PMC5338832

Jacob et al. (2015) J Virol. 89(10):5264-75. PMC4442498

Jiang et al. (2015) Avian Diseases. 59(4):475-85.

Jose & Meyer (2007) Microbiol Mol Biol Rev. 71(4):600-619.

Juarez-Rodriguez et al. (2012) Infect Immun. 80(2):815-31. 3264310

Julien et al. (2010) J Virol. 84(9):4136-47. PMC2863773

Kardani et al. (2016) Vaccine. 34(4):413-23.

Karlin & Altschul (1993) Proc Natl Acad Sci USA 90:5873-5877.

Karlin & Altschul (1990) Proc Natl Acad Sci USA. 87(6): 2264-8.

Karpenko et al. (2012) Microb Biotechnol. 5(2):241-50. 3815784

Kato & Hashimoto (2007) Mol Syst Biol. 3:132. PMC1964801

Kittlesen et al. (1998) J Immunol. 60:2099-2106.

Kjaergaard et al. (2002) J Bacteriol. 184(15):4197-4204.

Kong et al. (2008) Proc Natl Acad Sci USA. 105(27):9361-6. 2453710

Kong et al. (2011a) Infect Immun. 79(10):4227-39. 3187260

Kong et al. (2011b) J Immunol. 187(1):412-23.

Kong et al. (2012a) Infect Immun. 80(9):3215-24. 3418755

Kong et al. (2012b) Proc Natl Acad Sci USA. 109(47): 19414-19419.

Kong et al. (2013) Expert Rev Vaccines. 12(4):345-347.

Kong et al. (2015) J Virol. 89(5):2659-71. PMC4325730

Kong et al. (2016) Science. 352(6287):828-833.

Kotton et al. (2006) Vaccine. 24(37-39):6216-24.

Kramer et al. (2003) Infect Immun. 71(4):1944-1952.

Kwong et al. (2013) Nat Rev Immunol. 13(9):693-701.

Kyte & Doolittle (1982) J Mol Biol. 157:105-132.

Lai et al. (2014) J Biol Chem. 289(43):29912-26. PMC4208001

Lee et al. (2000) Nat Biotechnol. 18(6):645-648.

Lee et al., (2003) Trends Biotechnol. 2003 January; 21(1): 45-52. Review. PubMed PMID: 12480350

Li et al. (2005) J Virol. 79(16):10108-25.

Li et al. (2008) Infect Immun. 76(11):5238-46. 2573344

Li et al. (2009) Proc Natl Acad Sci USA. 106(2):593-8. 2626748

Li et al. (2016) Sci Rep 6:29556.

Lin-Chao et al. (1994) J Biol Chem. 269(14):10797-803.

Liu et al. (2009) Biochemistry. 48(13):2915-23.

Liu et al. (2018) Protein & Cell 9(7):596-615.

Lottenbach et al. (2013) Clin Vaccine Immunol. 20(9):1473-8.

Lu (2009) Curr Opin Immunol. 21(3):346-51.

Mascola & Haynes (2013) Immunol Rev. 254(1):225-244.

Mascola & Montefiori (2010) Annu Rev Immunol. 28:413-444.

McDowall et al. (1995) Nature. 374(6519):287-90.

McLellan et al. (2011) Nature. 480(7377):336-343.

Meng et al. (2006) EMBO J. 25(11):2297-2304.

Mohan et al. (2014) Immunobiology. 219(4):292-301.

Molinos-Albert et al. (2014) Retrovirology. 11(1):44.

Molinos-Albert et al. (2017) Frontiers in Immunology, Vol. 8, Article 1154.

Montefiori (2009) in Prasad & Kalpana (eds.) *HIV Protocols: Second Edition* (*Methods in Molecular Biology*). Humana Press, New York, New York, United States of America. pp. 395-405.
Montero et al. (2008) Microbiol Mol Biol Rev. 72(1):54-84, table of contents.
Morgan & Gainor (1989) Ann Rep Med Chem. 24:243-252.
Morris et al. (2011) PLoS One. 6(9):e23532.
Mouquet et al. (2012) Proc Natl Acad Sci USA. 109(47): E3268-77.
Musich & Robert-Guroff (2016) Expert Rev Vaccines. 15(8):1015-27.
Muster et al. (1993) J Virol. 67(11):6642-6647.
Nakayama et al. (1988) Bio/Tech. 66:693-7.
Nicolay et al. (2015) Crit Rev Microbiol. 41(1):109-23.
Ofek et al. (2010a) Proc Natl Acad Sci USA. 107(42): 17880-7. 2964213
Ofek et al. (2010b) J Virol. 84(6):2955-62. PMC2826063
PCT International Patent Application Publication Nos. WO 1993/18163; WO 1996/40943; WO 1997/09437; WO 1999/54464; WO 2004/110486; WO 2006/012539.
PCT International Patent Application Serial No. PCT/US2005/026102.
Pejchal et al. (2011) Science. 334(6059):1097-1103.
Phogat & Wyatt (2007) Curr Pharm Des. 13(2):213-27.
Pompa-Mera et al. (2011) Exp Parasitol. 129(4):393-401.
Rapp & Kaufmann (2004) Int Immunol 16(4):597-605.
Reichart et al. (2016) Angew Chem Int Ed Engl. 55(8):2688-92.
*Remington: The Science and Practice of Pharmacy, 19th ed.* (1995) Mack Publishing, Easton, Pennsylvania, United States of America.
*Remington's Pharmaceutical Sciences, 18th ed.* (1990) Mack Publishing, Easton, Pennsylvania, United States of America.
Rizos et al. (2003) Infect Immun. 71(11):6320-6328.
Robert-Guroff et al. (1985) Nature. 316(6023):72-4.
Ruiz-Olvera et al. (2003) Plasmid. 50(1):12-27.
Ruiz-Perez et al. (2002) Infect Immun. 70(7):3611-3620.
Ruj as et al. (2016) Sci Rep. 6:38177.
Salzwedel et al. (1999) J Virol. 73(3):2469-2480.
Sanchez-Merino et al. (2016) J Virol. 90(11):5231-45 PMC4934761
Sanders et al. (2015) Science. 349(6244):aac4223.
Saunders et al. (2012) Aids. 26(10):1293-302.
Scherer et al. (2010) Proc Natl Acad Sci USA. 107(4):1529-34. PMC2824387
Shata et al. (2001) Vaccine. 20(3-4):623-9.
Shi et al. (2010a) Clin Vaccine Immunol. 17(3):363-71. 2837964.
Shi et al. (2010b) PLoS One. 5(6):e11142. 2887840
Shi et al. (2013) Clin Vaccine Immunol. 20(6):931-44.
Simon et al. (1963) Appl Microbiol. 11:371-6. 1058006
Sok et al. (2014) Proc Natl Acad Sci USA. 111(49):17624-9.
Soto et al. (2016) PLoS One. 11(6):e0157409.
Spatola (1983) *Chemistry and Biochemistry of Amino Acids, Peptides and Proteins, Vol. VII*. Weinstein (ed.). Marcel Dekker, Inc., New York, New York, United States of America. pp. 267-357.
Stewart et al. (1984) in *Solid Phase Peptide Synthesis, 2nd Edition*, Pierce Chemical Company, Rockford, Illinois, United States of America.
Sun et al. (2016) Emerg Microbes Infect. 5:e65. PMC4932654
Surana et al. (2004) J Biol Chem. 279(15):14679-14685.
Tomaras & Haynes (2010) Curr Opin HIV AIDS. 5(5):421-7.
Trkola et al. (1996) J Virol. 70(2):1100-8.
Tsunetsugu-Yokota et al. (2007) AIDS Res Hum Retroviruses. 23(2):278-86.
U.S. Patent Application Publication No. 2009/0270312.
U.S. patent application Ser. No. 11/572,453.
U.S. Pat. Nos. 4,554,101; 5,616,686; 5,821,088; 5,958,736; 7,094,598; 7,314,974; 8,012,932; 8,628,782; 8,637,036; 8,637,234; 8,647,818; 9,175,070; 9,493,549; 9,580,718; 9,695,230; 9,885,051; 9,988,424; 10,035,844; 10,363,301.
van Bloois et al. (2011) Trends Biotechnol. 29(2):79-86.
van Gils et al. (2016) Nat Microbiol. 2:16199.
Wagh et al. (2016) PLoS Pathog. 12(3):e1005520. PMC4814126
Walker et al. (2009) Science. 326(5950):285-9.
Walker et al. (2011a) Nature. 477(7365):466-470.
Walker et al. (2011b) Proc Natl Acad Sci USA. 108(50): 20125-20129.
Wang et al. (2010) Infect Immun. 78(9):3969-80. 2937466
Wang et al. (2011) Infect Immun. 79(2):937-49. 3028866
Wang et al. (2013a) Infect Immun. 81(9):3148-62. PMC3754205
Wang et al. (2013b) Microb Pathog. 58:17-28.
Weber et al. (2013a) Leukemia. 27(7):1538-47.
Weber et al. (2013b) Clin Cancer Res. 19(18):5079-91.
Weiss et al. (1985) Nature. 316(6023):69-72.
Welters et al. (2004) Vaccine. 23(3):305-11.
Xin et al. (2012) Infect Immun. 80(10):3621-33. 3457550
Yang et al. (2000) J Virol. 74(12):5716-25.
Yang et al. (2010) Vaccine. 28(15):2735-2742.
Zhai et al. (2013) Vaccine. 31(46):5422-9. PMC3881962
Zhou et al. (2010) Science. 329(5993):811-817.
Zhu et al. (2011) J Virol. 85(21):11401-11408.
Zugel (2001) Infect Immun. 69(6):4164-7.
Zwick et al. (2001) J Virol. 75(22):10892-10905.
Zwick et al. (2005) J Virol. 79(2):1252-1261.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A modified bacterium, or a derivative thereof, comprising a heterologous antigen expressed on a surface of a membrane of the bacterium, wherein the heterologous antigen is heterologous to the modified bacterium, wherein the heterologous antigen comprises a membrane-proximal external region (MPER) peptide, wherein the MPER peptide comprises a sequence selected from the group consisting of SEQ ID NOs: 5, 6, and 11-13 or a homolog displaying at least 95% sequence identity thereto, wherein the modified bacterium comprises an autotransporter (AT) expression vector encoding the heterologous antigen and wherein the modified bacterium is a killed whole cell modified bacterium or the derivative of the killed whole cell modified bacterium is a minicell.

2. The modified bacterium of claim 1, wherein the bacterium is a Gram-negative bacterium.

3. The modified bacterium of claim 2, wherein the bacterium is selected from the group consisting of *Salmonella, E. coli, Shigella* sp., *Enterobacter* sp., and other Enterobacteriaceae; *Neisseria* sp., *Moraxella* sp., *Haemophilus* sp., *Klebsiella* sp., *Legionella* sp., *Burkholderia* sp., and *Pseudomonas* sp.

4. The modified bacterium of claim 3, wherein in the bacterium is a *Salmonella* or an *E. coli.*

5. The modified bacterium of claim 1, wherein the autotransporter expression vector comprises a *Haemophilus influenzae* (Hia) autotransporter expression vector.

6. The modified bacterium of claim 1, wherein the AT expression vector comprises an expression cassette with a monomeric autotransporter or a trimeric autotransporter.

7. An immunogen composition comprising a modified bacterium according to claim 1 or (b) a purified trimeric MPER antigen and a modified bacterium according to claim 1; and a pharmaceutically acceptable carrier.

8. The immunogen composition of claim 7, wherein the purified trimeric MPER antigen is linked to the surface of a bacterium covalently or non-covalently.

9. An immunogen composition comprising (a) a modified bacterium according to claim 1; and a pharmaceutically acceptable carrier.

10. The immunogen composition of claim 9, wherein the immunogen composition is capable of eliciting a neutralizing immune response or a cellular immune response in a subject.

11. The immunogen composition of claim 9, wherein the immunogen composition is formulated to be administered orally, rectally, vaginally, intra-nasally, parenterally, intradermally, subcutaneously, or intramuscularly.

12. A method of inducing an immune response in a subject in need thereof, the method comprising providing an immunogen composition according to claim 9; and administering the immunogen composition to a subject.

13. The method of claim 12, wherein the immunogen composition is capable of eliciting production of a neutralizing antibody in the subject.

14. The method of claim 12, wherein the immunogen composition is administered orally, rectally, vaginally, intranasally, parenterally, intradermally, subcutaneously, or intramuscularly.

15. The method of claim 12, wherein the immunogen composition is administered to a subject at risk of exposure to HIV or as a treatment to a subject infected with HIV.

16. A method of producing an antibody, the method comprising providing a modified bacterium according to claim 1 and administering the modified bacterium to a subject, whereby an antibody is produced in the subject.

17. The method of claim 16, wherein the antibody is a neutralizing antibody.

18. The method of claim 16, wherein the modified bacterium is provided in a pharmaceutically acceptable carrier.

19. The method of claim 16, wherein the modified bacterium is administered orally, rectally, vaginally, intra-nasally, parenterally, intradermally, subcutaneously, or intramuscularly.

20. An expression vector comprising a nucleotide sequence encoding an antigen, wherein the expression vector is configured to express the antigen on a surface of a bacterium modified to include the expression vector, wherein the expression vector comprises a monomeric or trimeric autotransporter (AT) expression vector, and wherein the antigen comprises a membrane-proximal external region (MPER) peptide, wherein the MPER peptide comprises a sequence selected from the group consisting of SEQ ID NOs: 5, 6, and 11-13 or a homolog displaying at least 95% sequence identity thereto.

21. The expression vector of claim 20, wherein the autotransporter expression vector comprises a *Haemophilus influenzae* (Hia) autotransporter expression vector.

22. The expression vector of claim 20, wherein the nucleotide sequence encoding the antigen is positioned under control of an inducible promoter.

23. The expression vector of claim 20, wherein the antigen is expressed as a monomer or as a trimer.

24. The expression vector of claim 20, provided in a pharmaceutically acceptable carrier.

25. The expression vector of claim 20, wherein the MPER peptide comprises a native MPER amino acid sequence expressed as a trimer.

26. The expression vector of claim 20, wherein the MPER peptide comprises a modified MPER amino acid sequence expressed as a trimer.

27. The expression vector of claim 20, wherein the MPER peptide mimics a native trimeric MPER.

* * * * *